US011390754B2

(12) United States Patent
Singh et al.

(10) Patent No.: US 11,390,754 B2
(45) Date of Patent: *Jul. 19, 2022

(54) COMPOSITIONS COMPRISING A POLYMERIC DYE AND A CYCLODEXTRIN AND USES THEREOF

(71) Applicant: SONY CORPORATION, Tokyo (JP)

(72) Inventors: Sharat Singh, Rancho Santa Fe, CA (US); Tracy Matray, Snohomish, WA (US)

(73) Assignee: Sony Corporation, Tokyo (JP)

(*) Notice: Subject to any disclaimer, the term of this patent is extended or adjusted under 35 U.S.C. 154(b) by 142 days.

This patent is subject to a terminal disclaimer.

(21) Appl. No.: 16/099,988

(22) PCT Filed: May 10, 2017

(86) PCT No.: PCT/US2017/032006
§ 371 (c)(1),
(2) Date: Nov. 8, 2018

(87) PCT Pub. No.: WO2017/197014
PCT Pub. Date: Nov. 16, 2017

(65) Prior Publication Data
US 2019/0136065 A1 May 9, 2019

Related U.S. Application Data

(60) Provisional application No. 62/334,263, filed on May 10, 2016.

(51) Int. Cl.
| | | |
|---|---|---|
| C09B 69/10 | (2006.01) |
| G01N 33/52 | (2006.01) |
| C07F 9/6558 | (2006.01) |
| C07F 9/6561 | (2006.01) |
| C07F 9/655 | (2006.01) |
| G01N 33/50 | (2006.01) |
| C09K 11/02 | (2006.01) |
| C09K 11/06 | (2006.01) |

(52) U.S. Cl.
CPC .......... *C09B 69/103* (2013.01); *C07F 9/6561* (2013.01); *C07F 9/65522* (2013.01); *C07F 9/65583* (2013.01); *C07F 9/65586* (2013.01); *C09K 11/02* (2013.01); *C09K 11/06* (2013.01); *G01N 33/5005* (2013.01); *G01N 33/52* (2013.01); *C09K 2211/145* (2013.01); *C09K 2211/1425* (2013.01)

(58) Field of Classification Search
CPC ....... C09B 69/10; C09B 69/103; C07F 9/098; C07F 9/65586; G01N 21/6428; G01N 33/52; G01N 2021/6439
See application file for complete search history.

(56) References Cited

U.S. PATENT DOCUMENTS

| | | | |
|---|---|---|---|
| 4,450,305 A | 5/1984 | Kamhi | |
| 4,476,229 A | 10/1984 | Fino et al. | |
| 4,778,753 A | 10/1988 | Yamanishi et al. | |
| 5,053,054 A | 10/1991 | Kirchanski | |
| 5,268,486 A | 12/1993 | Waggoner et al. | |
| 5,318,894 A | 6/1994 | Pugia | |
| 5,994,143 A * | 11/1999 | Bieniarz ................. | C09B 69/10 436/106 |
| 6,140,480 A | 10/2000 | Kool | |
| 6,171,859 B1 | 1/2001 | Herrnstadt et al. | |
| 6,218,108 B1 | 4/2001 | Kool | |
| 6,380,431 B1 | 4/2002 | Whipple et al. | |
| 6,479,650 B1 | 11/2002 | Kool | |
| 6,534,041 B1 | 3/2003 | Licha et al. | |
| 6,627,400 B1 | 9/2003 | Singh et al. | |
| 6,670,193 B2 | 12/2003 | Kool | |
| 6,716,452 B1 | 4/2004 | Piccariello et al. | |
| 6,852,709 B2 | 2/2005 | Leong et al. | |
| 7,060,708 B2 | 6/2006 | Piccariello et al. | |
| 7,172,907 B2 | 2/2007 | Chen et al. | |
| 7,423,133 B2 | 9/2008 | Kool et al. | |
| 7,667,024 B2 | 2/2010 | Mao et al. | |
| 7,897,684 B2 | 3/2011 | Bazan et al. | |
| 8,217,389 B2 | 7/2012 | Nakano et al. | |
| 8,293,700 B2 | 10/2012 | Arranz | |
| 8,349,308 B2 | 1/2013 | Yurkovetskiy et al. | |
| 8,431,545 B2 | 4/2013 | Kataoka et al. | |
| 8,802,738 B2 | 8/2014 | Emrick | |
| 8,895,023 B2 | 11/2014 | Rademacher et al. | |
| 8,906,603 B2 | 12/2014 | Castro et al. | |
| 9,085,799 B2 | 7/2015 | Bazan et al. | |

(Continued)

FOREIGN PATENT DOCUMENTS

| | | |
|---|---|---|
| CN | 101137735 A | 3/2008 |
| CN | 102174078 A | 9/2011 |

(Continued)

OTHER PUBLICATIONS

Beaucage et al., "The Functionalization of Oligonucleotides Via Phosphoramidite Derivatives," *Tetrahedron* 49(10):1925-1963, 1993.
Chattopadhyay et al., "Brilliant Violet Fluorophores: A New Class of Ultrabright Fluorescent Compounds for Immunofluorescence Experiments," *Cytometry Part A* 81A:456-466, 2012.
Cuppoletti et al., "Oligomeric fluorescent labels for DNA," *Bioconjug. Chem.* 16(3):528-534, 2005.
Dioubankova et al., "Oligonucleotides containing new fluorescent 1-phenylethynylpyrene and 9,10-bis(phenylethynyl)anthracene uridine-2'-carbamates: synthesis and properties," *Tetrahedron* 60:4617-4626, 2004.
Dubrovsky, "Semiconductor nanoparticles as reporters in multiplexed immunoassay and cell analysis," *International Journal of Nanoscience* 8(1 & 2): 163-167, 2009.
Jain et al. "Current ADC Linker Chemistry," *Pharm. Res.* 32:3526-3540, 2015.

(Continued)

*Primary Examiner* — Jezia Riley
(74) *Attorney, Agent, or Firm* — Seed IP Law Group LLP

(57) ABSTRACT

Compositions comprising a polymeric dye and a cyclodextrin are provided. Methods associated with preparation and use of such compounds, for example in methods for detection of any analyte molecule, are also provided.

17 Claims, 4 Drawing Sheets

(56) References Cited

U.S. PATENT DOCUMENTS

| | | |
|---|---|---|
| 9,150,782 B2 | 10/2015 | Lee et al. |
| 9,400,273 B1 | 7/2016 | Liu et al. |
| 9,545,447 B2 | 1/2017 | Wooley et al. |
| 9,649,389 B2 | 5/2017 | Groves et al. |
| 9,687,291 B2 | 6/2017 | Shimizu et al. |
| 9,689,877 B2 | 6/2017 | Matray et al. |
| 9,765,220 B2* | 9/2017 | Matray ............... C09B 11/24 |
| 9,822,134 B2 | 11/2017 | Segev |
| 9,851,359 B2 | 12/2017 | Matray et al. |
| 9,884,070 B2 | 2/2018 | Denardo et al. |
| 9,913,992 B2 | 3/2018 | Demarest et al. |
| 10,036,754 B2 | 7/2018 | Matray et al. |
| 10,191,060 B2 | 1/2019 | Chiu et al. |
| 10,435,563 B2 | 10/2019 | Matray et al. |
| 10,709,791 B2 | 7/2020 | Stayton et al. |
| 10,865,310 B2 | 12/2020 | Matray et al. |
| 10,866,244 B2 | 12/2020 | Matray et al. |
| 10,954,391 B2 | 3/2021 | Matray et al. |
| 10,989,715 B2 | 4/2021 | Matray et al. |
| 11,084,932 B2 | 8/2021 | Battrell et al. |
| 11,142,647 B2 | 10/2021 | Matray et al. |
| 2001/0018503 A1 | 8/2001 | Whipple et al. |
| 2002/0099013 A1 | 7/2002 | Piccariello et al. |
| 2003/0054361 A1 | 3/2003 | Heller |
| 2003/0207208 A1 | 11/2003 | Uenishi |
| 2003/0207264 A1 | 11/2003 | Packard et al. |
| 2004/0014981 A1 | 1/2004 | Lugade et al. |
| 2004/0138467 A1 | 7/2004 | French et al. |
| 2004/0186278 A1 | 9/2004 | Chen et al. |
| 2004/0224372 A1 | 11/2004 | Li et al. |
| 2004/0241768 A1 | 12/2004 | Whitten et al. |
| 2005/0054024 A1 | 3/2005 | Lawrence |
| 2005/0123935 A1 | 6/2005 | Haugland et al. |
| 2006/0008822 A1 | 1/2006 | Manoharan et al. |
| 2006/0035302 A1 | 2/2006 | Lee |
| 2006/0063186 A1 | 3/2006 | Benson et al. |
| 2007/0042398 A1 | 2/2007 | Peng et al. |
| 2007/0077549 A1 | 4/2007 | Buller et al. |
| 2007/0148094 A1 | 6/2007 | Uzgiris |
| 2007/0269902 A1 | 11/2007 | Beechem et al. |
| 2008/0227939 A1 | 9/2008 | Mizoshita et al. |
| 2009/0253792 A1 | 10/2009 | Mickle et al. |
| 2009/0299070 A1 | 12/2009 | Berens et al. |
| 2010/0039684 A1 | 2/2010 | Kolb et al. |
| 2010/0092386 A1 | 4/2010 | Segev |
| 2010/0129800 A1 | 5/2010 | Aymami Bofarull et al. |
| 2010/0192312 A1 | 8/2010 | Cremer et al. |
| 2011/0224516 A1 | 9/2011 | Romey et al. |
| 2012/0021454 A1 | 1/2012 | Bikker et al. |
| 2012/0116079 A1 | 5/2012 | Lukhtanov et al. |
| 2012/0126175 A1 | 5/2012 | Ueno et al. |
| 2013/0059343 A1 | 3/2013 | Cheung |
| 2013/0102021 A1 | 4/2013 | Beacham et al. |
| 2013/0119363 A1 | 5/2013 | Sasaki et al. |
| 2013/0137755 A1 | 5/2013 | Segev |
| 2013/0202536 A1 | 8/2013 | Mustaev et al. |
| 2013/0244891 A1 | 9/2013 | Waggoner et al. |
| 2015/0110715 A1 | 4/2015 | Eder et al. |
| 2015/0159198 A1 | 6/2015 | McGall et al. |
| 2015/0232615 A1 | 8/2015 | Kwiatkowski |
| 2015/0258217 A1 | 9/2015 | Caravan |
| 2016/0039850 A1 | 2/2016 | Segev |
| 2016/0176903 A1 | 6/2016 | Segev |
| 2016/0264737 A1 | 9/2016 | Bartholomew et al. |
| 2016/0327859 A1 | 11/2016 | Idei et al. |
| 2016/0347907 A1 | 12/2016 | Dose |
| 2017/0326233 A1 | 11/2017 | Demeule et al. |
| 2018/0065998 A1 | 3/2018 | Battrell et al. |
| 2018/0079909 A1 | 3/2018 | Matray et al. |
| 2018/0163052 A1 | 6/2018 | Matray et al. |
| 2018/0164322 A1 | 6/2018 | Matray et al. |
| 2018/0237641 A1 | 8/2018 | Matray et al. |
| 2019/0016898 A1 | 1/2019 | Matray et al. |
| 2019/0144678 A1 | 5/2019 | Matray et al. |
| 2019/0153232 A1 | 5/2019 | Matray et al. |
| 2019/0177549 A1 | 6/2019 | Matray et al. |
| 2019/0300716 A1 | 10/2019 | Matray et al. |
| 2020/0109287 A1 | 4/2020 | Matray et al. |
| 2020/0222554 A1 | 7/2020 | Matray et al. |
| 2020/0284798 A1 | 9/2020 | Matray et al. |
| 2020/0353089 A1 | 11/2020 | Matray |
| 2020/0353094 A1 | 11/2020 | Matray |
| 2020/0360526 A1 | 11/2020 | Matray |
| 2020/0392345 A1 | 12/2020 | Matray et al. |
| 2021/0032277 A1 | 2/2021 | Matray et al. |
| 2021/0032474 A1 | 2/2021 | Matray et al. |
| 2021/0095130 A1 | 4/2021 | Matray et al. |
| 2021/0096135 A1 | 4/2021 | Matray et al. |
| 2021/0109104 A1 | 4/2021 | Jackson et al. |
| 2021/0128591 A1 | 5/2021 | Matray |
| 2021/0128739 A1 | 5/2021 | Matray |
| 2021/0253864 A1 | 8/2021 | Matray et al. |
| 2021/0261782 A1 | 8/2021 | Matray et al. |
| 2021/0285953 A1 | 9/2021 | Matray et al. |
| 2021/0340380 A1 | 11/2021 | Matray et al. |
| 2021/0395530 A1 | 12/2021 | Matray et al. |

FOREIGN PATENT DOCUMENTS

| | | |
|---|---|---|
| CN | 102971283 A1 | 3/2013 |
| CN | 103319378 A | 9/2013 |
| CN | 104072727 A | 10/2014 |
| CN | 106589005 A | 4/2017 |
| EP | 0 708 837 A1 | 5/1996 |
| EP | 1 650 269 A2 | 4/2006 |
| EP | 1 655 317 A1 | 5/2006 |
| EP | 2 366 785 A1 | 9/2011 |
| GB | 2 372 256 A | 8/2002 |
| GB | 2 456 298 A | 7/2009 |
| GB | 2 554 666 A | 4/2018 |
| JP | S61-207395 A | 9/1986 |
| JP | 4-282391 A | 10/1992 |
| JP | 2000-17183 A | 1/2000 |
| JP | 2000509412 A | 7/2000 |
| JP | 2008-510041 A | 4/2008 |
| JP | 2008-535945 A | 9/2008 |
| JP | 2009-519595 A | 5/2009 |
| JP | 2010-508295 A | 3/2010 |
| KR | 10-1041446 B1 | 6/2011 |
| KR | 10-2015-0007795 A | 1/2015 |
| SU | 1121931 A | 4/1988 |
| WO | 93/06482 A1 | 4/1993 |
| WO | 94/13688 A1 | 6/1994 |
| WO | 95/02700 A1 | 1/1995 |
| WO | 01/69254 A2 | 9/2001 |
| WO | 01/73123 A2 | 10/2001 |
| WO | 01/83502 A1 | 11/2001 |
| WO | 02/22883 A1 | 3/2002 |
| WO | 02/36832 A2 | 5/2002 |
| WO | 2006/020947 A2 | 2/2006 |
| WO | 2006/099050 A2 | 9/2006 |
| WO | 2009/015467 A1 | 2/2009 |
| WO | 2010/026957 A1 | 3/2010 |
| WO | 2013/012687 A2 | 1/2013 |
| WO | 2014/043289 A2 | 3/2014 |
| WO | 2014/102803 A1 | 7/2014 |
| WO | 2014/147642 A1 | 9/2014 |
| WO | 2014/159392 A1 | 10/2014 |
| WO | 2015/027176 A1 | 2/2015 |
| WO | 2015/109136 A2 | 7/2015 |
| WO | 2016/138461 A1 | 9/2016 |
| WO | 2016/183185 A1 | 11/2016 |
| WO | 2017/173348 A1 | 10/2017 |
| WO | 2017/177065 A2 | 10/2017 |
| WO | 2018/060722 A1 | 4/2018 |
| WO | 2019/071208 A1 | 4/2019 |
| WO | 2021/062176 A2 | 4/2021 |
| WO | 2021/067483 A1 | 4/2021 |

OTHER PUBLICATIONS

Kozma et al., "Fluorescent Ligands for Adenosine Receptors," *Bioorganic & Medicinal Chemistry Letters* 23: 26-36, 2013.

(56) References Cited

OTHER PUBLICATIONS

Leung et al., "7-Amino-4-Methyl-6-Sulfocoumarin-3-Acetic Acid: A Novel Blue Fluorescent Dye for Protein Labeling," *Bioorganic & Medicinal Chemistry Letters 9*: 2229-2232, 1999.

Li et al., "Polymeric Drugs: Advances in the development of pharmacologically active polymers," *Journal of Controlled Release 219*:360-382, 2015.

Luo et al., "Sensitive and rapid quantification of C-reactive protein using quantum dot-labeled microplate immunoassay," *Journal of Translational Medicine 10*(24):1-9, 2012.

Malakhov et al., "1-(Phenylethynyl)pyrene and 9,10-Bis(phenylethynyl)anthracene, Useful Fluorescent Dyes for DNA Labeling: Excimer Formation and Energy Transfer," *Eur. J. Org. Chem*: 1298-1307, 2004.

Paris et al., "Probing DNA sequences in solution with a monomer-excimer fluorescence color change," *Nucleic Acids Research 26*(16):3789-3793, 1998.

Petreus et al., "Polyester imides containing main-chain phosphorus," *Revue Roumaine de Chimie 34*(8):971-978, 1994 (with English Abstract).

Ren et al., "An Antisense Oligodeoxynucleotide-Doxorubicin Conjugate: Preparation and Its Reversal Multidrug Resistance of Human Carcinoma Cell Line In Vitro," *Nucleosides, Nucleotides & Nucleic Acids 23*(10):1595-1607, 2004.

RN 230952-79-1, Registry Database Compound, 1999.

Singh et al., "Multiplexed measurement of membrane protein populations," *Caplus 2003*:769075, 2003. (2 pages).

Stuart et al., "Site-Specific DNA-Doxorubicin Conjugates Display Enhanced Cytotoxicity to Breast Cancer Cells," *Bioconjugate Chemistry 25*:406-413, 2014.

Teo et al., "Polyfluorophores on a DNA Backbone: A Multicolor Set of Labels Excited at One Wavelength," *J. Am. Chem. Soc. 131*(11):3923-3933, 2009. (NIH Public Access Author Manuscript, available in PMC Mar. 25, 2010, 23 pages).

Tram et al., "Oligonucleotide Labeling Using BODIPY Phosphoramidite," *Nucleosides, Nucleotides & Nucleic Acids 30*(1):1-11, 2011.

"What is an Analyte?," Google Search, dated Mar. 22, 2018, retrieved from https://www.google.com/search?q=what+is+an+analyte&rlz=1C1GCEB_enUS775US775&oq=what+is+an+analyte&aqs=chrome..69i57j0I5.3232ljOj7&s. . . 2 pages.

Arian et al., "1,9-Dialkoxyanthracene as a 1O2-Sensitive Linker," *J. Am. Chem. Soc. 133*:3912-3980, 2011.

Babitskaya et al., "Bromoacyl Analogues of Phosphatidylcholine with Intramolecular Fluorescence Quenching and Their Use as Substrates for Continuous Monitoring of Phospholipase A2 Activity," *Applied Biochemistry and Microbiology 40*(4):351-356, 2004.

Becker et al., "New Thermotropic Dyes on Amino-Subsituted Perylendicarboximides," *Chem. Eur. J. 6*(21):3984-3990, 2000.

Bergstrom et al., "A NaPi2b Antibody-Drug Conjugate Induces Durable Complete Tumor Regressions in Patient-Derived Xenograft Models of NSCLC," *IASLC 17th World Conference on Lung Cancer*, Vienna, Austria, Dec. 4-7, 2016. (8 pages).

Bergstrom et al., "A novel, highly potent HER2-targeted antibody-drug conjugate (ADC) for the treatment of low HER2-expressing tumors and combination with trastuzumab-based regimens in HER2-driven tumors," Mersana Therapeutics, Abstract LBA-231, 2015, 1 page.

Bergstrom et al., "Potent Promise," *Innovations in Pharmaceutical Technology 49*:16-20, 2014.

Bergstrom et al., "XMT-1522 induces tumor regressions in preclinical models representing HER2-positive and HER2 low-expressing breast cancer," Mersana Therapeutics, Abstract P4-14-28, 2015, 1 page.

Braeckmans et al., "Three-dimensional fluorescence recovery after photobleaching with the confocal scanning laser microscope," *Biophysical Journal 85*:2240-2252, 2003.

Braga et al., "Intracellular macromolecular mobility measured by fluorescence recovery after photobleaching with confocal laser scanning microscopes," *Molecular Biology of the Cell 15*:4749-4760, 2004.

Brinkley, "A brief survey of methods for preparing protein conjugates with dyes, haptens and crosslinking reagents," *Bioconjugate Chem 3*:2-13, 1992.

CAPLUS Accession No. 1975: 171341, Holy, "Nucleic acid components and their analogs. CLXXII. Aliphatic analogs of nucleosides, nucleotides, and oligonucleotides," Collection of Czechoslovak Chemical Communications 40(1):187-214, 1975. (1 page).

Chong et al., "Oxygen Quenching of Pyrene-Lipid Fluorescence in Phosphatidylcholine Vesicles—A Probe for Membrane Organization," *Biophys. J. 47*:613-621, 1985.

Dai et al., "DNA-polyfluorophore excimers as sensitive reporters for esterases and lipases," *Chemical Communications 46*(8): 1221, 2010.

Divittorio et al., "Synthetic peptides with selective affinity for apoptotic cells," *Organic & Biomolecular Chemistry 4*(10): 1966, 2006.

Gao et al., "Libraries of Composite Polyfluors Built from Fluorescent Deoxyribosides," *Jorunal of the American Chemical Society 124*(39): 11590-11591, 2002.

Gao et al., "Modified DNA Analogues That Sense Light Exposure with Color Change," *Journal of the American Chemical Society 126*(40):12748-12749, 2004.

Gordon et al., "Analysis of simulated and experimental fluorescence recovery after photobleaching. Data for two diffusing components," *Biophysical Journal 68*:766-778, 1995.

Hanhela et al., "Synthesis and evaluation of fluorescent materials for colour control of peroxyoxalate chemiluminescence. II. Violet and blue emitters," *Australian Journal of Chemistry 34*(8):1701-1717, 1981.

Haraguchi, "Live Cell Imaging: Approaches for Studying Protein Dynamics in Living Cells," *Cell Structure And Function 27*:333-334, 2002.

Koo et al., "Fluorescent DNA chemosensors: identification of bacterial species by their volatile metabolites," *Chemical Communications 47*(41):11435, 2011.

Lee et al., "Monitoring the Hydrophobic Interactions of Internally Pyrene-Labeled Poly(ethylene oxides)s in Water by Fluorescence Spectroscopy," *Macromolecules 31*:9193-9200, 1998.

Liu et al., "Detection of prostate-specific membrane antigen on HUVECs in response to breast tumor-conditioned medium," *International Journal of Oncology 38*:1349-1355, 2011.

Liu et al., "DNA-Based Micelles: Synthesis, Micellar Properties and Size-Dependent Cell Permeability," *Chem. Eur. J. 16*:3791-3797, 2010. (14 Pages).

Mersana Therapeutics, URL=http://www.mersana.com, download date Jan. 3, 2019, 9 pages.

Molotkovsky et al., "Perylenoyl- and Anthrylvinyl-Labeled Lipids as Membrane Probes," *Biochimica et Biophysica Acta 778*:281-288, 1984.

Nussbaumer et al., "Amplification of Chirality by Supramolecular Polymerization of Pyrene Oligomers," *Angewandte Chemie International Edition 50*(24):5490-5494, 2011.

Pownall et al., "Kinetics of Spontaneous and Plasma-Stimulated Sphingomyelin Transfer," *Biochimica et Biophysica Acta 712*:169-176, 1982.

Pubchem, "US20100012929A1-20100121-C00010_4," SID No. 140452858, retrieved Mar. 29, 2016 from URL https://pubchem.ncbi.nlm.nih.gov/substance/140452858, 6 pages.

Wang et al., "Cruciforms: Assembling Single Crystal Micro- and Nanostructures from One to Three Dimensions and Their Applications in Organic Field-Effect Transistors," *Chem. Mater. 21*:2840-2845, 2009.

Wang et al., "DNA Polyfluorophores for Real-Time Multicolor Tracking of Dynamic Biological Systems," *Angewandte Chemie Biological Systems 51*(29):7176-7180, 2012.

Wilson et al., "Efficient Quenching of Oligomeric Fluorophores on a DNA Backbone," *Journal of the American Chemical Society 129*(50):15426-15427, 2007.

(56) References Cited

OTHER PUBLICATIONS

Wilson et al., "Oligodeoxyfluorosides: Strong Sequence of Dependence of Fluorescence Emission," *Tetrahedron* 63(17):3427-3433, 2007. (18 Pages).
Yurkovetskiy et al., "Advantages of Polyacetal Polymer-based Antibody Drug Conjugates: Application to Low Expression Targets," Mersana Therapeutics, technical paper #2645, 2014, 1 page.
Avirah et al., "Infrared Absorbing Croconaine Dyes: Synthesis and Metal Ion Binding Properties," *J. Org. Chem.* 73(1):274-279, 2008.
Li et al., "Responsive nanogel-based dual fluorescent sensors for temperature and $Hg^{2+}$ ions with enhanced detection sensitivity," *J. Mater. Chem.* 20:10716-10723, 2010.
Stewart et al., "The Fluorescence of a Chelating Two-Photon-Absorbing Dye is Enhanced with the Addition of Transition Metal Ions but Quenched in the Presence of Acid," *Proc. Of SPIE* 9939(993904):1-10, 2016.
Zhang et al., "FRET Imaging of Enzyme-Responsive HPMA Copolymer Conjugate," *Macromolecular Bioscience* 17(1600125):1-8, 2017.
Doi et al., "Hetero-Selective DNA-Like Duplex Stabilized by Donor-Acceptor Interactions," *Chem. Eur. J.* 21:15974-15980, 2015.
Franceschin et al., "Synthesis of a Dibromoperylene Phosphoramidite Building Block and Its Incorporation at the 5' End of a G-Quadruplex Forming Oligonucleotide: Spectroscopic Properties and Structural Studies of the Resulting Dibromoperylene Conjugate," *Bioconjugate Chem* 22:1309-1319, 2011.
Johansson, "Choosing Reporter-Quencher Pairs for Efficient Quenching Through Formation of Intramolecular Dimers," *Methods in Molecular Biology* 335:17-29, 2006.
Masuko et al., "Fluorescence resonance energy transfer from pyrene to perylene labels for nucleic acid hybridization assays under homogenous solution conditions," *Nucleic Acids Research* 28(8):e34, 2000 (8 pages).
Saito et al., "Dual-labeled oligonucleotide probe for sensing adenosine via FRET: A novel alternative to SNPs genotyping," *Chem. Commun.*:2133-2135, 2007.
Takakusa et al., "Design and Synthesis of an Enzyme-Cleavable Sensor Molecule for Phosphodiesterase Activity Based on Fluorescence Resonance Energy Transfer," *J. Am. Chem. Soc.* 124(8):1653-1651, 2002.
Vinogradov et al., "Total synthesis and biochemical characterization of mirror image barnase," *Chem Sci.* 6: 2997-3002, 2015.
Aviñó et al., "Solid-phase synthesis of oligomers carrying several chromophore units linked by phosphodiester backbones," *Bioorganic & Medicinal Chemistry Letters* 18:2306-2310, 2008.
Boldyrev et al., "Synthesis and Characteristics of New Fluorescent Probes Based on Cardiolipin," *Russian Journal of Bioorganic Chemistry* 35(2):219-224, 2009.
Buckhout-White et al., "Assembling programmable FRET-based photonic networks using designer DNA scaffolds," *Nature Communications* 5:5615, Dec. 11, 2014. (16 pages).
De Vos et al., "New Non Nucleosidic Phosphoramidites for the Solid Phase Multi-Labelling of Oligonucleotides: Comb- and Multifork-Like Structures," *Nucleosides & Nucleotides* 13(10):2245-2265, 1994.
Guryev et al., "Control of the Fluorescence of Dye-Antibody Conjugates by (2-Hydroxypropyl)-β-cyclodextrin in Fluorescence Microscopy and Flow Cytometry," *Analytical Chemistry* 83:7109-7114, Aug. 16, 2011.
Kashida et al., "A Cationic Dye Triplet as a Unique "Glue" That Can Connect Fully Matched Termini of DNA Duplexes," *Chem. Eur. J.* 17:2614-2622, 2011.
Kozytska et al., "Discovery of the novel, homogeneous payload platform Dolasynthen for Antibody-Drug Conjugates," Mersana Therapeutics, Cambridge, MA, 2018 (1 page).
Phares et al., "Improving the Stability and Sensing of Electrochemical Biosensors by Employing Trithiol-Anchoring Groups in a Six-Carbon Self-Assembled Monolayer," *Anal. Chem.* 81(3):1095-1100, Feb. 1, 2009.
Vybornyi et al., "Formation of Two-Dimensional Supramolecular Polymers by Amphiphilic Pyrene Oligomers," *Angew. Chem. Int. Ed.* 52:114488-11493, 2013.
Wang et al., "Fluorescence-Based Evaluation of the Partitioning of Lipids and Lipidated Peptides into Liquid-Ordered Lipid Microdomains: A Model for Molecular Partitioning into Lipid Rafts," *Biophysical Journal* 79:919-933, Aug. 2000.
CAS Registry No. 862288-26-4, American Chemical Society, 2021. (1 page).
Damian et al., "Synthesis and DNA Interaction of Platinum Complex/Peptide Chimera as Potential Drug Candidates," *Eur. J. Org Chem.* 6161-6170, 2010.
Drescher et al., "General Synthesis and Aggregation Behaviour of New Single-Chain Bolaphospholipids: Variations in Chain and Headgroup Structures," *Chemistry—A European Journal* 14(22):6796-6804, 2008.
Lewis et al., "Orientation Control of Fluorescence Resonance Energy Transfer Using DNA as a Helical Scaffold," *J. Am. Chem. Soc.* 127(28):10002-10003, 2005.
Rochat et al., "Water-Soluble Cationic Conjugated Polymers: Response to Electron-Rich Bioanalytes," *J. Am. Chem. Soc.* 135:17703-17706, 2013.
Sun et al., "Dual-Color Fluorescence Imaging of Magnetic Nanoparticles in Live Cancer Cells Using Conjugated Polymer Probes," *Scientific Reports* 6:22368, 2016. (12 pages).
Sun et al., "High yield production of high molecular weight poly(ethylene glycol)/ α-cyclodextrin polyrotaxanes by aqueous one-pot approach," *Polymer* 53:2884-2889, 2012.
Sun et al., "Ultrabright and Multicolorful Fluorescence of Amphiphilic Polyethyleneimine Polymer Dots for Efficiently Combined Imaging and Therapy," *Scientific Reports* 3:3036, 2013. (6 pages).
Teyssot et al., "Aromatic Nitrogen Donors for Efficient Copper(1)-NHC CuAAC under Reductant-Free Conditions," *Eur. J. Org Chem.* 3507-3515, 2010.
Winiger et al., "Long-Distance Electronic Energy Transfer in Light-Harvesting Supramolecular Polymers," *Angew. Chem. Int. Ed.* 53:13609-13613, 2014.
Zhao et al., "Mussel-Inspired One-Pot Synthesis of a Fluorescent and Water-Soluble Polydopamine-Polyethyleneimine Copolymer," *Macromol. Rapid Commun.* 36:909-915, 2015.

* cited by examiner

COMPOSITIONS COMPRISING A POLYMERIC DYE AND A CYCLODEXTRIN AND USES THEREOF

BACKGROUND

Field

Embodiments of the present invention are generally directed to dimeric and polymeric fluorescent or colored dyes, and methods for their preparation and use in various analytical methods.

Description of the Related Art

Fluorescent and/or colored dyes are known to be particularly suitable for applications in which a highly sensitive detection reagent is desirable. Dyes that are able to preferentially label a specific ingredient or component in a sample enable the researcher to determine the presence, quantity and/or location of that specific ingredient or component. In addition, specific systems can be monitored with respect to their spatial and temporal distribution in diverse environments.

Fluorescence and colorimetric methods are extremely widespread in chemistry and biology. These methods give useful information on the presence, structure, distance, orientation, complexation and/or location for biomolecules. In addition, time-resolved methods are increasingly used in measurements of dynamics and kinetics. As a result, many strategies for fluorescence or color labeling of biomolecules, such as nucleic acids and protein, have been developed. Since analysis of biomolecules typically occurs in an aqueous environment, the focus has been on development and use of water soluble dyes.

Highly fluorescent or colored dyes are desirable since use of such dyes increases the signal to noise ratio and provides other related benefits. Accordingly, attempts have been made to increase the signal from known fluorescent and/or colored moieties. For example, dimeric and polymeric compounds comprising two or more fluorescent and/or colored moieties have been prepared in anticipation that such compounds would result in brighter dyes. However, as a result of intramolecular fluorescence quenching, the known dimeric and polymeric dyes have not achieved the desired increase in brightness.

There is thus a need in the art for water soluble dyes having an increased molar brightness. Ideally, such dyes and biomarkers should be intensely colored or fluorescent and should be available in a variety of colors and fluorescent wavelengths. The present invention fulfills this need and provides further related advantages.

BRIEF SUMMARY

In brief, embodiments of the present invention are generally directed to compositions comprising a polymeric dye and a cyclodextrins and use of such compositions for detection of various analytes, such as biomolecules. Without wishing to be bound by theory, it is believed that the cyclodextrin in the composition binds to one or more dye moieties in the polymeric dye and prevents or reduces intramolecular quenching of the signal (e.g., fluorescent signal) from the dye moiety. Accordingly, the presently disclosed compositions have a higher molar brightness relative to compositions of polymeric dyes without a cyclodextrin.

The compositions of embodiments of the invention are intensely colored and/or fluorescent and can be readily observed by visual inspection or other means. In some embodiments the compositions may be observed without prior illumination or chemical or enzymatic activation.

In one embodiment is provided a composition comprising a polymeric dye and a cyclodextrin, the polymeric dye comprising two or more dye moieties M covalently linked by a linker L. In some embodiments, the polymeric dye is a compound of structure (I), (II), (III) or (IV). The disclosed compositions find utility in a number of applications, including use as fluorescent and/or colored dyes in various analytical methods.

In another embodiment, a method for staining a sample is provided, the method comprises adding to said sample the composition comprising a polymeric dye and a cyclodextrin in an amount sufficient to produce an optical response when said sample is illuminated at an appropriate wavelength.

In still other embodiments, the present disclosure provides a method for visually detecting an analyte molecule, comprising:
  (a) providing a composition comprising a polymeric dye, a cyclodextrin and the analyte molecule; and
  (b) detecting the polymeric dye by its visible properties.

Other disclosed methods include a method for visually detecting a biomolecule, the method comprising:
  (a) admixing the composition comprising a polymeric dye and a cyclodextrin with one or more biomolecules; and
  (b) detecting the polymeric dye by its visible properties.

Other embodiments provide a method for visually detecting an analyte, the method comprising:
  (a) providing a composition as disclosed herein, wherein the polymeric dye comprises a linker comprising a covalent bond to a targeting moiety having specificity for the analyte;
  (b) admixing the composition and the analyte, thereby associating the targeting moiety and the analyte; and
  (c) detecting the polymeric dye by its visible properties.

Use of the disclosed compositions in analytical methods for detection of the one or more analyte molecule, such as a biomolecule is also provided.

Still different embodiments provide a compound of structure (I), (II), (III) or (IV).

These and other aspects of the invention will be apparent upon reference to the following detailed description.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1:
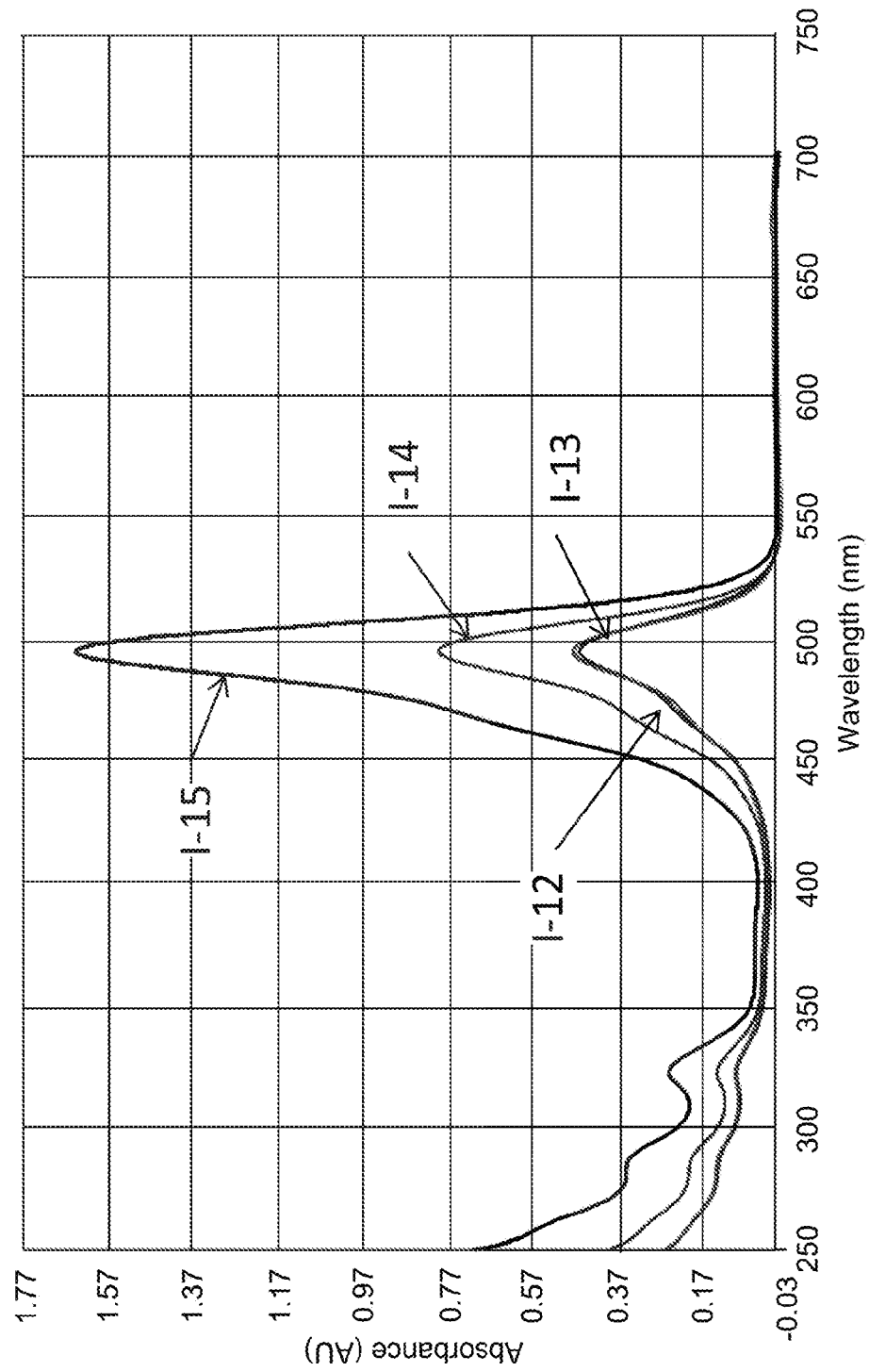
FIG. 1 provides UV absorbance data for polymeric dyes.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —NH$_2$ group.
"Carboxy" refers to the —CO$_2$H group.
"Cyano" refers to the —CN group.
"Formyl" refers to the —C(=O)H group.
"Hydroxy" or "hydroxyl" refers to the —OH group.
"Imino" refers to the =NH group.
"Nitro" refers to the —NO$_2$ group.
"Oxo" refers to the =O substituent group.
"Sulfhydryl" refers to the —SH group.
"Thioxo" refers to the =S group.

"Alkyl" refers to a straight or branched hydrocarbon chain group consisting solely of carbon and hydrogen atoms, containing no unsaturation, having from one to twelve carbon atoms (C$_1$-C$_{12}$ alkyl), one to eight carbon atoms (C$_1$-C$_8$ alkyl) or one to six carbon atoms (C$_1$-C$_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, alkyl groups are optionally substituted.

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, alkylene is optionally substituted.

"Alkenylene" or "alkenylene chain" refers to a straight or branched divalent hydrocarbon chain linking the rest of the molecule to a radical group, consisting solely of carbon and hydrogen, containing at least one carbon-carbon double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, alkenylene is optionally substituted.

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms, e.g., ethenylene, propenylene, n-butenylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, alkynylene is optionally substituted.

"Alkylether" refers to any alkyl group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylethers include at least one carbon oxygen bond, but may include more than one. For example, polyethylene glycol (PEG) is included within the meaning of alkylether. Unless stated otherwise specifically in the specification, an alkylether group is optionally substituted. For example, in some embodiments an alkylether is substituted with an alcohol or —OP(=R$_a$)(R$_b$)R$_c$, wherein each of R$_a$, R$_b$ and R$_c$ is as defined for compounds of structure (I).

"Alkoxy" refers to a group of the formula —OR$_a$ where R$_a$ is an alkyl group as defined above containing one to twelve carbon atoms. Unless stated otherwise specifically in the specification, an alkoxy group is optionally substituted.

"Alkoxyalkylether" refers to a group of the formula —OR$_a$R$_b$ where R$_a$ is an alkylene group as defined above containing one to twelve carbon atoms, and Rb is an alkylether group as defined herein. Unless stated otherwise specifically in the specification, an alkoxyalkylether group is optionally substituted, for example substituted with an alcohol or —OP(=R$_a$)(R$_b$)R$_c$, wherein each of R$_a$, R$_b$ and R$_c$ is as defined for compounds of structure (I).

"Heteroalkyl" refers to an alkyl group, as defined above, comprising at least one heteroatom (e.g., N, O, P or S) within the alkyl group or at a terminus of the alkyl group. In some embodiments, the heteroatom is within the alkyl group (i.e., the heteroalkyl comprises at least one carbon-[heteroatom]$_x$-carbon bond, where x is 1, 2 or 3). In other embodiments, the heteroatom is at a terminus of the alkyl group and thus serves to join the alkyl group to the remainder of the molecule (e.g., M1-H-A), where M1 is a portion of the molecule, H is a heteroatom and A is an alkyl group). Unless stated otherwise specifically in the specification, a heteroalkyl group is optionally substituted. Exemplary heteroalkyl groups include ethylene oxide (e.g., polyethylene oxide), optionally including phosphorous-oxygen bonds, such as phosphodiester bonds.

"Heteroalkoxy" refers to a group of the formula —OR$_a$ where R$_a$ is a heteroalkyl group as defined above containing one to twelve carbon atoms. Unless stated otherwise specifically in the specification, a heteroalkoxy group is optionally substituted.

"Heteroalkylene" refers to an alkylene group, as defined above, comprising at least one heteroatom (e.g., N, O, P or S) within the alkylene chain or at a terminus of the alkylene chain. In some embodiments, the heteroatom is within the alkylene chain (i.e., the heteroalkylene comprises at least one carbon-[heteroatom]$_x$-carbon bond, where x is 1, 2 or 3). In other embodiments, the heteroatom is at a terminus of the alkylene and thus serves to join the alkylene to the remainder of the molecule (e.g., M1-H-A-M2, where M1 and M2 are portions of the molecule, H is a heteroatom and A is an alkylene). Unless stated otherwise specifically in the specification, a heteroalkylene group is optionally substituted. An exemplary heteroalkylene linking group includes ethylene oxide and the linker illustrated below:

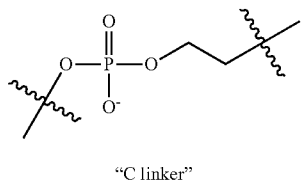 [SMILES: *CCOP(=O)([O-])O*]

"C linker"

Multimers of the above C-linker are included in various embodiments of heteroalkylene linkers.

"Heteroalkenylene" is a heteroalkylene, as defined above, comprising at least one carbon-carbon double bond. Unless stated otherwise specifically in the specification, a heteroalkenylene group is optionally substituted.

"Heteroalkynylene" is a heteroalkylene comprising at least one carbon-carbon triple bond. Unless stated otherwise specifically in the specification, a heteroalkynylene group is optionally substituted.

"Heteroatomic" in reference to a "heteroatomic linker" refers to a linker group consisting of one or more heteroatoms. Exemplary heteroatomic linkers include single atoms selected from the group consisting of O, N, P and S, and multiple heteroatoms for example a linker having the formula —P(O$^-$)(=O)O— or —OP(O$^-$)(=O)O— and multimers and combinations thereof.

"Phosphate" refers to the —OP(=O)(R$_a$)R$_b$ group, wherein R$_a$ is OH, O$^-$ or OR$_c$; and R$_b$ is OH, O$^-$, OR$_c$, a thiophosphate group or a further phosphate group, wherein R$_c$ is a counter ion (e.g., Na+ and the like).

"Phosphoalkyl" refers to the —OP(=O)(R$_a$)R$_b$ group, wherein R$_a$ is OH, O$^-$ or OR$_c$; and R$_b$ is —Oalkyl, wherein R$_c$ is a counter ion (e.g., Na+ and the like). Unless stated otherwise specifically in the specification, a Phosphoalkyl group is optionally substituted. For example, in certain embodiments, the —Oalkyl moiety in a phosphoalkyl group is optionally substituted with one or more of hydroxyl, amino, sulfhydryl, phosphate, thiophosphate, phosphoalkyl, thiophosphoalkyl, phosphoalkylether, thiophosphoalkylether, or —OP(=R$_a$)(R$_b$)R$_c$, wherein each of R$_a$, R$_b$ and R$_c$ is as defined for structure (I).

"Phosphoalkylether" refers to the —OP(=O)(R$_a$)R$_b$ group, wherein R$_a$ is OH, O$^-$ or OR$_c$; and R$_b$ is —Oalkylether, wherein R$_c$ is a counter ion (e.g., Na+ and the like). Unless stated otherwise specifically in the specification, a phosphoalkylether group is optionally substituted. For example, in certain embodiments, the —Oalkylether moiety in a phosphoalkylether group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)R$_c$, wherein each of R$_a$, R$_b$ and R$_c$ is as defined for structure (I).

"Thiophosphate" refers to the —OP(=R$_a$)(R$_b$)R$_c$ group, wherein R$_a$ is O or S, R$_b$ is OH, O$^-$, S$^-$, OR$_d$ or SR$_d$; and R$_c$ is OH, SH, O$^-$, S$^-$, OR$_d$, SR$_d$, a phosphate group or a further thiophosphate group, wherein R$_d$ is a counter ion (e.g., Na+ and the like) and provided that: i) R$_a$ is S; ii) R$_b$ is S$^-$ or SR$_d$; iii) R$_c$ is SH, S$^-$ or SR$_d$; or iv) a combination of i), ii) and/or iii).

"Thiophosphoalkyl" refers to the —OP(=R$_a$)(R$_b$)R$_c$ group, wherein R$_a$ is O or S, R$_b$ is OH, O$^-$, S$^-$, OR$_d$ or SR$_d$; and R$_c$ is —Oalkyl, wherein R$_d$ is a counter ion (e.g., Na+ and the like) and provided that: i) R$_a$ is S; ii) R$_b$ is S$^-$ or SR$_d$; or iii) R$_a$ is S and R$_b$ is S$^-$ or SR$_d$. Unless stated otherwise specifically in the specification, a thiophosphoalkyl group is optionally substituted. For example, in certain embodiments, the —Oalkyl moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)R$_c$, wherein each of R$_a$, R$_b$ and R$_c$ is as defined for structure (I).

"Thiophosphoalkylether" refers to the —OP(=R$_a$)(R$_b$)R$_c$ group, wherein R$_a$ is O or S, R$_b$ is OH, O$^-$, S$^-$, OR$_d$ or SR$_d$; and R$_c$ is —Oalkylether, wherein R$_d$ is a counter ion (e.g., Na+ and the like) and provided that: i) R$_a$ is S; ii) R$_b$ is S$^-$ or SR$_d$; or iii) R$_a$ is S and R$_b$ is S$^-$ or SR$_d$. Unless stated otherwise specifically in the specification, a thiophosphoalkylether group is optionally substituted. For example, in certain embodiments, the —Oalkylether moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)R$_c$, wherein each of R$_a$, R$_b$ and R$_c$ is as defined for structure (I).

"Carbocyclic" refers to a stable 3- to 18-membered aromatic or non-aromatic ring comprising 3 to 18 carbon atoms. Unless stated otherwise specifically in the specification, a carbocyclic ring may be a monocyclic, bicyclic, tricyclic or tetracyclic ring system, which may include fused or bridged ring systems, and may be partially or fully saturated. Non-aromatic carbocyclyl radicals include cycloalkyl, while aromatic carbocyclyl radicals include aryl. Unless stated otherwise specifically in the specification, a carbocyclic group is optionally substituted.

"Cycloalkyl" refers to a stable non-aromatic monocyclic or polycyclic carbocyclic ring, which may include fused or bridged ring systems, having from three to fifteen carbon atoms, preferably having from three to ten carbon atoms, and which is saturated or unsaturated and attached to the rest of the molecule by a single bond. Monocyclic cyclocalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo-[2.2.1]heptanyl, and the like. Unless stated otherwise specifically in the specification, a cycloalkyl group is optionally substituted.

"Aryl" refers to a ring system comprising at least one carbocyclic aromatic ring. In some embodiments, an aryl comprises from 6 to 18 carbon atoms. The aryl ring may be a monocyclic, bicyclic, tricyclic or tetracyclic ring system, which may include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted.

"Heterocyclic" refers to a stable 3- to 18-membered aromatic or non-aromatic ring comprising one to twelve carbon atoms and from one to six heteroatoms selected from the group consisting of nitrogen, oxygen and sulfur. Unless stated otherwise specifically in the specification, the heterocyclic ring may be a monocyclic, bicyclic, tricyclic or tetracyclic ring system, which may include fused or bridged ring systems; and the nitrogen, carbon or sulfur atoms in the heterocyclic ring may be optionally oxidized; the nitrogen atom may be optionally quaternized; and the heterocyclic ring may be partially or fully saturated. Examples of aromatic heterocyclic rings are listed below in the definition of heteroaryls (i.e., heteroaryl being a subset of heterocyclic). Examples of non-aromatic heterocyclic rings include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclic group is optionally substituted.

"Heteroaryl" refers to a 5- to 14-membered ring system comprising one to thirteen carbon atoms, one to six heteroatoms selected from the group consisting of nitrogen, oxygen and sulfur, and at least one aromatic ring. For purposes of certain embodiments of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). Unless stated otherwise specifically in the specification, a heteroaryl group is optionally substituted.

"Fused" refers to a ring system comprising at least two rings, wherein the two rings share at least one common ring atom, for example two common ring atoms. When the fused ring is a heterocyclyl ring or a heteroaryl ring, the common ring atom(s) may be carbon or nitrogen. Fused rings include bicyclic, tricyclic, tetracyclic, and the like.

The term "substituted" used herein means any of the above groups (e.g., alkyl, alkylene, alkenylene, alkynylene, heteroalkylene, heteroalkenylene, heteroalkynylene, alkoxy, alkylether, alkoxyalkylether, heteroalkyl, heteroalkoxy, phosphoalkyl, phosphoalkylether, thiophosphoalkyl, thiophosphoalkylether, carbocyclic, cycloalkyl, aryl, heterocyclic and/or heteroaryl) wherein at least one hydrogen atom (e.g., 1, 2, 3 or all hydrogen atoms) is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In some embodiments, the optional substituent is —$OP(=R_a)(R_b)R_c$, wherein each of $R_a$, $R_b$ and $R_c$ is as defined for structure (I). In addition, each of the foregoing substituents may also be optionally substituted with one or more of the above substituents.

"Conjugation" refers to the overlap of one p-orbital with another p-orbital across an intervening sigma bond. Conjugation may occur in cyclic or acyclic compounds. A "degree of conjugation" refers to the overlap of at least one p-orbital with another p-orbital across an intervening sigma bond. For example, 1,3-butadine has one degree of conjugation, while benzene and other aromatic compounds typically have multiple degrees of conjugation. Fluorescent and colored compounds typically comprise at least one degree of conjugation.

"Fluorescent" refers to a molecule which is capable of absorbing light of a particular frequency and emitting light of a different frequency. Fluorescence is well-known to those of ordinary skill in the art.

"Colored" refers to a molecule which absorbs light within the colored spectrum (i.e., red, yellow, blue and the like).

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions.

The term "biomolecule" refers to any of a variety of biological materials, including nucleic acids, carbohydrates, amino acids, polypeptides, glycoproteins, hormones, aptamers and mixtures thereof. More specifically, the term is intended to include, without limitation, RNA, DNA, oligonucleotides, modified or derivatized nucleotides, enzymes, receptors, prions, receptor ligands (including hormones), antibodies, antigens, and toxins, as well as bacteria, viruses, blood cells, and tissue cells. The visually detectable biomolecules of the invention (e.g., compounds of structure (I) having a biomolecule linked thereto) are prepared, as further described herein, by contacting a biomolecule with a compound having a reactive group that enables attachment of the biomolecule to the compound via any available atom or functional group, such as an amino, hydroxy, carboxyl, or sulfhydryl group on the biomolecule.

A "reactive group" is a moiety capable of reacting with a second reactive groups (e.g., a "complementary reactive group") to form one or more covalent bonds, for example by a displacement, oxidation, reduction, addition or cycloaddition reaction. Exemplary reactive groups are provided in Table 1, and include for example, nucleophiles, electrophiles, dienes, dienophiles, aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin, thiirane and the like.

The terms "visible" and "visually detectable" are used herein to refer to substances that are observable by visual inspection, without prior illumination, or chemical or enzymatic activation. Such visually detectable substances absorb and emit light in a region of the spectrum ranging from about 300 to about 900 nm. Preferably, such substances are intensely colored, preferably having a molar extinction coefficient of at least about 40,000, more preferably at least about 50,000, still more preferably at least about 60,000, yet still more preferably at least about 70,000, and most preferably at least about 80,000 $M^{-1}$ $cm^{-1}$. The compounds of the invention may be detected by observation with the naked eye, or with the aid of an optically based detection device, including, without limitation, absorption spectrophotometers, transmission light microscopes, digital cameras and scanners. Visually detectable substances are not limited to those which emit and/or absorb light in the visible spectrum. Substances which emit and/or absorb light in the ultraviolet (UV) region (about 10 nm to about 400 nm), infrared (IR) region (about 700 nm to about 1 mm), and substances emitting and/or absorbing in other regions of the electromagnetic spectrum are also included with the scope of "visually detectable" substances.

For purposes of embodiments of the invention, the term "photostable visible dye" refers to a chemical moiety that is visually detectable, as defined hereinabove, and is not significantly altered or decomposed upon exposure to light. Preferably, the photostable visible dye does not exhibit significant bleaching or decomposition after being exposed to light for at least one hour. More preferably, the visible dye is stable after exposure to light for at least 12 hours, still more preferably at least 24 hours, still yet more preferably at least one week, and most preferably at least one month. Nonlimiting examples of photostable visible dyes suitable for use in the compounds and methods of the invention include azo dyes, thioindigo dyes, quinacridone pigments, dioxazine, phthalocyanine, perinone, diketopyrrolopyrrole, quinophthalone, and truarycarbonium.

As used herein, the term "perylene derivative" is intended to include any substituted perylene that is visually detectable. However, the term is not intended to include perylene itself. The terms "anthracene derivative", "naphthalene derivative", and "pyrene derivative" are used analogously. In some preferred embodiments, a derivative (e.g., perylene, pyrene, anthracene or naphthalene derivative) is an imide, bisimide or hydrazamimide derivative of perylene, anthracene, naphthalene, or pyrene.

The visually detectable molecules of various embodiments of the invention are useful for a wide variety of analytical applications, such as biochemical and biomedical applications, in which there is a need to determine the presence, location, or quantity of a particular analyte (e.g., biomolecule). In another aspect, therefore, the invention provides a method for visually detecting a biomolecule, comprising: (a) providing a biological system with a visually detectable biomolecule comprising the compound of structure (I) linked to a biomolecule; and (b) detecting the biomolecule by its visible properties. For purposes of embodiments of the invention, the phrase "detecting the biomolecule by its visible properties" means that the biomolecule, without illumination or chemical or enzymatic activation, is observed with the naked eye, or with the aid of a optically based detection device, including, without limitation, absorption spectrophotometers, transmission light microscopes, digital cameras and scanners. A densitometer may be used to quantify the amount of visually detectable biomolecule present. For example, the relative quantity of the biomolecule in two samples can be determined by measuring relative optical density. If the stoichiometry of dye molecules per biomolecule is known, and the extinction coefficient of the dye molecule is known, then the absolute concentration of the biomolecule can also be determined from a measurement of optical density. As used herein, the term "biological system" is used to refer to any solution or mixture comprising one or more biomolecules in addition to the visually detectable biomolecule. Nonlimiting examples of such biological systems include cells, cell extracts, tissue samples, electrophoretic gels, assay mixtures, and hybridization reaction mixtures.

"Solid support" refers to any solid substrate known in the art for solid-phase support of molecules, for example a "microparticle" refers to any of a number of small particles useful for attachment to compounds of the invention, including, but not limited to, glass beads, magnetic beads, polymeric beads, nonpolymeric beads, and the like. In certain embodiments, a microparticle comprises polystyrene beads.

A "solid support reside" refers to the functional group remaining attached to a molecule when the molecule is cleaved from the solid support. Solid support residues are known in the art and can be easily derived based on the structure of the solid support and the group linking the molecule thereto.

A "targeting moiety" is a moiety that selectively binds or associates with a particular target, such as an analyte molecule. "Selectively" binding or associating means a targeting moiety preferentially associates or binds with the desired target relative to other targets. In some embodiments the compounds disclosed herein include linkages to targeting moieties for the purpose of selectively binding or associating the compound with an analyte of interest (i.e., the target of the targeting moiety), thus allowing detection of the analyte. Exemplary targeting moieties include, but are not limited to, antibodies, antigens, nucleic acid sequences, enzymes, proteins, cell surface receptor antagonists, and the like. In some embodiments, the targeting moiety is a moiety, such as an antibody, that selectively binds or associates with a target feature on or in a cell, for example a target feature on a cell membrane or other cellular structure, thus allowing for detection of cells of interest. Small molecules that selectively bind or associate with a desired analyte are also contemplated as targeting moieties in certain embodiments. One of skill in the art will understand other analytes, and the corresponding targeting moiety, that will be useful in various embodiments.

"Base pairing moiety" refers to a heterocyclic moiety capable of hybridizing with a complementary heterocyclic moiety via hydrogen bonds (e.g., Watson-Crick base pairing). Base pairing moieties include natural and unnatural bases. Non-limiting examples of base pairing moieties are RNA and DNA bases such adenosine, guanosine, thymidine, cytosine and uridine and analogues thereof.

Embodiments of the invention disclosed herein are also meant to encompass compositions comprising compounds of structures (I), (II), (III) or (IV) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively.

Isotopically-labeled compounds of structure (I), (II), (III) or (IV) can generally be prepared by conventional techniques known to those skilled in the art or by processes analogous to those described below and in the following Examples using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution.

"Salt" includes both acid and base addition salts.

"Acid addition salt" refers to those salts which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Base addition salt" refers to those salts which are prepared from addition of an inorganic base or an organic base to the free acid. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Crystallizations may produce a solvate of the compounds described herein. Embodiments of the present invention include all solvates of the described compounds. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compounds of the invention may be true solvates, while in other cases the compounds of the invention may merely retain adventitious water or another solvent or be a mixture of water plus some adventitious solvent.

Embodiments of the polymeric dyes of the invention (e.g., compounds of structure (I), (II), (III) or (IV)), or their salts, tautomers or solvates may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. Embodiments of the present invention are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomers of any said compounds. Various tautomeric forms of the compounds are easily derivable by those of ordinary skill in the art.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft). Common names familiar to one of ordinary skill in the art are also used.

As noted above, in one embodiment of the present invention, compositions useful as fluorescent and/or colored dyes in various analytical methods are provided. In general terms, embodiments of the present invention are directed to compositions comprising a dye compound (e.g., fluorescent dye) and one or more cyclodextrin. In some embodiments, the compositions comprise a polymeric dye. For example, in some embodiments is provided composition comprising a polymeric dye and a cyclodextrin, the polymeric dye comprising two or more dye moieties M covalently linked by a linker L. Without wishing to be bound by theory, it is believed the cyclodextrin helps to prevent or reduce intramolecular quenching of the dye moieties (e.g., fluorescent and/or colored moieties), thus resulting in a dye compound having a high molar "brightness" (e.g., high fluorescence emission).

Any cyclodextrins may be employed in practice of various embodiments, provided the cyclodextrins reduces or prevents intramolecular quenching of the dye moieties. Typically the cyclodextrins having affinity for the particular dye moiety are selected. In some embodiments, the cyclodextrin is c-cyclodextrin, β-cyclodextrin or γ-cyclodextrin. For example, in some embodiments the cyclodextrin is β-cyclodextrin.

Any polymeric dye (i.e., compounds including two or more dye moieties) may be used to implement embodiments of the invention. In some embodiments, the dye is a compound as disclosed herein (i.e., compound of structure (I), (II), (III) or (IV)). In other embodiments, the polymeric dye is a dye known in the art, for example the polymeric dyes provided in PCT Pub. Nos. WO 2015/027176, WO/2016/138461 and WO/2016/183185, and U.S. Pat. Nos. 7,423,133, 6,670,193 and 6,218,108, the full disclosures of which are hereby incorporated by reference in its entirety.

Advantageously, certain embodiments of the polymeric dyes employed herein are water soluble, thus allowing their use in various assays requiring an aqueous environment. Accordingly, in various embodiments the compositions comprise water.

The dye moiety M is selected depending on the particular assay, and can vary in different embodiments. In some embodiments each M is the same. In other embodiments, the polymeric dye comprises two different types of M moieties. In different embodiments, the polymeric dye comprises from 2 to 10 M moieties, which dye moiety may either be the same or different at each occurrence.

M is selected based on the desired optical properties, for example based on a desired color and/or fluorescence emission wavelength. In some embodiments, M is the same at each occurrence; however, it is important to note that each occurrence of M need not be an identical M, and certain embodiments include compounds wherein M is not the same at each occurrence. For example, in some embodiments each M is not the same and the different M moieties are selected to have absorbance and/or emissions for use in fluorescence resonance energy transfer (FRET) methods. For example, in such embodiments the different M moieties are selected such that absorbance of radiation at one wavelength causes emission of radiation at a different wavelength by a FRET mechanism. Exemplary M moieties can be appropriately selected by one of ordinary skill in the art based on the desired end use. Exemplary M moieties for FRET methods include fluorescein and 5-TAMRA (5-carboxytetramethylrhodamine, succinimidyl ester) dyes.

M may be attached to the remainder of the molecule from any position (i.e., atom) on M. One of skill in the art will recognize means for attaching M to the remainder of molecule. Exemplary methods include the "click" reactions described herein.

In some embodiments, M is a fluorescent or colored moiety. Any fluorescent and/or colored moiety may be used, for examples those known in the art and typically employed in colorimetric, UV, and/or fluorescent assays may be used. Examples of M moieties which are useful in various embodiments of the invention include, but are not limited to: Xanthene derivatives (e.g., fluorescein, rhodamine, Oregon green, eosin or Texas red); Cyanine derivatives (e.g., cyanine, indocarbocyanine, oxacarbocyanine, thiacarbocyanine or merocyanine); Squaraine derivatives and ring-substituted squaraines, including Seta, SeTau, and Square dyes; Naphthalene derivatives (e.g., dansyl and prodan derivatives); Coumarin derivatives; oxadiazole derivatives (e.g., pyridyloxazole, nitrobenzoxadiazole or benzoxadiazole); Anthracene derivatives (e.g., anthraquinones, including DRAQ5, DRAQ7 and CyTRAK Orange); Pyrene derivatives such as cascade blue; Oxazine derivatives (e.g., Nile red, Nile blue, cresyl violet, oxazine 170); Acridine derivatives (e.g., proflavin, acridine orange, acridine yellow); Arylmethine derivatives: auramine, crystal violet, malachite green; and Tetrapyrrole derivatives (e.g., porphin, phthalocyanine or bilirubin). Other exemplary M moieties include: Cyanine dyes, xanthate dyes (e.g., Hex, Vic, Nedd, Joe or Tet); Yakima yellow; Redmond red; tamra; texas red and alexa Fluor® dyes.

In still other embodiments of any of the foregoing, M comprises three or more aryl or heteroaryl rings, or combinations thereof, for example four or more aryl or heteroaryl rings, or combinations thereof, or even five or more aryl or heteroaryl rings, or combinations thereof. In some embodiments, M comprises six aryl or heteroaryl rings, or combinations thereof. In further embodiments, the rings are fused. For example in some embodiments, M comprises three or more fused rings, four or more fused rings, five or more fused rings, or even six or more fused rings.

In some embodiments, M is cyclic. For example, in some embodiments M is carbocyclic. In other embodiment, M is heterocyclic. In still other embodiments of the foregoing, M, at each occurrence, independently comprises an aryl moiety. In some of these embodiments, the aryl moiety is multicyclic. In other more specific examples, the aryl moiety is a fused-multicyclic aryl moiety, for example which may comprise at least 3, at least 4, or even more than 4 aryl rings.

In other embodiments of any of the foregoing compounds of structure (I), M, at each occurrence, independently comprises at least one heteroatom. For example, in some embodiments, the heteroatom is nitrogen, oxygen or sulfur.

In still more embodiments of any of the foregoing, M, at each occurrence, independently comprises at least one substituent. For example, in some embodiments the substituent is a fluoro, chloro, bromo, iodo, amino, alkylamino, arylamino, hydroxy, sulfhydryl, alkoxy, aryloxy, phenyl, aryl, methyl, ethyl, propyl, butyl, isopropyl, t-butyl, carboxy, sulfonate, amide, or formyl group.

In some even more specific embodiments of the foregoing, M, at each occurrence, independently is a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9,10-ethynylanthracene or ter-naphthyl moiety. In other embodiments, M is, at each occurrence, independently p-terphenyl, perylene, azobenzene, phenazine, phenanthroline, acridine, thioxanthrene, chrysene, rubrene, coronene, cyanine, perylene imide, or perylene amide or a derivative thereof. In still more embodiments, M is, at each occurrence, independently a coumarin dye, resorufin dye, dipyrromethaneboron difluoride dye, ruthenium bipyridyl dye, energy transfer dye, thiazole orange dye, polymethine or N-aryl-1,8-naphthalimide dye.

In still more embodiments of any of the foregoing, M at each occurrence is the same. In other embodiments, each M is different. In still more embodiments, one or more M is the same and one or more M is different.

In some embodiments, M is pyrene, perylene, perylene monoimide or 6-FAM or derivative thereof. In some other embodiments, M has one of the following structures:

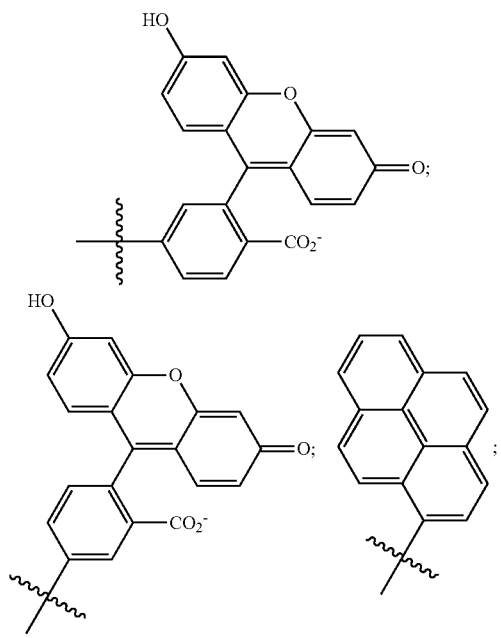

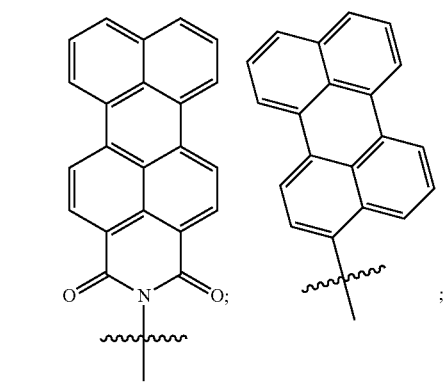

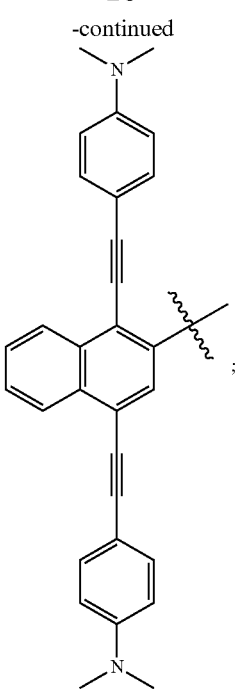

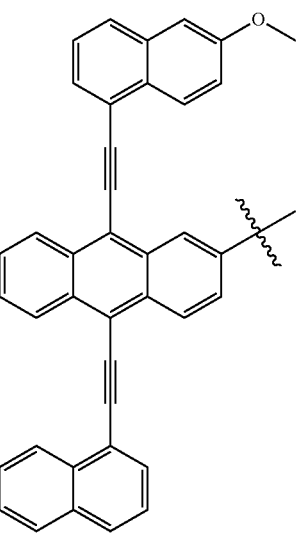

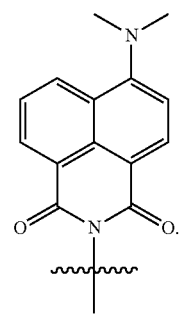

In some other embodiments, M has one of the following structures:

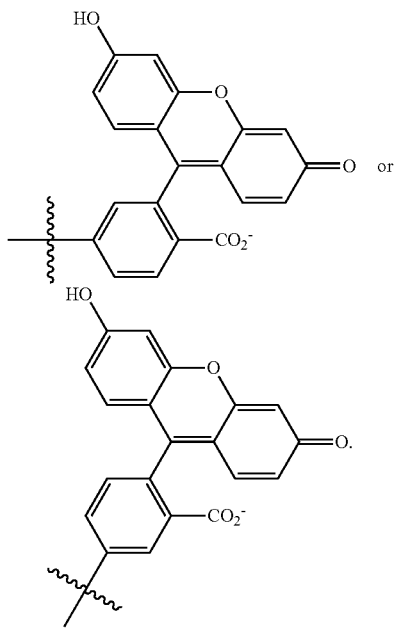

Although M moieties comprising carboxylic acid groups are sometimes depicted in the anionic form ($CO_2^-$) above, one of skill in the art will understand that this will vary depending on pH, and the protonated form ($CO_2H$) is included in various embodiments.

In some embodiments the polymeric dye compounds have the following structure (A):

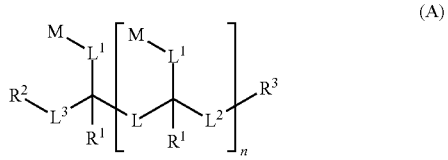

(A)

wherein:

L is the linker;

M is, at each occurrence, independently the dye moiety;

$L^1$ is at each occurrence, independently either: i) an optional alkylene, alkenylene, alkynylene, heteroalkylene, heteroalkenylene, heteroalkynylene or heteroatomic linker; or ii) a linker comprising a functional group capable of formation by reaction of two complementary reactive groups;

$L^2$ and $L^3$ are, at each occurrence, independently an optional alkylene, alkenylene, alkynylene, heteroalkylene, heteroalkenylene, heteroalkynylene or heteroatomic linker;

$R^1$ is, at each occurrence, independently H, alkyl or alkoxy;

$R^2$ and $R^3$ are each independently H, OH, SH, alkyl, alkoxy, alkylether, heteroalkyl, —$OP(=R_a)(R_b)R_c$, Q or L';

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected analogue thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I); and n is an integer of one or greater.

In different embodiments of (A):

L is the linker;

M is, at each occurrence, independently the dye moiety;

$L^1$, $L^2$ and $L^3$ are, at each occurrence, independently an optional linker;

$R^1$ is, at each occurrence, independently H, alkyl or alkoxy;

$R^2$ and $R^3$ are each independently H, OH, SH, alkyl, alkoxy, alkylether, —$OP(=R_a)(R_b)R_c$, Q, a linker comprising a covalent bond to Q, a linker comprising a covalent bond to an analyte molecule, a linker comprising a covalent bond to a solid support or a linker comprising a covalent bond to a further compound of structure (I), wherein: $R_a$ is O or S; $R_b$ is OH, SH, $O^-$, $S^-$, $OR_d$ or $SR_d$; $R_c$ is OH, SH, $O^-$, $S^-$, $OR_d$, $SR_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion;

Q is, at each occurrence, independently a moiety comprising a reactive group capable of forming a covalent bond with an analyte molecule, a solid support or a complementary reactive group Q'; and n is an integer of one or greater.

The dye moieties M are often hydrophobic, and thus in certain embodiments L is selected to improve the water solubility of the polymeric dye compound. In some embodiments, L comprises hydrophilic functional groups. In other embodiments, L comprises charged functional groups (e.g., charged at pH values ranging from 1-14 in an aqueous environment). In different embodiments, L comprises phosphate, amino acid or alkylene oxide functional groups.

The polymeric dye typically comprises two or more M moieties. Although the exact structure of the polymeric dye is not critical, various embodiments include polymeric dyes having one of structures (I), (II), (III) or (IV) as set forth below.

Polymeric Dyes of Structure (I)

In some embodiments are provided a compound of structure (I). In some different embodiments compositions comprising a cyclodextrin and a compound of structure (I) are provided. Compounds of structure (I) have the following structure:

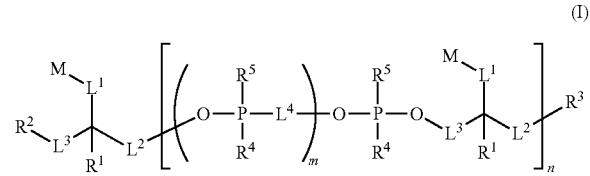

(I)

or a stereoisomer, salt or tautomer thereof, wherein:

M is, at each occurrence, independently a moiety comprising two or more carbon-carbon double bonds and at least one degree of conjugation;

$L^1$ is at each occurrence, independently either: i) an optional alkylene, alkenylene, alkynylene, heteroalkylene, heteroalkenylene, heteroalkynylene or heteroatomic linker; or ii) a linker comprising a functional group capable of formation by reaction of two complementary reactive groups;

$L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently a heteroalkylene, heteroalkenylene or heteroalkynylene linker of greater than three atoms in length, wherein the heteroatoms in the heteroalkylene, heteroalkenylene and heteroalkynylene linker are selected from O, N and S;

$R^1$ is, at each occurrence, independently H, alkyl or alkoxy;

$R^2$ and $R^3$ are each independently H, OH, SH, alkyl, alkoxy, alkylether, heteroalkyl, —OP(=$R_a$)($R_b$)$R_c$, Q or L';

$R^4$ is, at each occurrence, independently OH, SH, O$^-$, S$^-$, O$R_d$ or S$R_d$;

$R^5$ is, at each occurrence, independently oxo, thioxo or absent;

$R_a$ is O or S;

$R_b$ is OH, SH, O$^-$, S$^-$, O$R_d$ or S$R_d$;

$R_c$ is OH, SH, O$^-$, S$^-$, O$R_d$, OL', S$R_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected analogue thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

m is, at each occurrence, independently an integer of zero or greater, provided that at least one occurrence of m is an integer of one or greater; and n is an integer of one or greater.

In different embodiments of the compound of structure (I):

M is, at each occurrence, independently the dye moiety;

$L^1$ is at each occurrence, independently either: i) an optional alkylene, alkenylene, alkynylene, heteroalkylene, heteroalkenylene, heteroalkynylene or heteroatomic linker; or ii) a linker comprising a functional group capable of formation by reaction of two complementary reactive groups;

$L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently a heteroalkylene, heteroalkenylene or heteroalkynylene linker;

$R^1$ is, at each occurrence, independently H, alkyl or alkoxy;

$R^2$ and $R^3$ are each independently H, OH, SH, alkyl, alkoxy, alkylether, —OP(=$R_a$)($R_b$)$R_c$, Q, a linker comprising a covalent bond to Q, a linker comprising a covalent bond to an analyte molecule, a linker comprising a covalent bond to a solid support or a linker comprising a covalent bond to a further compound of structure (I), wherein: $R_a$ is O or S; $R_b$ is OH, SH, O$^-$, S$^-$, O$R_d$ or S$R_d$; R is OH, SH, O$^-$, S$^-$, O$R_d$, S$R_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion;

$R^4$ is, at each occurrence, independently OH, SH, O$^-$, S$^-$, O$R_d$ or S$R_d$;

$R^5$ is, at each occurrence, independently oxo, thioxo or absent;

Q is, at each occurrence, independently a moiety comprising a reactive group capable of forming a covalent bond with an analyte molecule, a solid support or a complementary reactive group Q';

m is, at each occurrence, independently an integer of zero or greater, provided that at least one occurrence of m is an integer of one or greater; and n is an integer of one or greater.

The various linkers and substituents (e.g., M, Q, $R^1$, $R^2$, $R^3$, $R^c$ $L^1$, $L^2$, $L^3$ and $L^4$) in the compound of structure (I) are optionally substituted with one more substituent. For example, in some embodiments the optional substituent is selected to optimize the water solubility or other property of the compound of structure (I). In certain embodiments, each alkyl, alkoxy, alkylether, alkoxyalkylether, phosphoalkyl, thiophosphoalkyl, phosphoalkylether and thiophosphoalkylether in the compound of structure (I) is optionally substituted with one more substituent selected from the group consisting of hydroxyl, alkoxy, alkylether, alkoxyalkylether, sulfhydryl, amino, alkylamino, carboxyl, phosphate, thiophosphate, phosphoalkyl, thiophosphoalkyl, phosphoalkylether and thiophosphoalkylether. In certain embodiments of structure (I) the optional substituent is —OP(=$R_a$)($R_b$)$R_c$, where $R_a$, $R_b$ and $R_c$ are as defined for the compound of structure (I).

In some embodiments, L is at each occurrence, independently an optional alkylene, alkenylene, alkynylene, heteroalkylene, heteroalkenylene, heteroalkynylene or heteroatomic linker. In other embodiments, $L^1$ is at each occurrence, independently a linker comprising a functional group capable of formation by reaction of two complementary reactive groups, for example a Q group.

In some embodiments of structure (I), $L^4$ is at each occurrence, independently a heteroalkylene linker. In other more specific embodiments, $L^4$ is at each occurrence, independently an alkylene oxide linker. For example, in some embodiments $L^4$ is polyethylene oxide, and the compound has the following structure (IA):

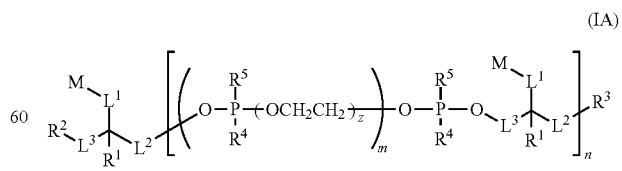

(IA)

wherein z is an integer from 2 to 100, for example an integer from 3 to 6. In some embodiments of (IA), z is an integer from 2-30, for example from about 20 to 25, or about 23. In some embodiments, z is an integer from 2 to 10, for example from 3 to 6. In some embodiments, z is 3. In some embodiments, z is 4. In some embodiments, z is 5. In some embodiments, z is 6.

The optional linker $L^1$ can be used as a point of attachment of the M moiety to the remainder of the compound. For example, in some embodiments a synthetic precursor to the compound of structure (I) is prepared, and the M moiety is attached to the synthetic precursor using any number of facile methods known in the art, for example methods referred to as "click chemistry." For this purpose any reaction which is rapid and substantially irreversible can be used to attach M to the synthetic precursor to form a compound of structure (I). Exemplary reactions include the copper catalyzed reaction of an azide and alkyne to form a triazole (Huisgen 1,3-dipolar cycloaddition), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse-demand Diels-Alder, alkene and tetrazole photoreaction and various displacement reactions, such as displacement of a leaving group by nucleophilic attack on an electrophilic atom. Exemplary displacement reactions include reaction of an amine with: an activated ester; an N-hydroxysuccinimide ester; an isocyanate; an isothiocyanate or the like. In some embodiments the reaction to form $L^1$ may be performed in an aqueous environment.

Accordingly, in some embodiments $L^1$ is at each occurrence a linker comprising a functional group capable of formation by reaction of two complementary reactive groups, for example a functional group which is the product of one of the foregoing "click" reactions. In various embodiments, for at least one occurrence of $L^1$, the functional group can be formed by reaction of an aldehyde, oxime, hydrazone, alkyne, amine, azide, acylazide, acylhalide, nitrile, nitrone, sulfhydryl, disulfide, sulfonyl halide, isothiocyanate, imidoester, activated ester, (e.g., N-hydroxysuccinimide ester), ketone, α,β-unsaturated carbonyl, alkene, maleimide, α-haloimide, epoxide, aziridine, tetrazine, tetrazole, phosphine, biotin or thiirane functional group with a complementary reactive group. For example, reaction of an amine with an N-hydroxysuccinimide ester or isothiocyanate.

In other embodiments, for at least one occurrence of $L^1$, the functional group can be formed by reaction of an alkyne and an azide. In other embodiments, for at least one occurrence of $L^1$, the functional group can be formed by reaction of an amine (e.g., primary amine) and an N-hydroxysuccinimide ester or isothiocyanate.

In more embodiments, for at least one occurrence of $L^1$, the functional group comprises an alkene, ester, amide, thioester, disulfide, carbocyclic, heterocyclic or heteroaryl group. In more embodiments, for at least one occurrence of $L^1$, the functional group comprises an alkene, ester, amide, thioester, thiourea, disulfide, carbocyclic, heterocyclic or heteroaryl group. In other embodiments, the functional group comprises an amide or thiourea. In some more specific embodiments, for at least one occurrence of $L^1$, $L^1$ is a linker comprising a triazolyl functional group. While in other embodiments, for at least one occurrence of $L^1$, $L^1$ is a linker comprising an amide or thiourea functional group.

In still other embodiments, for at least one occurrence of $L^1$, $L^1$—M has the following structure:

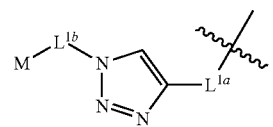

wherein $L^{1a}$ and $L^{1b}$ are each independently optional linkers.

In different embodiments, for at least one occurrence of $L^1$, $L^1$—M has the following structure:

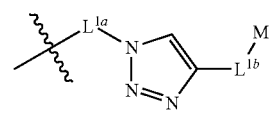

wherein $L^{1a}$ and $L^{1b}$ are each independently optional linkers.

In various embodiments of the foregoing, $L^{1a}$ or $L^{1b}$, or both, is absent. In other embodiments, $L^{1a}$ or $L^{1b}$, or both, is present.

In some embodiments $L^{1a}$ and $L^{1b}$, when present, are each independently alkylene or heteroalkylene. For example, in some embodiments $L^{1a}$ and $L^{1b}$, when present, independently have one of the following structures:

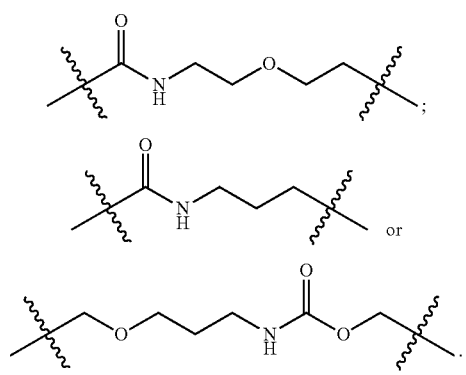

In still other different embodiments of structure (I), $L^1$ is at each occurrence, independently an optional alkylene or heteroalkylene linker. In certain embodiments, $L^1$ has one of the following structures:

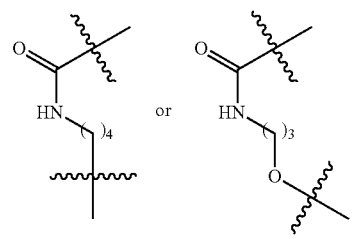

In more embodiments, $L^2$ and $L^3$ are, at each occurrence, independently $C_1$-$C_6$ alkylene, $C_2$-$C_6$ alkenylene or $C_2$-$C_6$ alkynylene. For example, in some embodiments the compound has the following structure (IB):

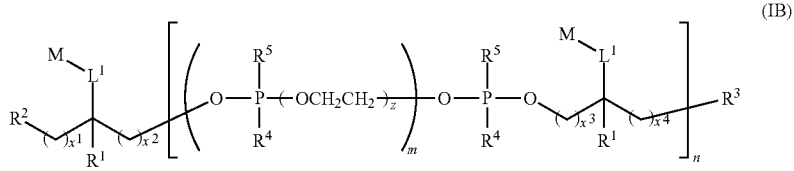

(IB)

wherein:

$x^1$, $x^2$, $x^3$ and $x^4$ are, at each occurrence, independently an integer from 0 to 6; and z is an integer from 2 to 100, for example from 3 to 6.

In certain embodiments of the compound of structure (IB), at least one occurrence of $x^1$, $x^2$, $x^3$ or $x^4$ is 1. In other embodiments, $x^1$, $x^2$, $x^3$ and $x^4$ are each 1 at each occurrence. In other embodiments, $x^1$ and $x^3$ are each 0 at each occurrence. In some embodiments, $x^2$ and $x^4$ are each 1 at each occurrence. In still other embodiments, $x^1$ and $x^3$ are each 0 at each occurrence, and $x^2$ and $x^4$ are each 1 at each occurrence.

In some more specific embodiments of the compound of structure (IB), $L^1$, at each occurrence, independently comprises a triazolyl functional group. In some other specific embodiments of the compound of structure (IB), $L^1$, at each occurrence, independently comprises an amide or thiourea functional group. In other embodiments of the compound of structure (IB), $L^1$, at each occurrence, independently an optional alkylene or heteroalkylene linker.

In still other embodiments of any of the compounds of structure (I), $R^4$ is, at each occurrence, independently OH, O⁻ or $OR_d$. It is understood that "$OR_d$" and "$SR_d$" are intended to refer to O⁻ and S⁻ associated with a cation. For example, the disodium salt of a phosphate group may be represented as:

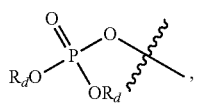

where $R_d$ is sodium ($N_a^+$).

In other embodiments of any of the compounds of structure (I), $R^5$ is, at each occurrence, oxo.

In some different embodiments of any of the foregoing compounds, $R^1$ is H.

In other various embodiments, $R^2$ and $R^3$ are each independently OH or —OP(=$R_a$)($R_b$)$R_c$. In some different embodiments, $R^2$ or $R^3$ is OH or —OP(=$R_a$)($R_b$)$R_c$, and the other of $R^2$ or $R^3$ is Q or a linker comprising a covalent bond to Q.

In still more different embodiments of any of the foregoing compounds of structure (I), $R^2$ and $R^3$ are each independently —OP(=$R_a$)($R_b$)$R_c$. In some of these embodiments, $R_c$ is OL'.

In other embodiments, $R^2$ and $R^3$ are each independently —OP(=$R_a$)($R_b$)OL', and L' is an alkylene or heteroalkylene linker to: Q, a targeting moiety, an analyte (e.g., analyte molecule), a solid support, a solid support residue, a nucleoside or a further compound of structure (I).

The linker L' can be any linker suitable for attaching Q, a targeting moiety, an analyte (e.g., analyte molecule), a solid support, a solid support residue, a nucleoside or a further compound of structure (I) to the compound of structure (I). Advantageously certain embodiments include use of L' moieties selected to increase or optimize water solubility of the compound. In certain embodiments, L' is a heteroalkylene moiety. In some other certain embodiments, L' comprises an alkylene oxide or phosphodiester moiety, or combinations thereof.

In certain embodiments, L' has the following structure:

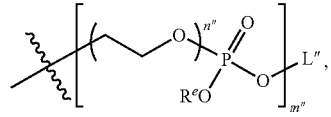

wherein:

m" and n" are independently an integer from 1 to 10;

$R^e$ is H, an electron pair or a counter ion;

L" is $R^e$ or a direct bond or linkage to: Q, a targeting moiety, an analyte (e.g., analyte molecule), a solid support, a solid support residue, a nucleoside or a further compound of structure (I).

In some embodiments, m" is an integer from 4 to 10, for example 4, 6 or 10. In other embodiments n" is an integer from 3 to 6, for example 3, 4, 5 or 6.

In some other embodiments, L" is an alkylene or heteroalkylene moiety. In some other certain embodiments, L" comprises an alkylene oxide, phosphodiester moiety, sulfhydryl, disulfide or maleimide moiety or combinations thereof.

In certain of the foregoing embodiments, the targeting moiety is an antibody or cell surface receptor antagonist.

In other more specific embodiments of any of the foregoing compounds of structure (I), $R^2$ or $R^3$ has one of the following structures:

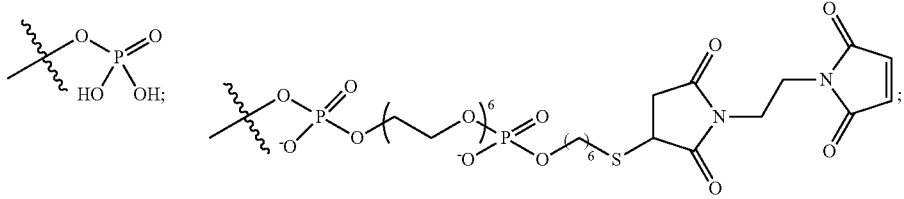

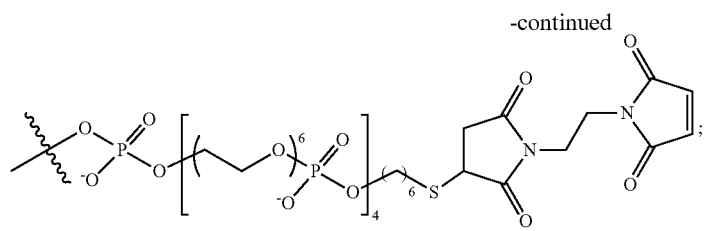

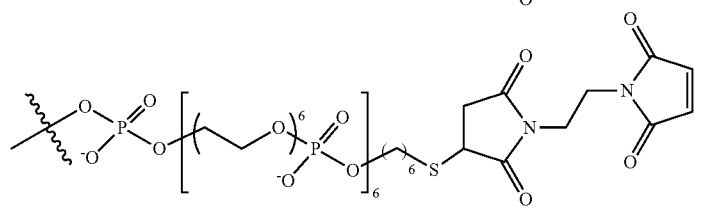

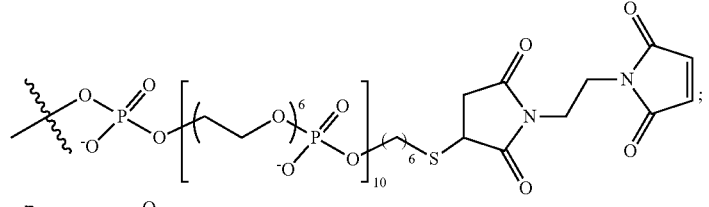

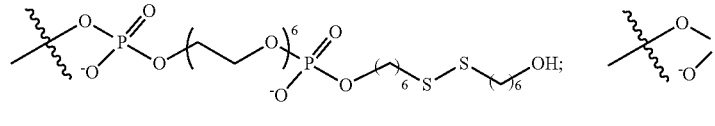

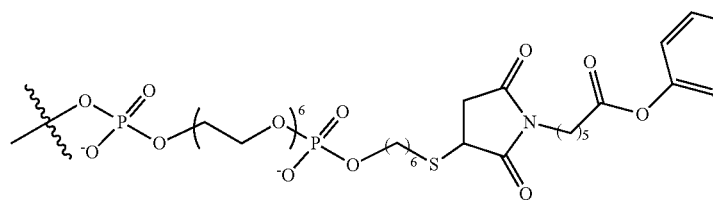

Certain embodiments of compounds of structure (I) can be prepared according to solid-phase synthetic methods analogous to those known in the art for preparation of oligonucleotides. Accordingly, in some embodiments, L' is a linkage to a solid support, a solid support residue or a nucleoside. Solid supports comprising an activated deoxythymidine (dT) group are readily available, and in some embodiments can be employed as starting material for preparation of compounds of structure (I). Accordingly, in some embodiments $R^2$ or $R^3$ has the following structure:

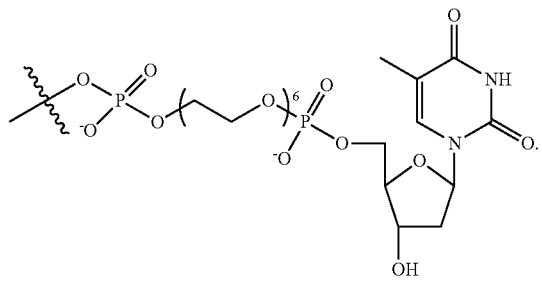

One of skill in the art will understand that the dT group depicted above is included for ease of synthesis and economic efficiencies only, and is not required. Other solid supports can be used and would result in a different nucleoside or solid support residue being present on L', or the nucleoside or solid support residue can be removed or modified post synthesis.

In still other embodiments, Q is, at each occurrence, independently a moiety comprising a reactive group capable of forming a covalent bond with an analyte molecule or a solid support. In other embodiments, Q is, at each occurrence, independently a moiety comprising a reactive group capable of forming a covalent bond with a complementary reactive group Q'. For example, in some embodiments, Q' is present on a further compound of structure (I) (e.g., in the $R^2$ or $R^3$ position), and Q and Q' comprise complementary reactive groups such that reaction of the compound of structure (I) and the further compound of structure (I) results in covalently bound dimer of the compound of structure (I). Multimer compounds of structure (I) can also be prepared in an analogous manner and are included within the scope of embodiments of the invention.

The type of Q group and connectivity of the Q group to the remainder of the compound of structure (I) is not limited, provided that Q comprises a moiety having appropriate reactivity for forming the desired bond.

In certain embodiments, Q is a moiety which is not susceptible to hydrolysis under aqueous conditions, but is sufficiently reactive to form a bond with a corresponding group on an analyte molecule or solid support (e.g., an amine, azide or alkyne).

Certain embodiments of compounds of structure (I) comprise Q groups commonly employed in the field of bioconjugation. For example in some embodiments, Q comprises a nucleophilic reactive group, an electrophilic reactive group or a cycloaddition reactive group. In some more specific embodiments, Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group. In some embodiments, the activated ester is an N-succinimide ester, imidoester or polyflourophenyl ester. In other embodiments, the alkyne is an alkyl azide or acyl azide.

The Q groups can be conveniently provided in protected form to increase storage stability or other desired properties, and then the protecting group removed at the appropriate time for conjugation with, for example, a targeting moiety or analyte. Accordingly, Q groups include "protected forms" of a reactive group, including any of the reactive groups described above and in the Table 1 below. A "protected form" of Q refers to a moiety having lower reactivity under predetermined reaction conditions relative to Q, but which can be converted to Q under conditions, which preferably do not degrade or react with other portions of the compound of structure (I). One of skill in the art can derive appropriate protected forms of Q based on the particular Q and desired end use and storage conditions. For example, when Q is SH, a protected form of Q includes a disulfide, which can be reduce to reveal the SH moiety using commonly known techniques and reagents.

Exemplary Q moieties are provided in Table I below.

TABLE 1

| Exemplary Q Moieties | |
|---|---|
| Structure | Class |
| 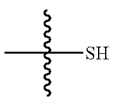 | Sulfhydryl |
| 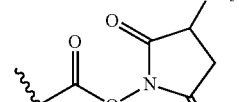 | Isothiocyanate |
| 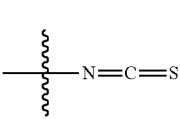 | Imidoester |
|  | Acyl Azide |
| 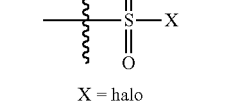 | Activated Ester |

TABLE 1-continued

| Exemplary Q Moieties | |
|---|---|
| Structure | Class |
| 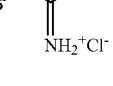 | Activated Ester |
| 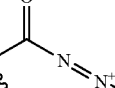 | Activated Ester |
| 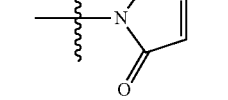 | Activated Ester |
| 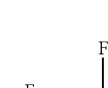 | Activated Ester |
| 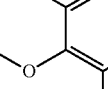 | Activated Ester |
| 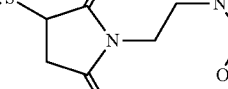 X = halo | Sulfonyl halide |
| 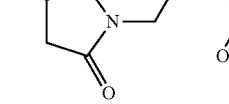 | Maleimide |
| 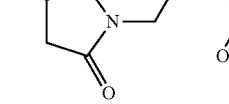 | Maleimide |

TABLE 1-continued

Exemplary Q Moieties

| Structure | Class |
|---|---|
| 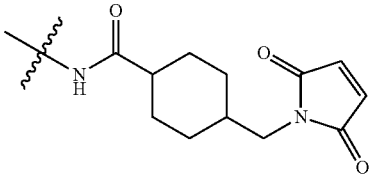 [SMILES: *NC(=O)C1CCC(CN2C(=O)C=CC2=O)CC1] | Maleimide |
| 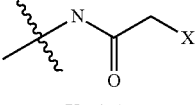  X = halo | α-haloimide |
| 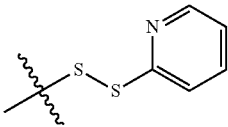 [SMILES: *SSc1ccccn1] | Disulfide |
| 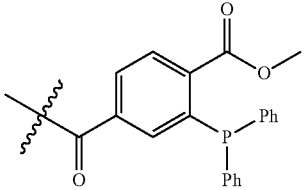 [SMILES: *C(=O)c1ccc(C(=O)OC)c(P(c2ccccc2)c2ccccc2)c1] | Phosphine |
| 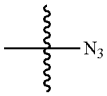 | Azide |
| 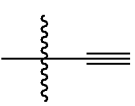 | Alkyne |
| 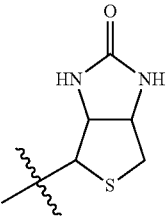 [SMILES: *C1SCC2NC(=O)NC21] | Biotin |
|  | Diene |
| 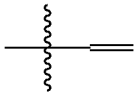 | Alkene/ dienophile |
| 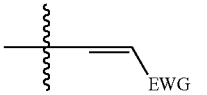  EWG = electron withdrawing group | Alkene/ dienophile |
| —$NH_2$ | Amino |

It should be noted that in some embodiments, wherein Q is SH, the SH moiety will tend to form disulfide bonds with another sulfhydryl group, for example on another compound of structure (I). Accordingly, some embodiments include compounds of structure (I), which are in the form of disulfide dimers, the disulfide bond being derived from SH Q groups.

Also included within the scope of certain embodiments are compounds of structure (I), wherein one, or both, of $R^2$ and $R^3$ comprises a linkage to a further compound of structure (I). For example, wherein one or both of $R^2$ and $R^3$ are —OP(=$R_a$)($R_b$)$R_c$, and Rc is OL', and L' is a linker comprising a covalent bond to a further compound of structure (I). Such compounds can be prepared by preparing a first compound of structure (I) having for example about 10 "M" moieties (i.e., n=9) and having an appropriate "Q" for reaction with a complementary Q' group on a second compound of structure (I). In this manner, compounds of structure (I), having any number of "M" moieties, for example 100 or more, can be prepared without the need for sequentially coupling each monomer. Exemplary embodiments of such compounds of structure (I) have the following structure (I')

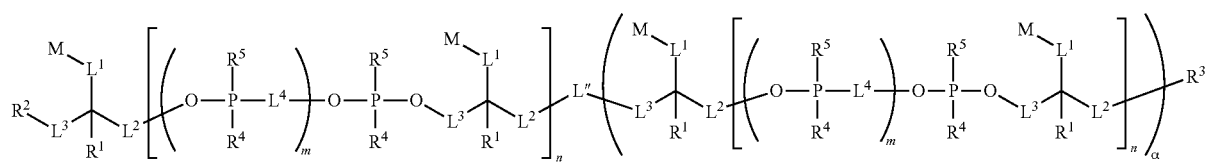

(I')

wherein:
each occurrence of $R^1$, $R^2$, $R^3$, $R^4$, $R^5$, $L^1$, $L^2$, $L^3$, $L^4$, M, m and n are independently as defined for a compound of structure (I);
L" is a linker comprising a functional group resulting from reaction of a Q moiety with a corresponding Q' moiety; and
α is an integer greater than 1, for example from 1 to 100, or 1 to 10.

An exemplary compound of structure (I') is provided in Example 5. Other compounds of structure (I') are derivable by those of ordinary skill in the art, for example by dimerizing or polymerizing compounds of structure (I) provided herein.

In other embodiments, the Q moiety is conveniently masked (e.g., protected) as a disulfide moiety, which can later be reduced to provide an activated Q moiety for binding to a desired analyte molecule or targeting moiety. For example, the Q moiety may be masked as a disulfide having the following structure:

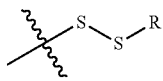

wherein R is an optionally substituted alkyl group. For example, in some embodiments, Q is provided as a disulfide moiety having the following structure:

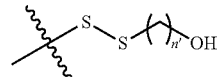

where n is an integer from 1 to 10, for example 6.

In some other embodiments of structure (I), one of $R^2$ or $R^3$ is OH or —OP(=$R_a$)($R_b$)$R_c$, and the other of $R^2$ or $R^3$ is a linker comprising a covalent bond to an analyte molecule or a linker comprising a covalent bond to a solid support. For example, in some embodiments the analyte molecule is a nucleic acid, amino acid or a polymer thereof. In other embodiments, the analyte molecule is an enzyme, receptor, receptor ligand, antibody, glycoprotein, aptamer or prion. In still different embodiments, the solid support is a polymeric bead or nonpolymeric bead.

The value for m is another variable that can be selected based on the desired fluorescence and/or color intensity. In some embodiments, m is, at each occurrence, independently an integer from 1 to 10, 3 to 10 or 7 to 9. In other embodiments, m is, at each occurrence, independently an integer from 1 to 5, for example 1, 2, 3, 4 or 5. In other embodiments, m is, at each occurrence, independently an integer from 5 to 10, for example 5, 6, 7, 8, 9 or 10. In other embodiments, each occurrence of m is an integer of one or greater. For example, in some embodiments each occurrence of m is an integer of two or greater or three or greater.

In other embodiments, m is, at each occurrence, independently an integer greater than 2, and z is an integer from 3 to 10, for example in some embodiment m is, at each occurrence, independently an integer greater than 2, such as 3, 4, 5 or 6, and z is an integer from 3 to 6.

The fluorescence intensity can also be tuned by selection of different values of n. In certain embodiments, n is an integer from 1 to 100. In other embodiments, n is an integer from 1 to 10. In some embodiments, n is 1. In some embodiments n is 2. In some embodiments n is 3. In some embodiments n is 4. In some embodiments n is 5. In some embodiments n is 6. In some embodiments n is 7. In some embodiments n is 8. In some embodiments n is 9. In some embodiments n is 10.

M in the compound of structure is selected from any of the moieties described above.

In some specific embodiments, the polymeric dye compound in the compositions is a compound selected from Table 2. The compounds in Table 2 were prepared according to the procedures set forth in the Examples and their identity confirmed by mass spectrometry.

TABLE 2

Exemplary Compounds of Structure I

| No. | MW. Found Calc. | Structure |
|---|---|---|
| I-1 | 1364.6 1365.2 | 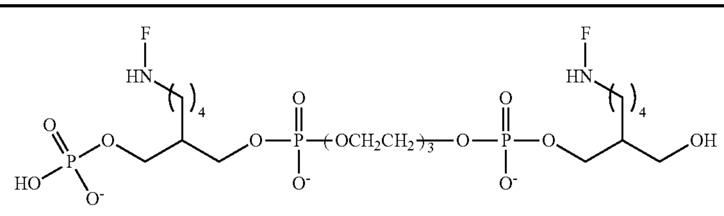 |
| I-2 | 1576.2 1577.3 | 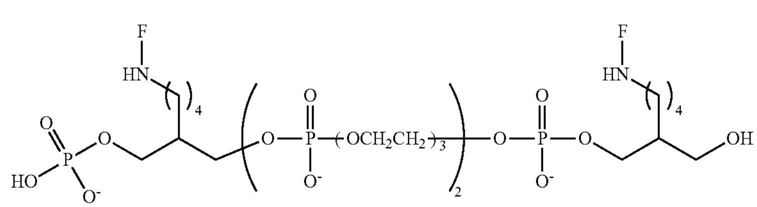 |

TABLE 2-continued

Exemplary Compounds of Structure I

| No. | MW. Found Calc. | Structure |
|---|---|---|
| I-3 | 1497.4 1497.3 | 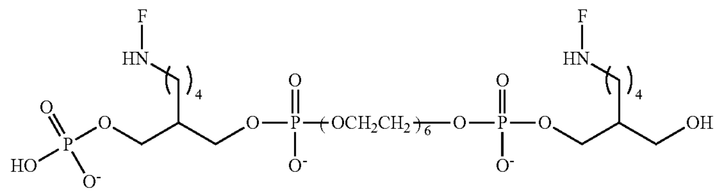 |
| I-4 | 1841.4 1841.6 | 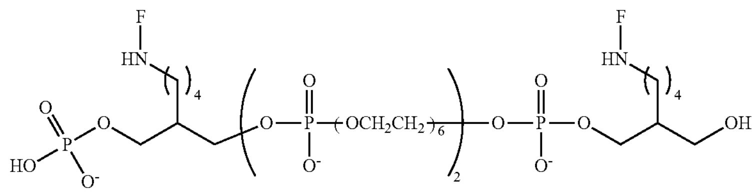 |
| I-5 | 2185.8 2185.9 | 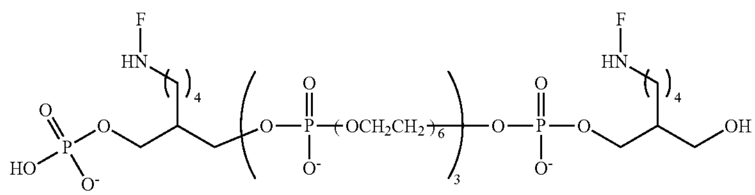 |
| I-6 | 2532.2 2530.2 | 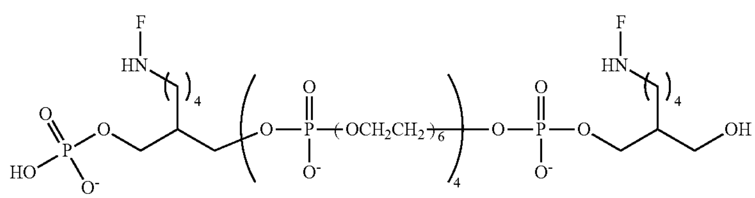 |
| I-7 | 1789.6 1789.5 | 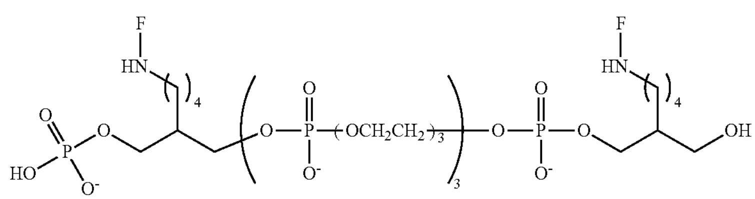 |
| I-8 | 2001.6 2001.6 | 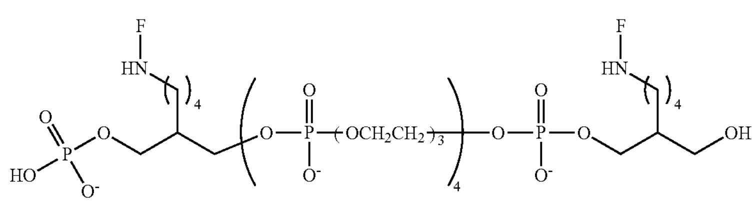 |
| I-9 | 2213.5 2213.8 | 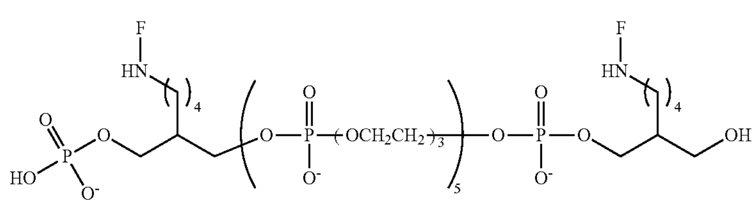 |

TABLE 2-continued

Exemplary Compounds of Structure I

| No. | MW. Found Calc. | Structure |
|---|---|---|
| I-10 | 4481.6 4480.9 | 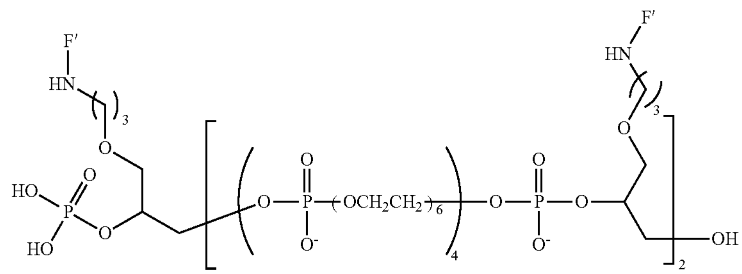 |
| I-11 | 8375.9 8374.3 | 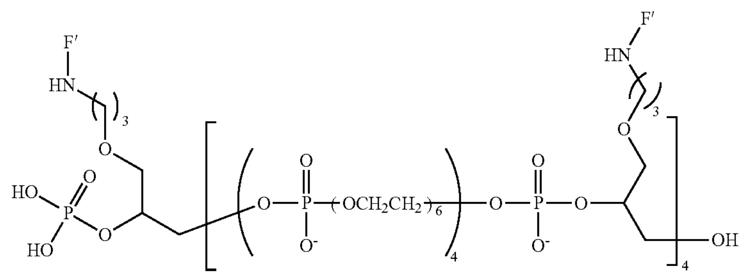 |
| I-12 | TBD | $z = 3, 4, 5$ or $6$; $m = 2, 3, 4$ or $5$; $n = 1\text{-}10$ |
| I-13 | TBD | 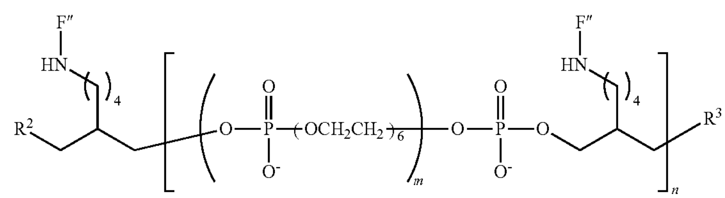 |
| I-14 | TBD | 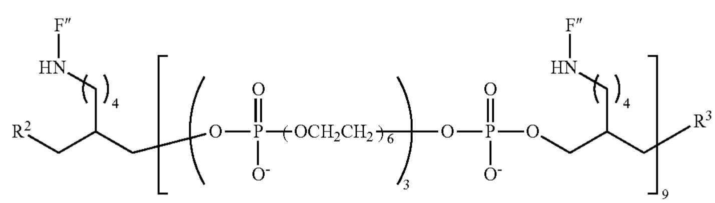 |
| I-15 | TBD | 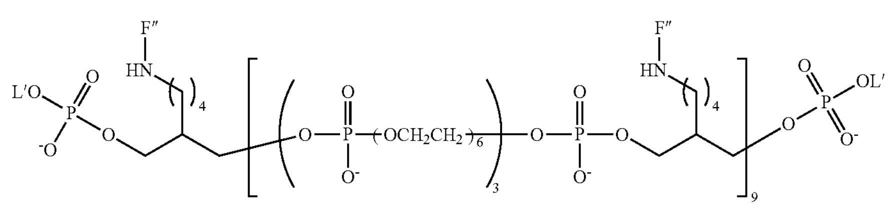 |

TABLE 2-continued
Exemplary Compounds of Structure I
| No. | MW. Found Calc. | Structure |
|---|---|---|
| I-16 | TBD | 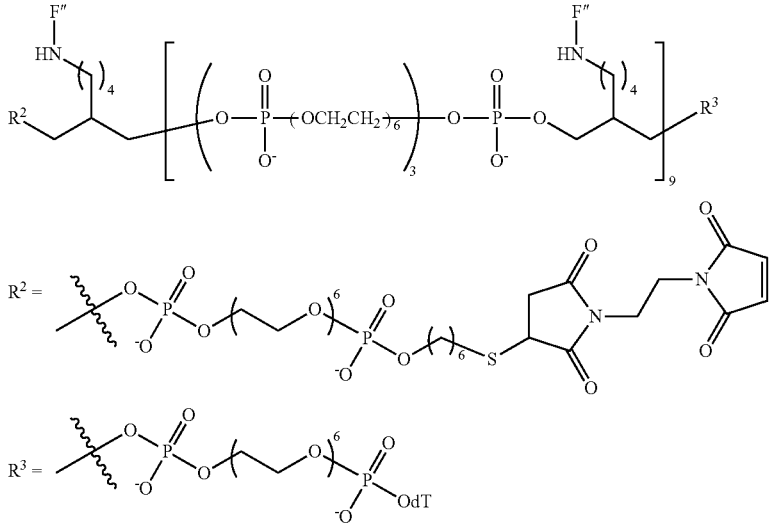 |
| I-17 | 15684.6 15681.5 | 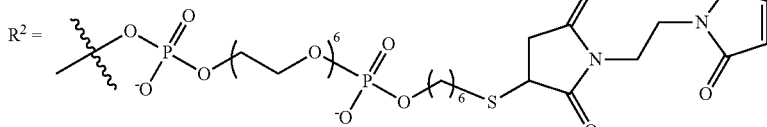 |
| I-18 | TBD | 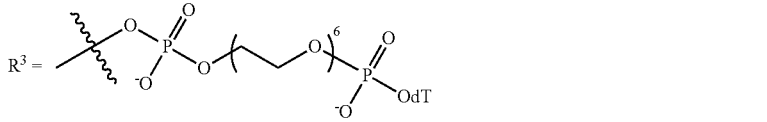 |

TABLE 2-continued
Exemplary Compounds of Structure I
| No. | MW. Found Calc. | Structure |
|---|---|---|
| I-19 | TBD | 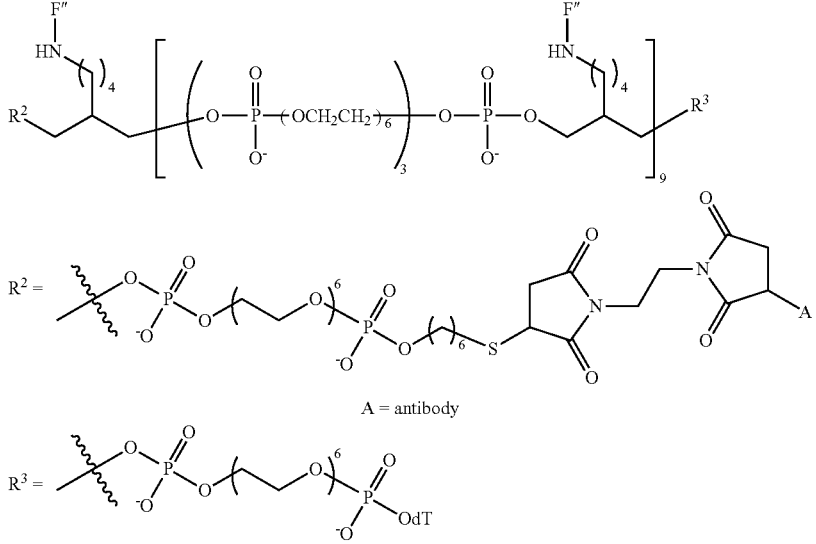 |
| I-20 | TBD | 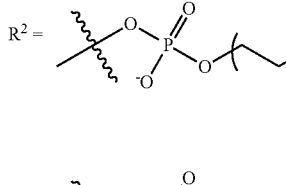 |
| I-21 | TBD | 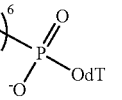<br>m" = 4 (I-21A)<br>m" = 10 (I-21B) |

TABLE 2-continued

Exemplary Compounds of Structure I

| No. | MW. Found Calc. | Structure |
|---|---|---|

I-22 TBD

I-23 TBD

I-24 TBD m″ = 4 or 10

TABLE 2-continued

Exemplary Compounds of Structure I

| No. | MW. Found Calc. | Structure |
|---|---|---|

I-25  TBD

I-26  TBD

I-27  TBD

TABLE 2-continued

Exemplary Compounds of Structure I

| No. | MW. Found Calc. | Structure |
|---|---|---|
| I-28 | TBD | (structure) |
| I-29 | TBD | (structure) |
| I-30 | TBD | (structure) |

A = antibody

TABLE 2-continued

Exemplary Compounds of Structure I

| No. | MW. Found Calc. | Structure |
|-----|-----------------|-----------|
| I-31 | TBD | |
| I-32 | 7241.2 / 7238.2 | |
| I-33 | TBD | |

TABLE 2-continued

Exemplary Compounds of Structure I

| No. | MW. Found Calc. | Structure |
|---|---|---|
| I-34 | TBD | 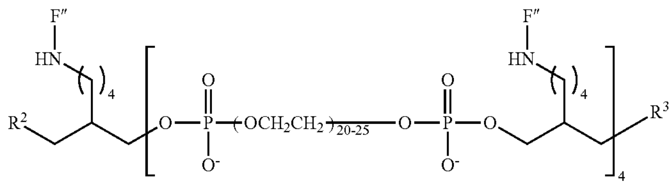 |
| I-35 | TBD | 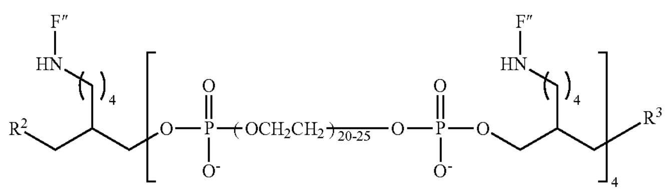 |
| I-36 | TBD | 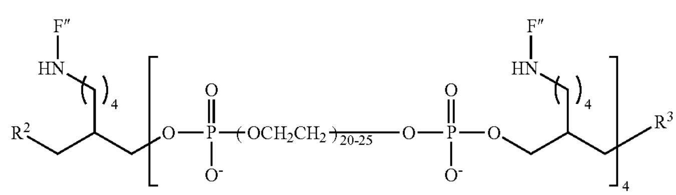 |

TABLE 2-continued

Exemplary Compounds of Structure I

| No. | MW. Found Calc. | Structure |
|---|---|---|
| I-37 | 6997.1 6997.0 | 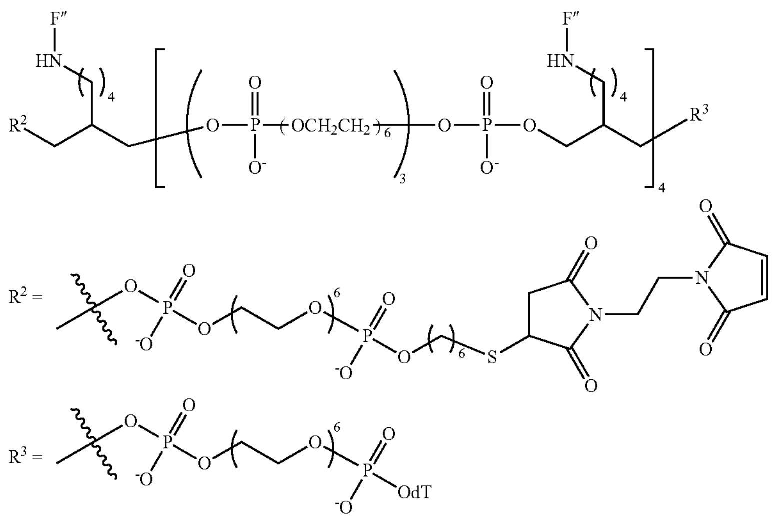 |
| I-38 | TBD | 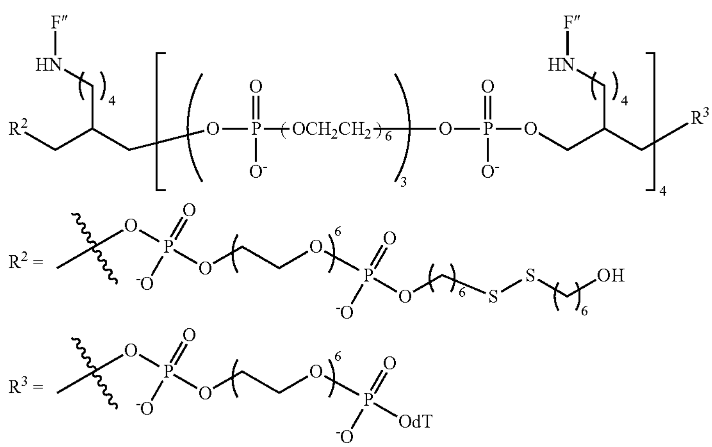 |
| I-39 | TBD | 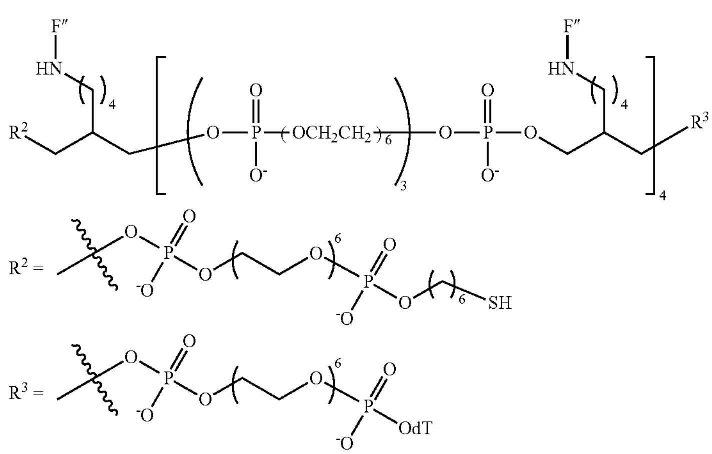 |

TABLE 2-continued
Exemplary Compounds of Structure I
| No. | MW. Found Calc. | Structure |
|---|---|---|
| I-40 | TBD | 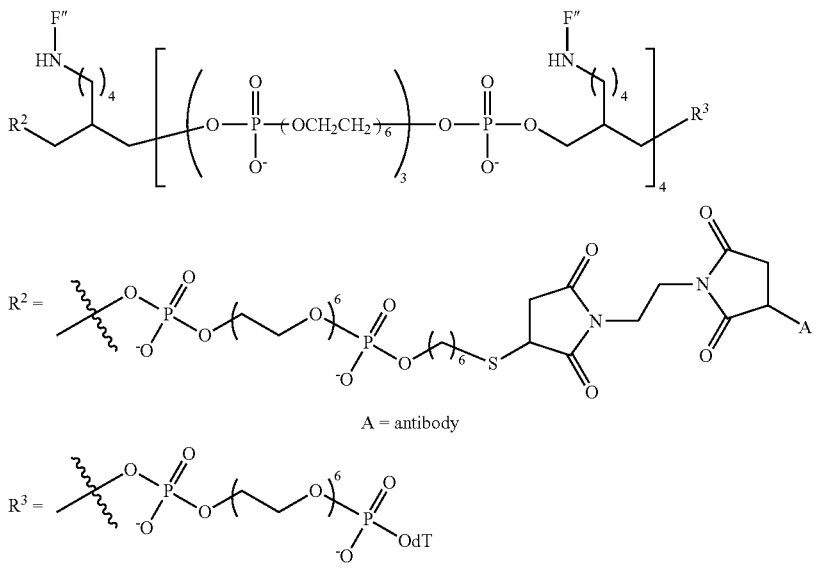 |
| I-41 | TBD | 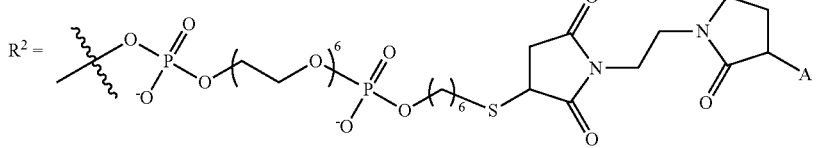 |
| I-42 | TBD | 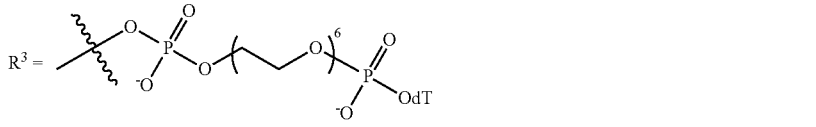 |

TABLE 2-continued

Exemplary Compounds of Structure I

| No. | MW. Found Calc. | Structure |
|---|---|---|
| I-43 | 3103.9 3103.6 | 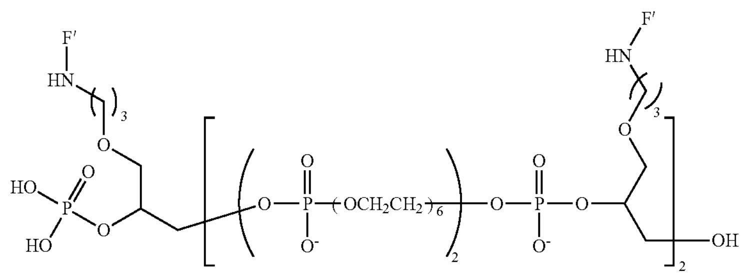 |
| I-44 | 5619.5 5619.8 | 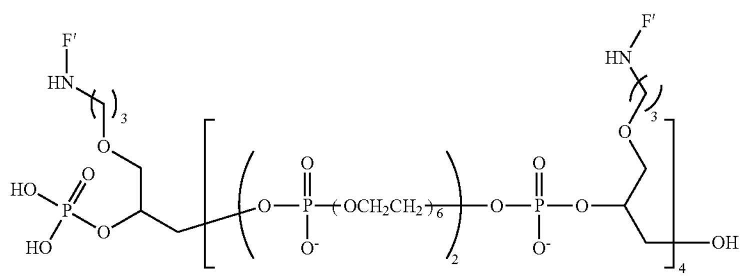 |
| I-45 | 15684.6 15681.5 | 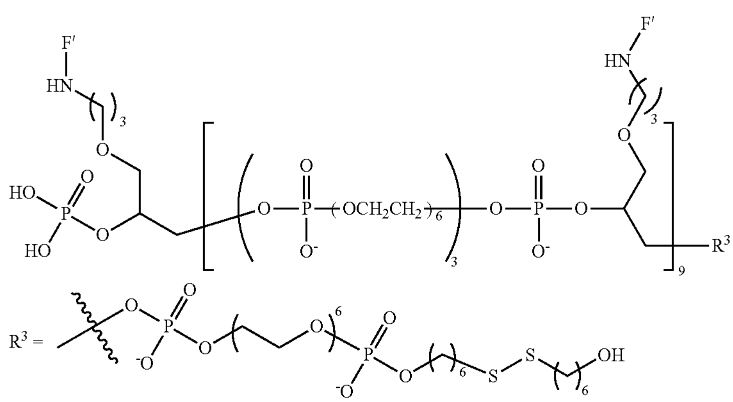 |
| I-46 | 6997.1 6997.0 | 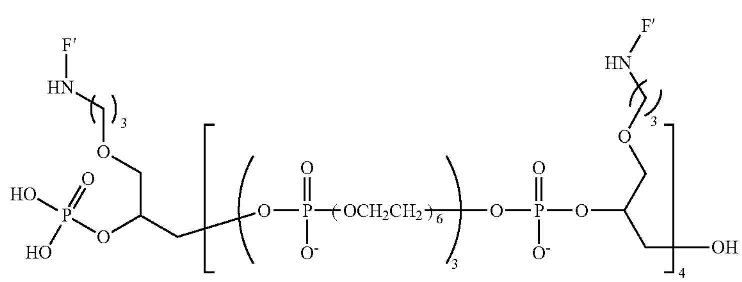 |
| I-47 | 11912.1 11910.1 | 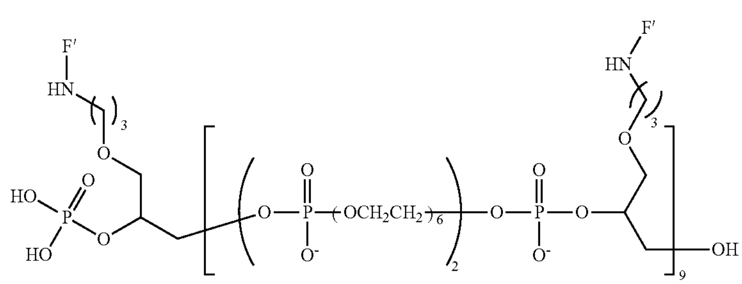 |

TABLE 2-continued

Exemplary Compounds of Structure I

| No. | MW. Found Calc. | Structure |
|---|---|---|
| I-48 | 9273.9 9272.0 | 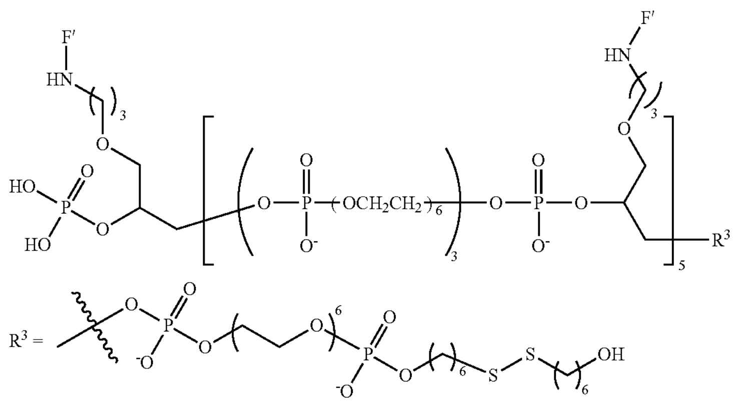 |
| I-49 | 16252.9 16250.0 | 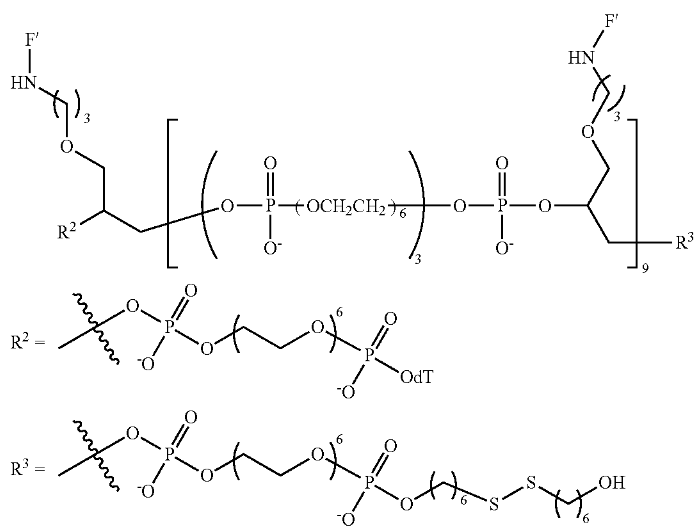 |
| I-50 | 17260.3 17260.0 | 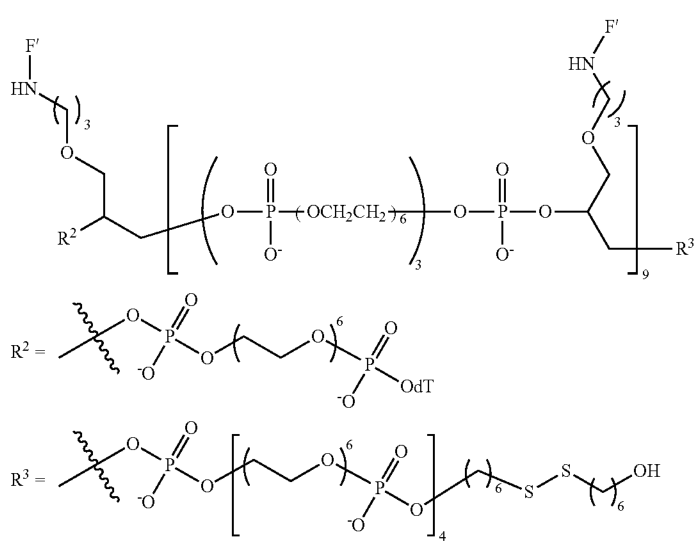 |

TABLE 2-continued
Exemplary Compounds of Structure I
| No. | MW. Found Calc. | Structure |
|---|---|---|
| I-51 | TBD | 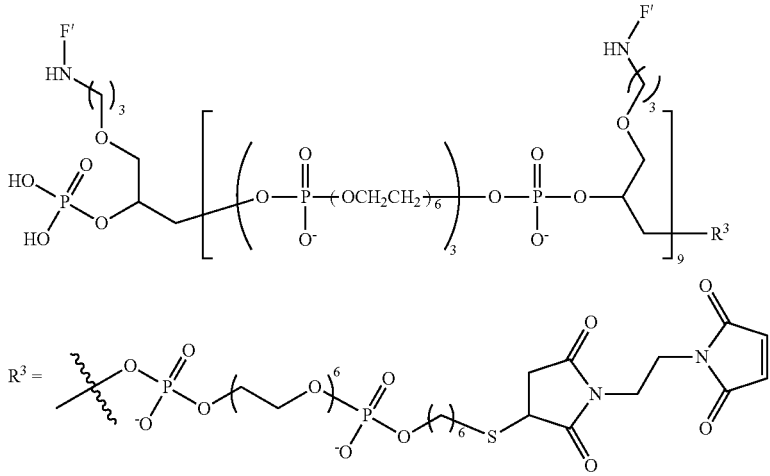 |
| I-52 | TBD | 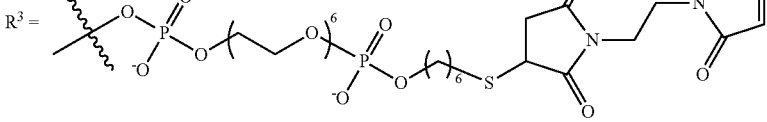 |
| I-53 | TBD | 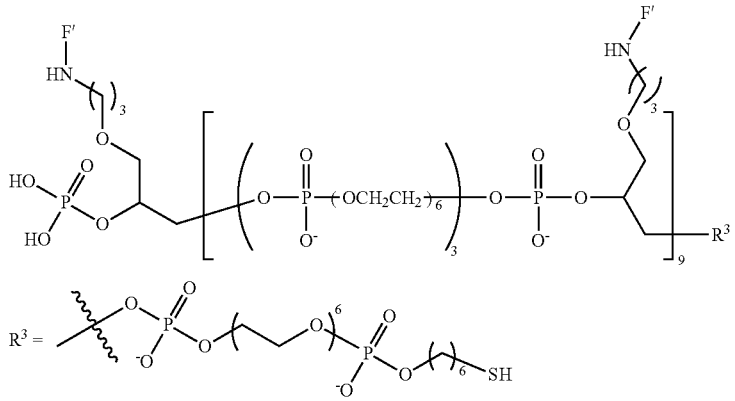 |

TABLE 2-continued
Exemplary Compounds of Structure I
| No. | MW. Found Calc. | Structure |
|---|---|---|
| I-54 | TBD | 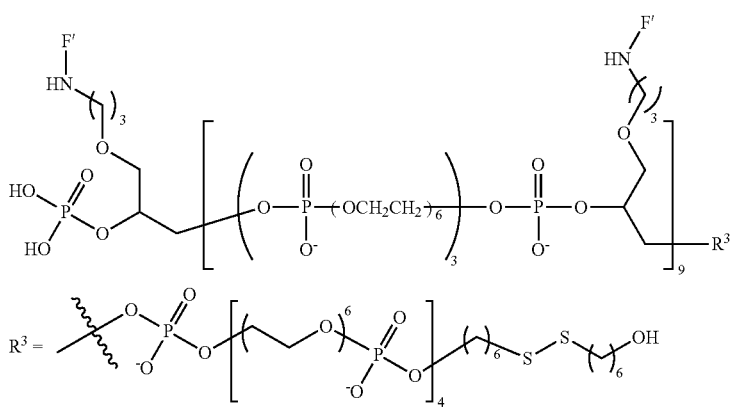 |
| I-55 | TBD | 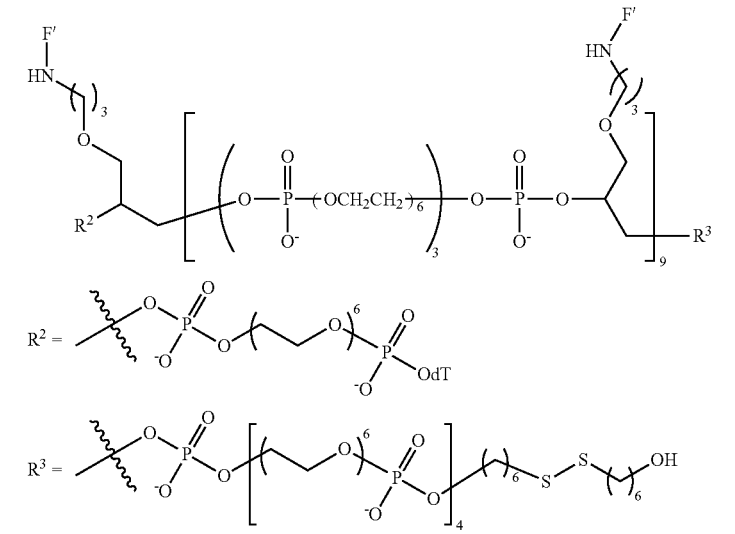 |
| I-56 | TBD | 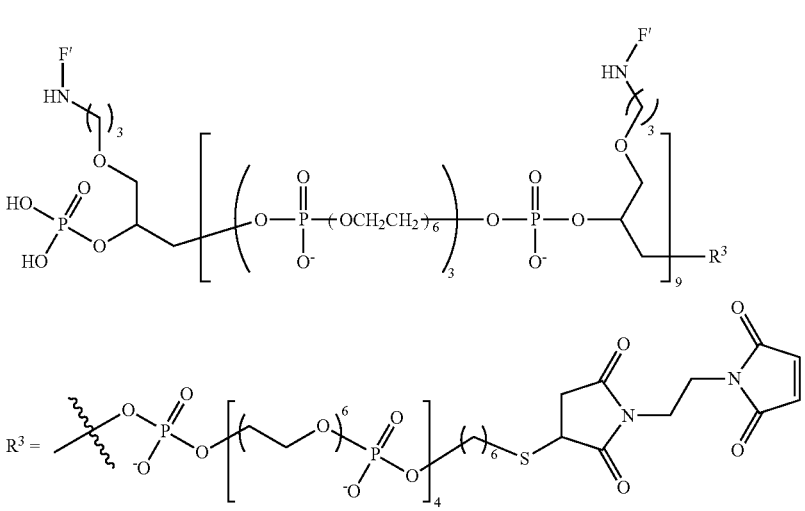 |

TABLE 2-continued
Exemplary Compounds of Structure I
| No. | MW. Found Calc. | Structure |
|---|---|---|
| I-57 | TBD | 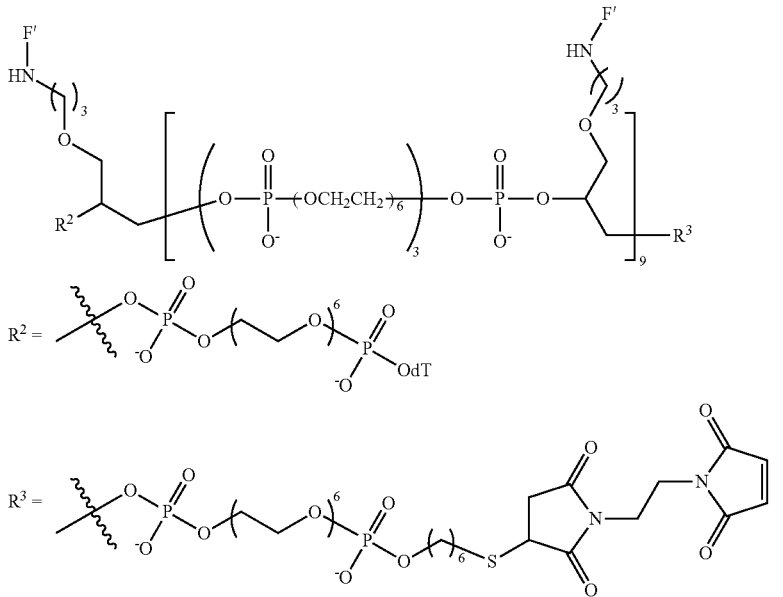 |
| I-58 | TBD | 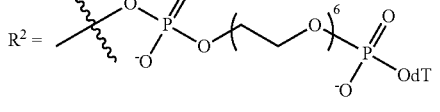 |
| I-59 | TBD | 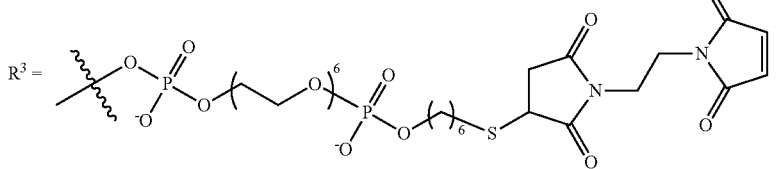 |

TABLE 2-continued

Exemplary Compounds of Structure I

| No. | MW. Found Calc. | Structure |
|---|---|---|
| | | R³ = (structure with phosphate, PEG, maleimide-antibody linker); A = antibody |
| I-60 | TBD | (structure shown below) |

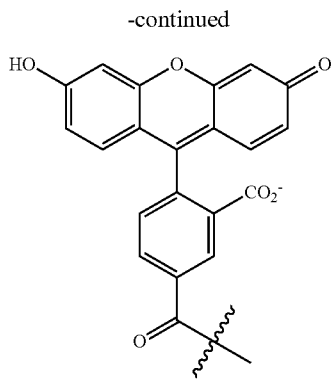

n = about 23 such that PEG M.W. = about 1,000

* TBD = to be determined

As used in Table 2 and throughout the application R², R³, m, n and L' have the definitions provided for compounds of structure (I) unless otherwise indicated, and F, F' and F" refer to a fluorescein moiety having the following structures, respectively:

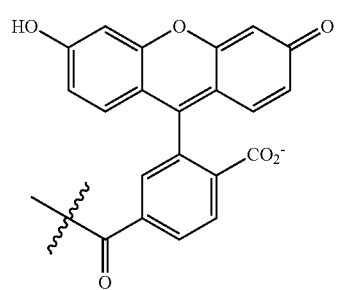

F

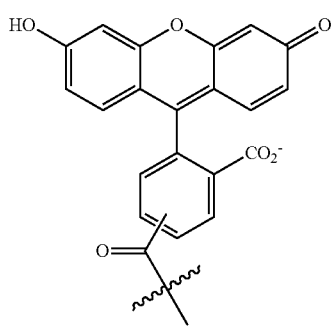

F'

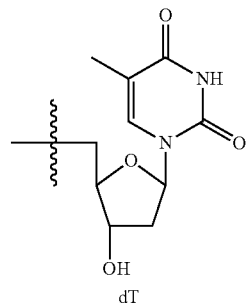 [SMILES: *CC1OC(n2cc(C)c(=O)[nH]c2=O)CC1O]

F"

"dT" refers to the following structure:

(dT structure)

dT

Some embodiments include any of the foregoing compounds, including the specific compounds provided in Table 2, conjugated to a targeting moiety, such as an antibody.

Polymeric Dye Compounds of Structure (II)

In some embodiments are provided a compound of structure (II). In some different embodiments compositions comprising a cyclodextrin and a compound of structure (II) are provided. Compounds of structure (II) have the following structure:

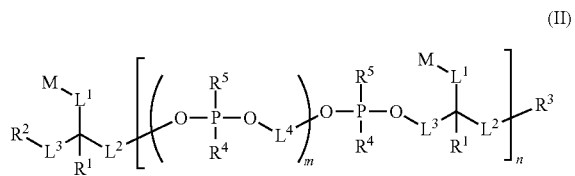

(II)

or a stereoisomer, salt or tautomer thereof, wherein:

M is, at each occurrence, independently the dye moiety;

$L^1$ is, at each occurrence, independently a linker comprising a functional group capable of formation by reaction of two complementary reactive groups;

$L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently an alkylene, alkenylene, alkynylene, heteroalkylene, heteroalkenylene or heteroalkynylene linker;

$R^1$ is, at each occurrence, independently H, alkyl or alkoxy;

$R^2$ and $R^3$ are each independently H, OH, SH, alkyl, alkoxy, alkylether, heteroalkyl, —OP(=$R_a$)($R_b$)$R_c$, Q or L';

$R^4$ is, at each occurrence, independently OH, SH, O$^-$, S$^-$, OR$_d$ or SR$_d$;

$R^5$ is, at each occurrence, independently oxo, thioxo or absent;

$R_a$ is O or S;

$R_b$ is OH, SH, O$^-$, S$^-$, OR$_d$ or SR$_d$;

$R_c$ is OH, SH, O$^-$, S$^-$, OR$_d$, OL', SR$_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected analogue thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

m is, at each occurrence, independently an integer of zero or greater; and n is an integer of one or greater.

In other embodiments of structure (II):

M is, at each occurrence, independently the dye moiety;

$L^1$ is, at each occurrence, independently a linker comprising a functional group capable of formation by reaction of two complementary reactive groups;

$L^2$ and $L^3$ are, at each occurrence, independently an optional alkylene, alkenylene, alkynylene, heteroalkylene, heteroalkenylene, heteroalkynylene or heteroatomic linker;

$L^4$ is, at each occurrence, independently an alkylene, alkenylene, alkynylene, heteroalkylene, heteroalkenylene or heteroalkynylene linker;

$R^1$ is, at each occurrence, independently H, alkyl or alkoxy;

$R^2$ and $R^3$ are each independently H, OH, SH, alkyl, alkoxy, alkylether, —OP(=$R_a$)($R_b$)$R_c$, Q, a linker comprising a covalent bond to Q, a linker comprising a covalent bond to an analyte molecule, a linker comprising a covalent bond to a solid support or a linker comprising a covalent bond to a further compound of structure (II), wherein: $R_a$ is O or S; $R_b$ is OH, SH, O$^-$, S$^-$, OR$_d$ or SR$_d$; $R_c$ is OH, SH, O$^-$, S$^-$, OR$_d$, SR$_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion;

$R^4$ is, at each occurrence, independently OH, SH, O$^-$, S$^-$, OR$_d$ or SR$_d$;

$R^5$ is, at each occurrence, independently oxo, thioxo or absent;

Q is, at each occurrence, independently a moiety comprising a reactive group capable of forming a covalent bond with an analyte molecule, a solid support or a complementary reactive group Q';

m is, at each occurrence, independently an integer of zero or greater; and n is an integer of one or greater.

In some embodiments, at least one occurrence of m is an integer of one or greater. In other embodiments, at least one occurrence of m is an integer of two or greater. In still different embodiments, at least one occurrence of m is an integer of three or greater. In still different embodiments, at least one occurrence of m is an integer of four or greater. In still different embodiments, at least one occurrence of m is an integer of five or greater.

The various linkers and substituents (e.g., M, Q, $R^1$, $R^2$, $R^3$, $R_c$ $L^1$, $L^2$, $L^3$ and $L^4$) in the compound of structure (II) are optionally substituted with one more substituent as described above with respect to structure (I).

The linker $L^1$ in the compound of structure (II) is as defined in any of the embodiments of structure (I) set forth above.

Accordingly, in some embodiments the polymeric dye compound has the following structure (IIA):

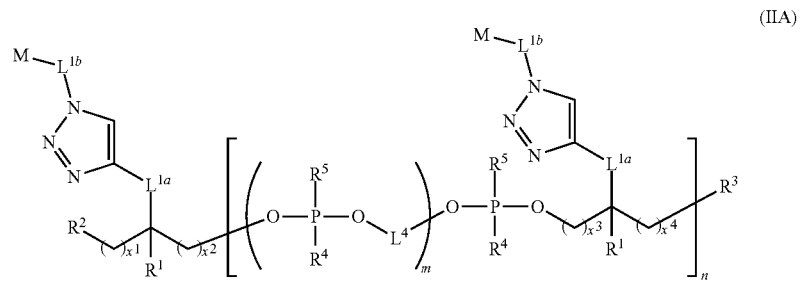

(IIA)

wherein:

$L^{1a}$ and $L^{1b}$ are, at each occurrence, independently optional linkers; and $x^1$, $x^2$, $x^3$ and $x^4$ are, at each occurrence, independently an integer from 0 to 6.

In different embodiments, the compound of structure (II) has the following structure (IIB):

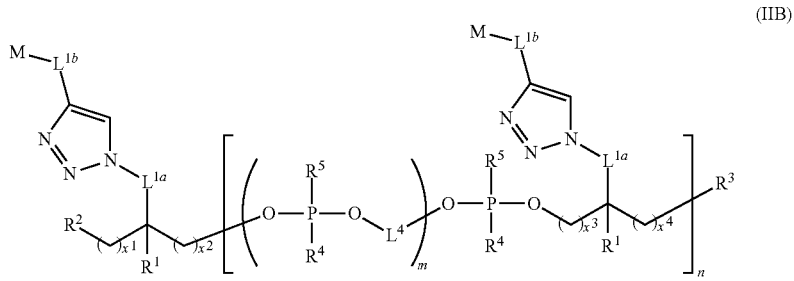

(IIB)

wherein:

$L^{1a}$ and $L^{1b}$ are, at each occurrence, independently optional linkers; and $x^1$, $x^2$, $x^3$ and $x^4$ are, at each occurrence, independently an integer from 0 to 6.

In various embodiments of the foregoing, $L^{1a}$ or $L^{1b}$, or both, is absent.

In other embodiments, $L^{1a}$ or $L^{1b}$, or both, is present.

In some embodiments $L^{1a}$ and $L^{1b}$, when present, are each independently alkylene or heteroalkylene. For example, in some embodiments $L^{1a}$ and $L^{1b}$, when present, independently have one of the following structures:

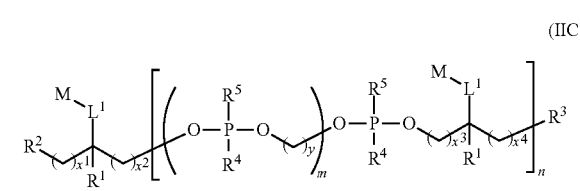

In more embodiments, $L^1$, $L^2$, $L^3$ and $L^4$ are, at each occurrence, independently $C_1$-$C_6$ alkylene, $C_2$-$C_6$ alkenylene or $C_2$-$C_6$ alkynylene. In other embodiments, $L^4$ is, at each occurrence, independently $C_1$-$C_6$ alkylene, $C_2$-$C_6$ alkenylene or $C_2$-$C_6$ alkynylene. For example, in some embodiments the compound has the following structure (IIC):

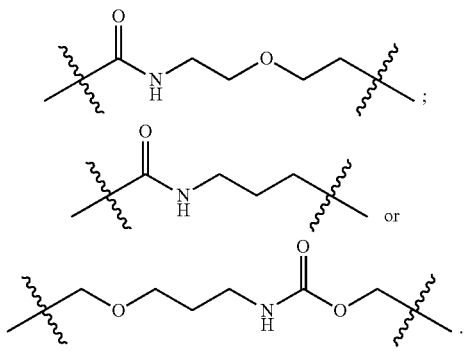

(IIC)

wherein:

$x^1$, $x^2$, $x^3$ and $x^4$ are, at each occurrence, independently an integer from 0 to 6; and y is, at each occurrence, independently an integer from 1 to 6.

In some embodiments of structure (IIC), $L^1$, at each occurrence, independently comprises a triazolyl functional group. In other embodiments of (IIC), y is 2 for each integral value of m.

In certain embodiments of the compound of structure (IIC), $x^3$ and $x^4$ are both 2 at each occurrence. In other embodiments, $x^1$, $x^2$, $x^5$ and $x^6$ are each 1 at each occurrence. In different embodiments, $x^2$ and $x^4$ are each 0, and $x^3$ is 1.

In still other embodiments of any of the foregoing compounds of structure (II), $R^4$ and $R^5$ are independent as defined for structure (I) above.

In still different embodiments, the compound of structure (II) has one of the following structures (ID) or (IE):

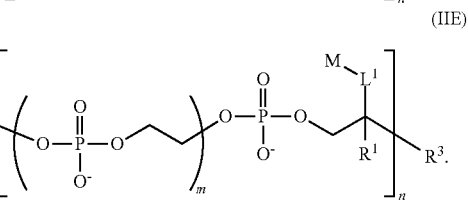

(IID)

(IIE)

In some specific embodiments of (IID) and (IIE), $L^1$, at each occurrence, independently comprises a triazolyl functional group.

$R^1$, $R^2$, $R^3$, Q, M, m and n in structure (II) are independently as defined in any of the foregoing embodiments of structure (I).

In still more different embodiments of any of the foregoing compounds of structure (II), $R^2$ and $R^3$ are each independently —OP(=$R_a$)($R_b$)$R_c$. In some of these embodiments, $R_c$ is OL'.

In other embodiments, $R^2$ and $R^3$ are each independently —OP(=$R_a$)($R_b$)OL', and L' is an alkylene or heteroalkylene linker to: Q, a targeting moiety, an analyte (e.g., analyte molecule), a solid support, a solid support residue, a nucleoside or a further compound of structure (II).

The linker L' can be any linker suitable for attaching Q, a targeting moiety, an analyte (e.g., analyte molecule), a solid support, a solid support residue, a nucleoside or a further compound of structure (II) to the compound of structure (II). Certain embodiments include use of L' moieties selected to increase or optimize water solubility of the compound. In certain embodiments, L' is a heteroalkylene moiety. In some other certain embodiments, L' comprises an alkylene oxide or phosphodiester moiety, or combinations thereof.

In certain embodiments, L' has the following structure:

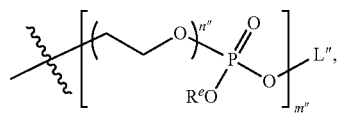

wherein:

m" and n" are independently an integer from 1 to 10;

$R^e$ is H, an electron pair or a counter ion;

L" is $R^e$ or a direct bond or linkage to: Q, a targeting moiety, an analyte (e.g., analyte molecule), a solid support, a solid support residue, a nucleoside or a further compound of structure (II).

In some embodiments, m" is an integer from 4 to 10, for example 4, 6 or 10. In other embodiments n" is an integer from 3 to 6, for example 3, 4, 5 or 6.

In some other embodiments, L" is an alkylene or heteroalkylene moiety. In some other certain embodiments, L" comprises an alkylene oxide, phosphodiester moiety, sulfhydryl, disulfide or maleimide moiety or combinations thereof.

In certain of the foregoing embodiments, the targeting moiety is an antibody or cell surface receptor antagonist.

In other more specific embodiments of any of the foregoing compounds of structure (II), $R^2$ or $R^3$ has one of the following structures:

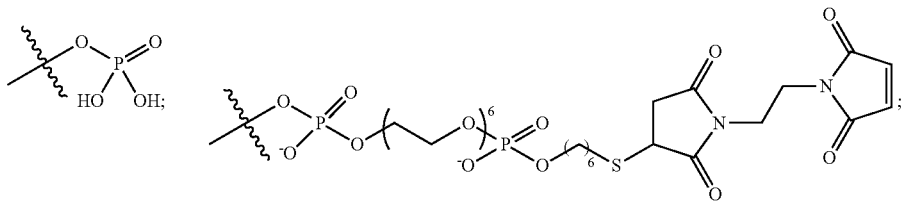

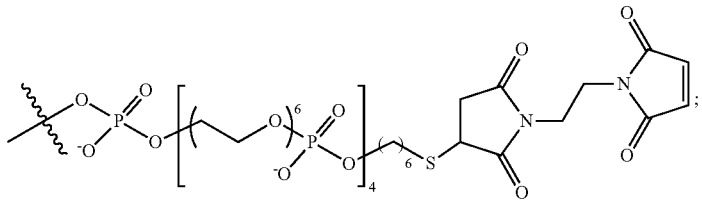

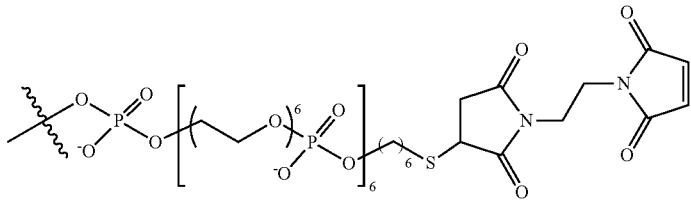

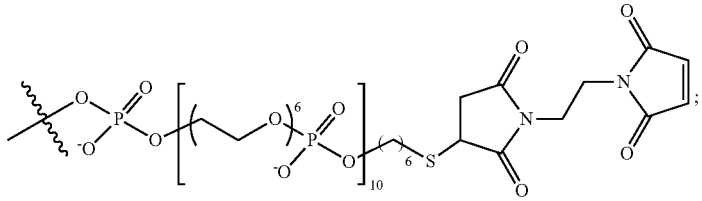

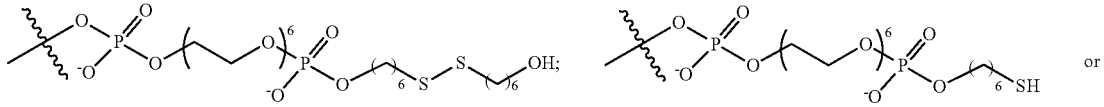

or

-continued

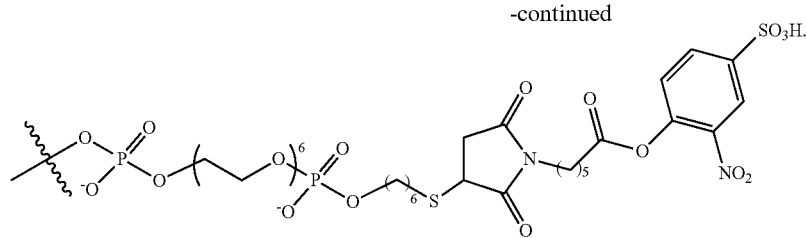

Certain embodiments of compounds of structure (II) can be prepared according to solid-phase synthetic methods analogous to those known in the art for preparation of oligonucleotides. Accordingly, in some embodiments, L' is a linkage to a solid support, a solid support residue or a nucleoside. Solid supports comprising an activated deoxythymidine (dT) group are readily available, and in some embodiments can be employed as starting material for preparation of compounds of structure (II). Accordingly, in some embodiments $R^2$ or $R^3$ has the following structure:

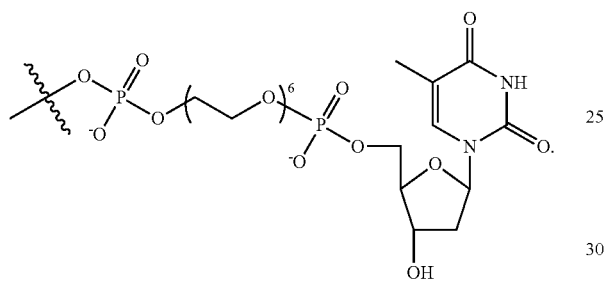

One of skill in the art will understand that the dT group depicted above is included for ease of synthesis and economic efficiencies only, and is not required. Other solid supports can be used and would result in a different nucleoside or solid support residue being present on L', or the nucleoside or solid support residue can be removed or modified post synthesis.

In some specific embodiments, the compound of structure (II) is a compound selected from Table 3:

TABLE 3

Exemplary Compounds of Structure II

| Name | Structure |
|---|---|
| II-1 | 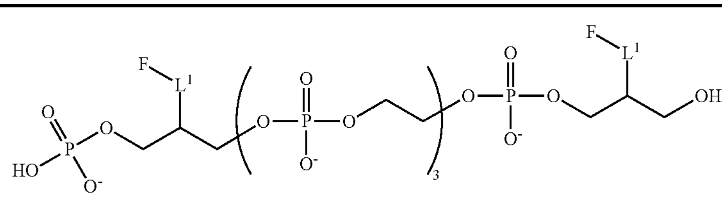 |
| II-2 | 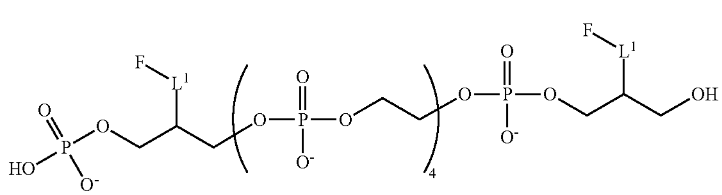 |

TABLE 3-continued

Exemplary Compounds of Structure II

| Name | Structure |
|---|---|
| II-3 | (structure with subscript 5) |
| II-4 | (structure with subscript 6) |
| II-5 | (structure with subscript 7) |
| II-6 | (structure with subscript 8) |
| II-7 | (structure with subscript 9) |
| II-8 | (structure with subscript 3) |
| II-9 | (structure with subscript 4) |
| II-10 | (structure with subscript 5) |

TABLE 3-continued

Exemplary Compounds of Structure II

| Name | Structure |
|---|---|
| II-11 | 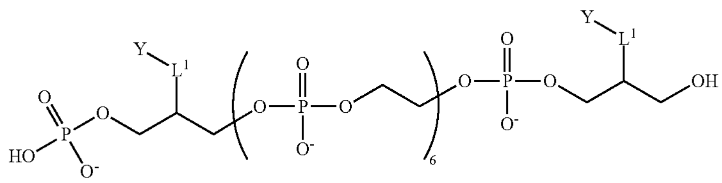 |
| II-12 | 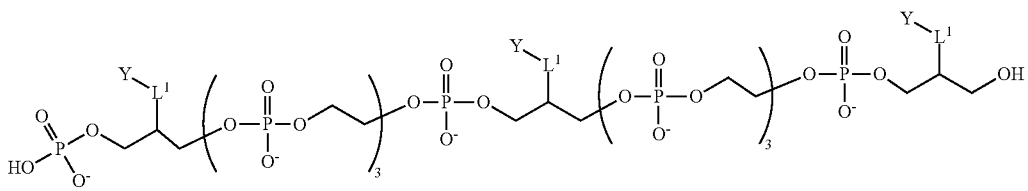 |
| II-13 | 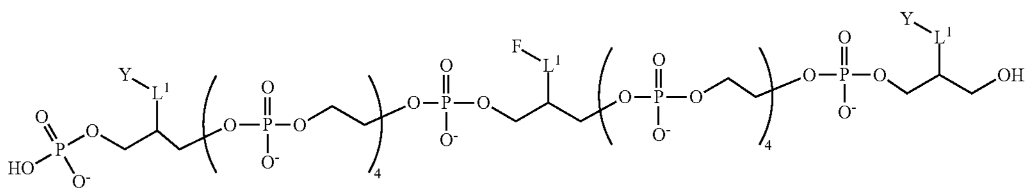 |
| II-14 | 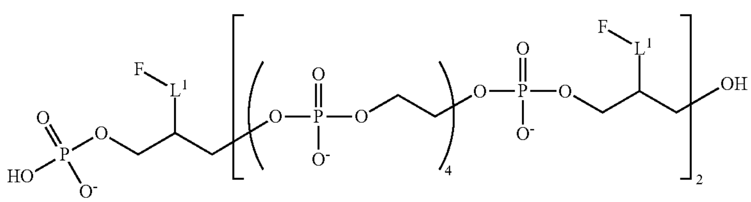 |
| II-15 | 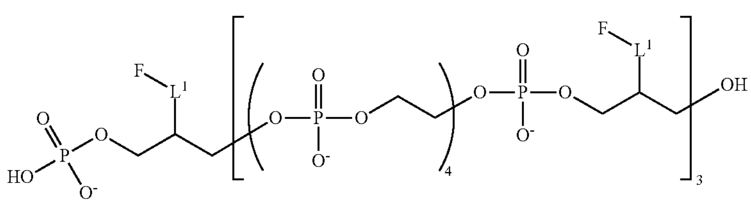 |
| II-16 | 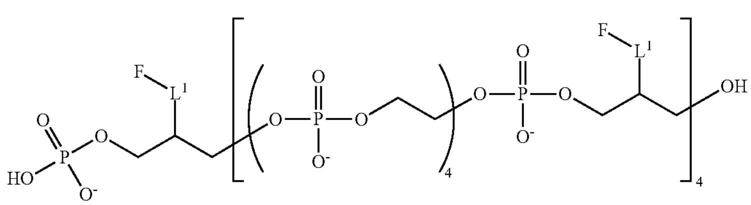 |
| II-17 | 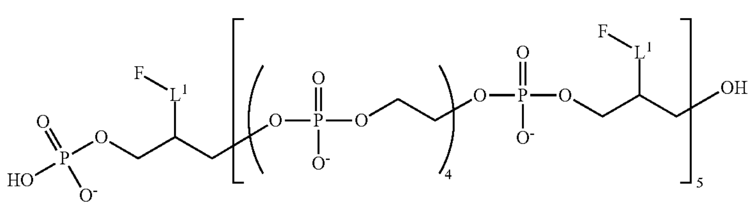 |

TABLE 3-continued

Exemplary Compounds of Structure II

| Name | Structure |
|---|---|
| II-18 | 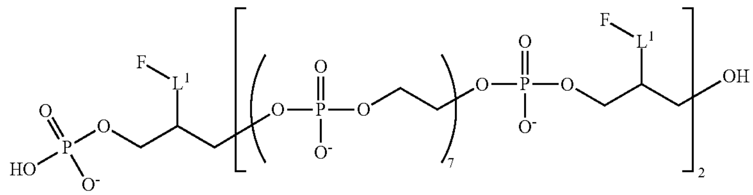 |
| II-19 | 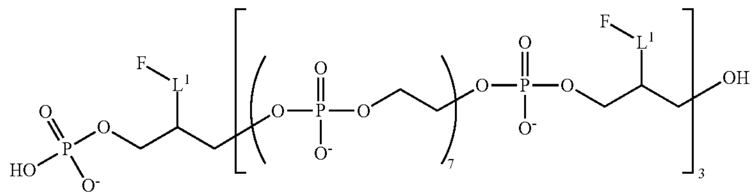 |
| II-20 | 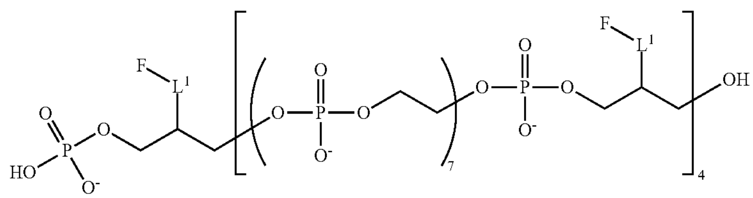 |
| II-21 | 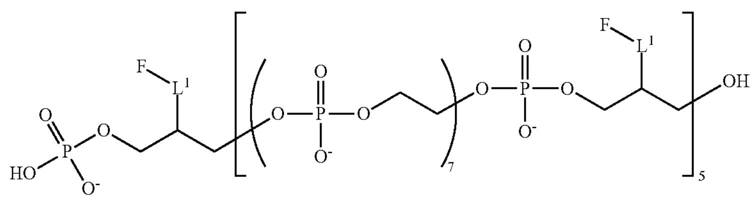 |
| II-22 | 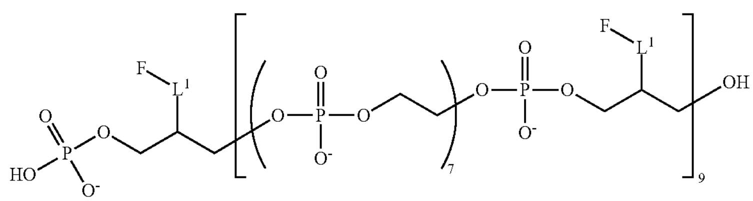 |
| II-23 | 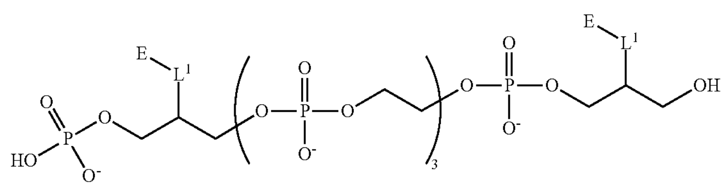 |
| II-24 | 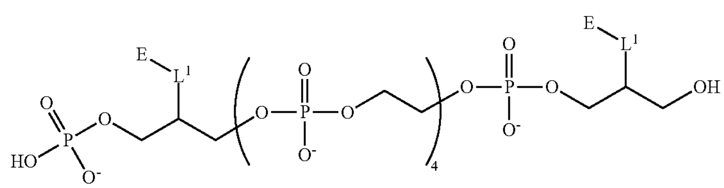 |
| II-25 | 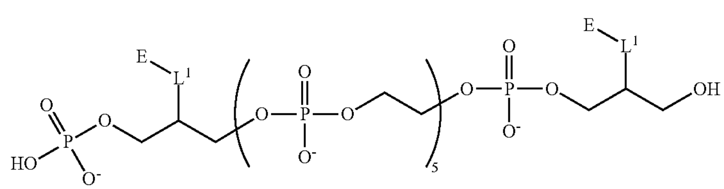 |

TABLE 3-continued

Exemplary Compounds of Structure II

| Name | Structure |
|---|---|
| II-26 | 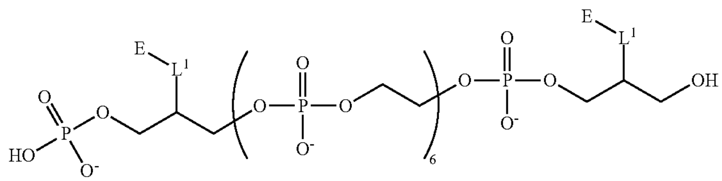 |
| II-27 | 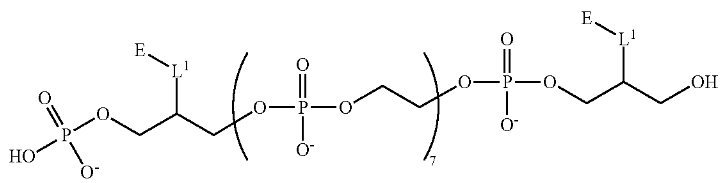 |
| II-28 | 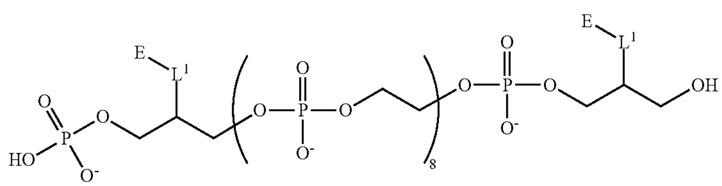 |
| II-29 | 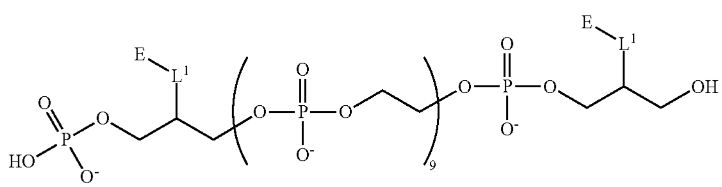 |
| II-30 | 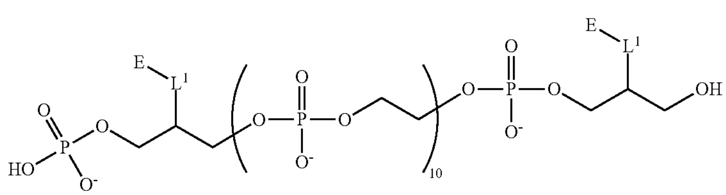 |
| II-31 | 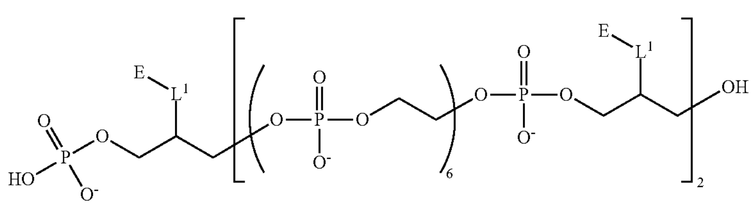 |
| II-32 | 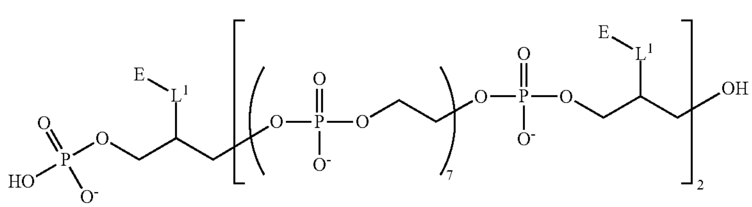 |

TABLE 3-continued

Exemplary Compounds of Structure II

| Name | Structure |
|---|---|
| II-33 | 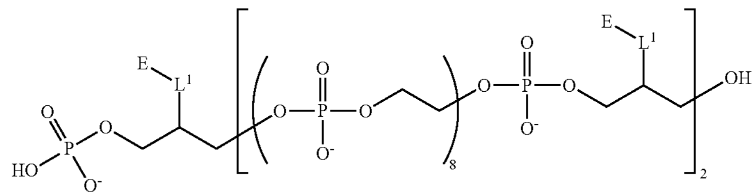 |
| II-34 | 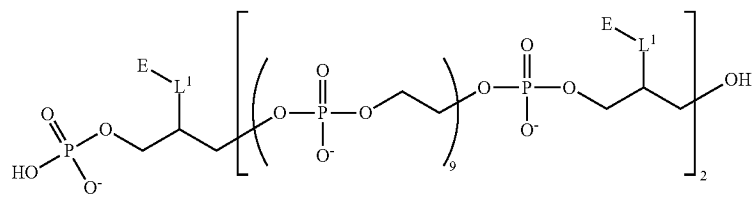 |
| II-35 | 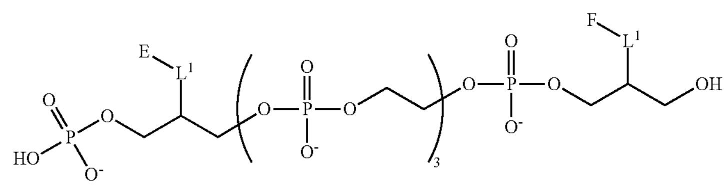 |
| II-36 | 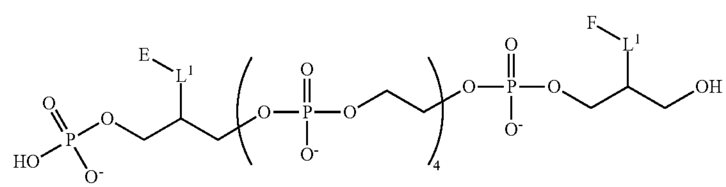 |
| II-37 | 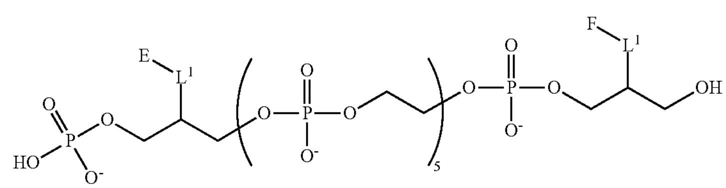 |
| II-38 | 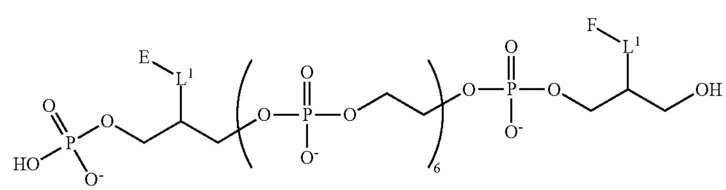 |

As used in Table 3, and throughout the application, F, E and Y refer to fluorescein, perylene and pyrene moieties, respectively, and have the following structures:

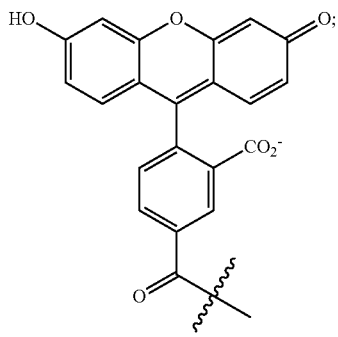
"F"

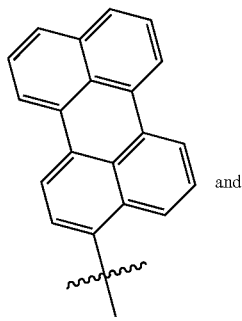
"E" and

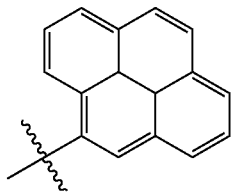
"Y"

Polymeric Dye Compounds of Structure (III)

In some embodiments are provided a compound of structure (III). In some different embodiments compositions comprising a cyclodextrin and a compound of structure (III) are provided. Compounds of structure (III) have the following structure:

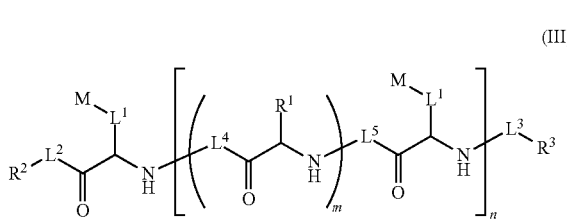
(III)

or a stereoisomer, salt or tautomer thereof, wherein:

M is, at each occurrence, independently the dye moiety;

$L^1$ is at each occurrence, independently either: i) an optional alkylene, alkenylene, alkynylene, heteroalkylene, heteroalkenylene or heteroalkynylene linker; or ii) a linker comprising a functional group capable of formation by reaction of two complementary reactive groups;

$L^2$, $L^3$, $L^4$ and $L^5$ are, at each occurrence, independently optional alkylene, alkenylene, alkynylene, heteroalkylene, heteroalkenylene or heteroalkynylene linkers;

$R^1$ is, at each occurrence, independently a natural or unnatural amino acid side chain;

$R^2$ and $R^3$ are each independently H, —OH, —SH, —NH$_2$, —CO$_2$H, alkyl, alkylether, alkoxy, heteroalkyl, alkylaminyl, alkylcarbonyl, alkyloxycarbonyl, Q, a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue or a linker comprising a covalent bond to a further compound of structure (I), wherein the alkyl, alkylether, alkylaminyl, alkylcarbonyl and alkyloxycarbonyl are optionally substituted with hydroxyl, amino, sulfhydryl, phosphate, thiophosphate, phosphoalkyl, thiophosphoalkyl, phosphoalkylether or thiophosphoalkylether, or combinations thereof; Q is, at each occurrence, independently a moiety comprising a reactive group capable of forming a covalent bond with an analyte molecule, a solid support or a complementary reactive group Q';

m is, at each occurrence, independently an integer of zero or greater; and n is an integer of one or greater.

In other embodiments of structure (III):

M is, at each occurrence, independently the dye moiety;

$L^1$ is at each occurrence, independently either: i) an optional alkylene, alkenylene, alkynylene, heteroalkylene, heteroalkenylene or heteroalkynylene linker; or ii) a linker comprising a functional group capable of formation by reaction of two complementary reactive groups;

$L^2$, $L^3$, $L^4$ and $L^5$ are, at each occurrence, independently optional alkylene, alkenylene, alkynylene, heteroalkylene, heteroalkenylene or heteroalkynylene linkers;

$R^1$ is, at each occurrence, independently a natural or unnatural amino acid side chain;

$R^2$ and $R^3$ are each independently H, —OH, —SH, —NH$_2$, —CO$_2$H, alkyl, alkylether, alkylaminyl, alkylcarbonyl, alkyloxycarbonyl, Q, a linker comprising a covalent bond to Q, a linker comprising a covalent bond to an analyte molecule, a linker comprising a covalent bond to a solid support or a linker comprising a covalent bond to a further compound of structure (III), wherein the alkyl, alkylether, alkylaminyl, alkylcarbonyl and alkyloxycarbonyl are optionally substituted with hydroxyl, amino, sulfhydryl, phosphate, thiophosphate, phosphoalkyl, thiophosphoalkyl, phosphoalkylether or thiophosphoalkylether, or combinations thereof;

Q is, at each occurrence, independently a moiety comprising a reactive group capable of forming a covalent bond with an analyte molecule, a solid support or a complementary reactive group Q';

m is, at each occurrence, independently an integer of zero or greater; and n is an integer of one or greater.

The various linkers and substituents (e.g., M, Q, $R^1$, $R^2$, $R^3$, $L^1$, $L^2$, $L^3$, $L^4$ and $L^5$) in the compound of structure (I) are optionally substituted with one more substituent as described above with respect to structure (I).

The optional linker $L^1$ in the compound of structure (III) is as defined in any of the embodiments of structure (I) set forth above.

In some embodiments, at least one $R^1$ is a neutral amino acid side chain, for example H or alkyl.

In other embodiments of structure (III), at least one $R^1$ is a charged amino acid side chain, for example a side chain comprising an amidinyl, guanidinyl or imidazolyl group.

In other embodiments, R¹ is, at each occurrence, independently H, alkyl, —CH₂CO₂—, —CH₂CH₂CO₂—, —CH₂CH₂CH₂CH₂NH₃+, —CH₂CH₂CH₂NHC(=NH₂+) NH₂ or imidazolyl.

In various other embodiments, R¹, L⁴ and m are selected such that

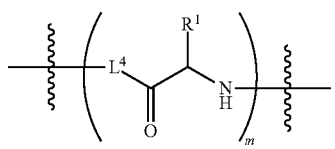

has an amino acid sequence of (G)₁₀, (GDGDGDGDGD) or (GKGKGKGKGK).

In different embodiments, R¹, L⁴ and m are selected such that

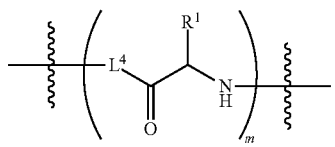

m has an amino acid sequence capable of forming an α-helix or β-sheet secondary structure. For example, in some embodiments the amino acid sequence is (GGEEFMLVYK-FARKHGG) or (GGMSMVVSGG).

In different embodiments, L⁴ and L⁵ are absent at each occurrence. In other embodiments, L⁴ or L⁵, or both, is present for at least one occurrence. For example, in some embodiments, when present, L⁴ or L⁵, or both, is a heteroalkylene linker.

L⁴ and/or L⁵ can include charged moieties. For example, in some embodiments, L⁴ and/or L⁵ is a heteroalkylene linker comprising a functional group capable of maintaining a positive or negative charge at pH values ranging from 3 to 11 in aqueous solution. in some embodiments, L⁴ and/or L⁵ is a heteroalkylene linker comprising a functional group capable of maintaining a positive charge at pH values ranging from 3 to 11 in aqueous solution. in some embodiments, L⁴ and/or L⁵ is a heteroalkylene linker comprising a functional group capable of maintaining a negative charge at pH values ranging from 3 to 11 in aqueous solution.

In some embodiments, at least one occurrence of L⁴ or L⁵, or both, has the following structure:

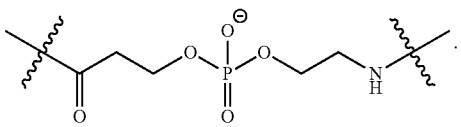 [SMILES: *NCCOP(=O)([O-])OCCC(*)=O]

In other embodiments, at least one occurrence of L⁴ or L⁵, or both, has the following structure:

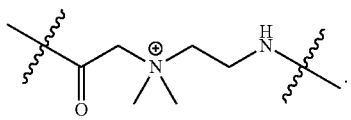 [SMILES: *NCC[N+](C)(C)CC(*)=O]

In still other different embodiments of structure (III), L¹ is at each occurrence, independently an optional alkylene or heteroalkylene linker.

In more embodiments other embodiments of structure (III), L² and L³ are, at each occurrence, independently are independently absent or a heteroalkylene linker. For example, in some embodiments the heteroalkylene linker is an amino acid or peptidyl linker.

In other various embodiments of structure (III), R² is —NH₂. In other embodiments, R³ is Q, a linker comprising a covalent bond to Q or a linker comprising a covalent bond to a solid support.

In various different embodiments of structure (III), R¹, R², R³, Q, M, m and n in structure (II) are independently as defined in any of the foregoing embodiments of structure (I).

In some specific embodiments, the compound of structure (III) is a compound selected from Table 4. The compounds in Table 4 were prepared according to the procedures set forth in the Examples and their identity confirmed by mass spectrometry.

TABLE 4

Exemplary Compounds of Structure III

| # | Structure |
|---|---|
| III-1 | 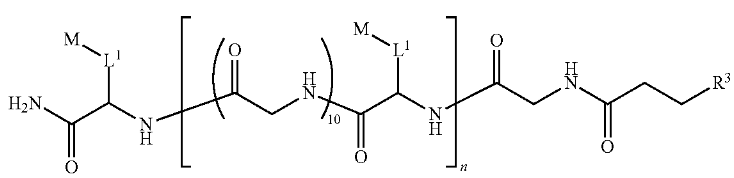 |
| III-2 | 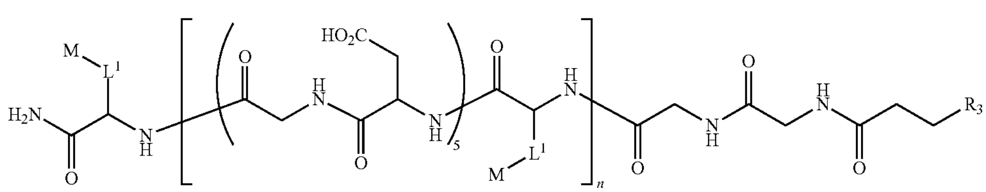 |

TABLE 4-continued

Exemplary Compounds of Structure III

| # | Structure |
|---|-----------|
| III-3 | 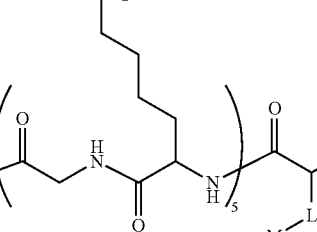 |
| III-4 | 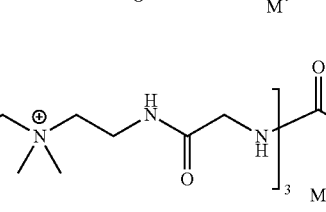 |
| III-5 | 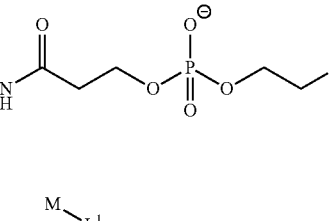 |
| III-6 | 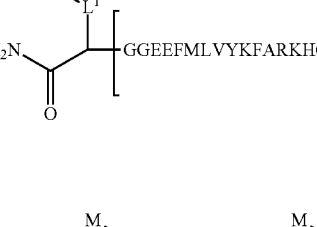 |
| III-7 | 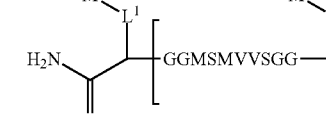 |

As used in Table 5 at entries III-6 and III-7, and where indicated throughout the application, letter sequences incorporated in structural drawings indicate amino acid sequences denoted by 1-letter codes as known in the art.

Polymeric Dye Compounds of Structure (IV)

In some embodiments are provided a compound of structure (IV). In some different embodiments compositions comprising a cyclodextrin and a compound of structure (IV) are provided. Compounds of structure (IV) have the following structure:

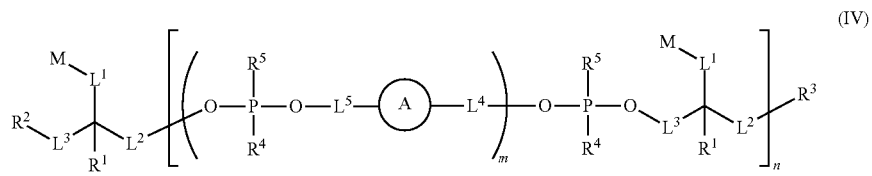

(IV)

or a stereoisomer, salt or tautomer thereof, wherein:

A is, at each occurrence, independently a moiety comprising one or more, fused, carbocyclic or heterocyclic ring system;

M is, at each occurrence, independently the dye moiety;

$L^1$ is at each occurrence, independently either: i) an optional alkylene, alkenylene, alkynylene, heteroalkylene, heteroalkenylene, heteroalkynylene or heteroatomic linker;

or ii) a linker comprising a functional group capable of formation by reaction of two complementary reactive groups;

$L^2$, $L^3$, $L^4$ and $L^5$ are, at each occurrence, independently an optional alkylene, alkenylene, alkynylene, heteroalkylene, heteroalkenylene, heteroalkynylene linker or heteroatomic linker;

$R^1$ is, at each occurrence, independently H, alkyl or alkoxy;

$R^2$ and $R^3$ are each independently H, OH, SH, alkyl, alkoxy, alkylether, heteroalkyl, —OP(=$R_a$)($R_b$)$R_c$, Q or L';

$R^4$ is, at each occurrence, independently OH, SH, O⁻, S⁻, $OR_d$ or $SR_d$;

$R^5$ is, at each occurrence, independently oxo, thioxo or absent;

$R_a$ is O or S;

$R_b$ is OH, SH, O⁻, S⁻, $OR_d$ or $SR_d$;

$R_c$ is OH, SH, O⁻, S⁻, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected analogue thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

m is, at each occurrence, independently an integer of zero or greater, provided that at least one occurrence of m is an integer of one or greater; and n is an integer of one or greater.

In other embodiments of structure (IV):

A is, at each occurrence, independently a moiety comprising one or more, fused, carbocyclic or heterocyclic ring system;

M is, at each occurrence, independently the dye moiety;

$L^1$ is at each occurrence, independently either: i) an optional alkylene, alkenylene, alkynylene, heteroalkylene, heteroalkenylene, heteroalkynylene or heteroatomic linker; or ii) a linker comprising a functional group capable of formation by reaction of two complementary reactive groups;

$L^2$, $L^3$, $L^4$ and $L^5$ are, at each occurrence, independently an optional alkylene, alkenylene, alkynylene, heteroalkylene, heteroalkenylene, heteroalkynylene linker or heteroatomic linker;

$R^1$ is, at each occurrence, independently H, alkyl or alkoxy;

$R^2$ and $R^3$ are each independently H, OH, SH, alkyl, alkoxy, alkylether, —OP(=$R_a$)($R_b$)$R_c$, Q, a linker comprising a covalent bond to Q, a linker comprising a covalent bond to an analyte molecule, a linker comprising a covalent bond to a solid support or a linker comprising a covalent bond to a further compound of structure (I), wherein: $R_a$ is O or S; $R_b$ is OH, SH, O⁻, S⁻, $OR_d$ or $SR_d$; $R_c$ is OH, SH, O⁻, S⁻, $OR_d$, $SR_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion;

$R^4$ is, at each occurrence, independently OH, SH, O⁻, S⁻, $OR_d$ or $SR_d$;

$R^5$ is, at each occurrence, independently oxo, thioxo or absent;

Q is, at each occurrence, independently a moiety comprising a reactive group capable of forming a covalent bond with an analyte molecule, a solid support or a complementary reactive group Q';

m is, at each occurrence, independently an integer of zero or greater, provided that at least one occurrence of m is an integer of one or greater; and n is an integer of one or greater.

The various linkers and substituents (e.g., M, A, Q, $R^1$, $R^2$, $R^3$, $R^c$ $L^1$, $L^2$, $L^3$, $L^4$ and $L^5$) in the compound of structure (IV) are optionally substituted with one more substituent as described above with respect to structure (I).

The optional linker $L^1$ in the compound of structure (IV) is as defined in any of the embodiments of structure (I) set forth above.

In some embodiments of structure (IV), A is at each occurrence, independently a moiety comprising one or more, fused, aryl or heteroaryl ring system. In different embodiments, A is at each occurrence, independently a moiety comprising one or more, fused, bicyclic or tricyclic, aryl or heteroaryl ring system.

In other more specific embodiments, A is, at each occurrence, independently a fused, carbocyclic or heterocyclic ring system having one of the following structures:

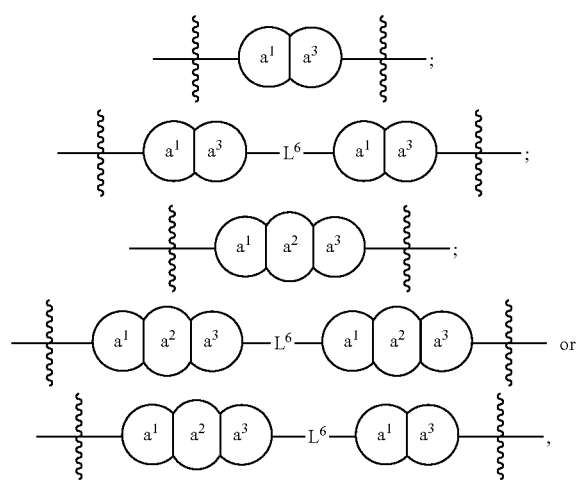

wherein:

$a^1$, $a^2$ and $a^3$ are, at each occurrence, independently a 5, 6 or 7-membered carbocyclic or heterocyclic ring; and $L^6$ is a direct bond or a linker.

In yet other embodiments A, at each occurrence, independently has one of the following structures:

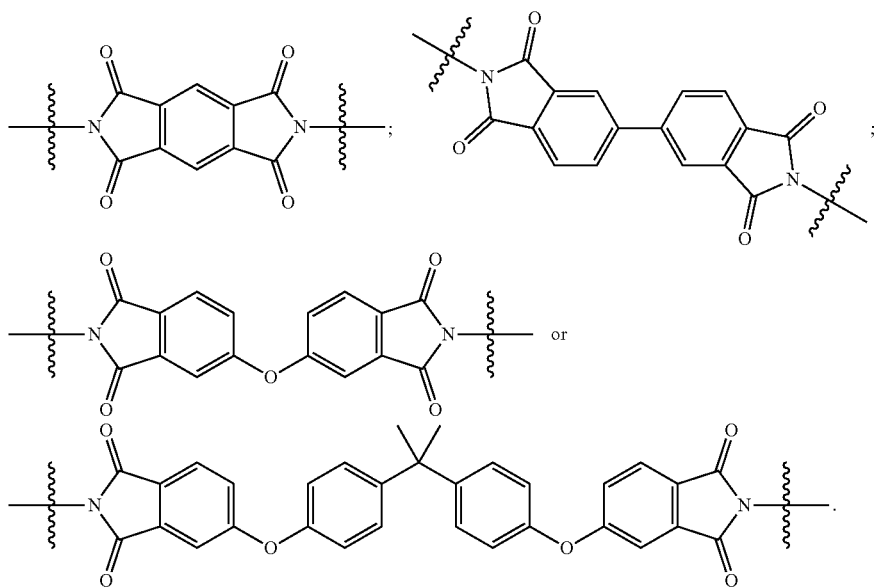

In more embodiments of structure (IV), $L^2$, $L^3$, $L^4$ and $L^5$ are, at each occurrence, independently $C_1$-$C_6$ alkylene, $C_2$-$C_6$ alkenylene or $C_2$-$C_6$ alkynylene. For example, in some embodiments the compound has the following structure (IVA):

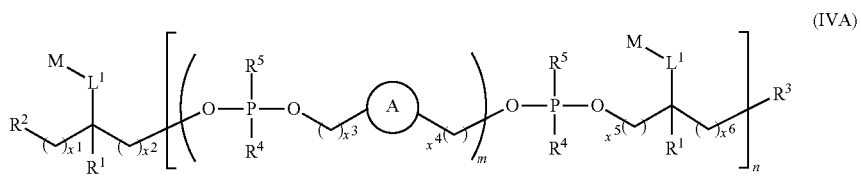

wherein:

$x^1$, $x^2$, $x^3$, $x^4$, $x^5$ and $x^6$ are, at each occurrence, independently an integer from 0 to 6.

In certain embodiments of the compound of structure (IVA), $x^3$ and $x^4$ are both 2 at each occurrence. In other embodiments, $x^1$, $x^2$, $x^5$ and $x^6$ are each 1 at each occurrence.

In some more specific embodiments of the compound of structure (IVA), $L^1$, at each occurrence, independently comprises a triazolyl functional group. In other embodiments of the compound of structure (IVA), $L^1$, at each occurrence, independently an optional alkylene or heteroalkylene linker.

In various different embodiments of structure (IV), $R^1$, $R^2$, $R^3$, Q, M, m and n in structure (IV) are independently as defined in any of the foregoing embodiments of structure (I).

In still more different embodiments of any of the foregoing compounds of structure (IV), $R^2$ and $R^3$ are each independently —OP(=$R_a$)($R_b$)$R_c$. In some of these embodiments, R is OL'.

In other embodiments, $R^2$ and $R^3$ are each independently —OP(=$R_a$)($R_b$)OL', and L' is an alkylene or heteroalkylene linker to: Q, a targeting moiety, an analyte (e.g., analyte molecule), a solid support, a solid support residue, a nucleoside or a further compound of structure (IV).

The linker L' can be any linker suitable for attaching Q, a targeting moiety, an analyte (e.g., analyte molecule), a solid support, a solid support residue, a nucleoside or a further compound of structure (IV) to the compound of structure (IV). Advantageously certain embodiments include use of L' moieties selected to increase or optimize water solubility of the compound. In certain embodiments, L' is a heteroalkylene moiety. In some other certain embodiments, L' comprises an alkylene oxide or phosphodiester moiety, or combinations thereof.

In certain embodiments, L' has the following structure:

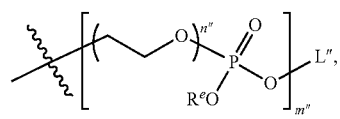

wherein:

m" and n" are independently an integer from 1 to 10;

$R^e$ is H, an electron pair or a counter ion;

L" is $R^e$ or a direct bond or linkage to: Q, a targeting moiety, an analyte (e.g., analyte molecule), a solid support, a solid support residue, a nucleoside or a further compound of structure (IV).

In some embodiments, m" is an integer from 4 to 10, for example 4, 6 or 10. In other embodiments n" is an integer from 3 to 6, for example 3, 4, 5 or 6.

In some other embodiments, L" is an alkylene or heteroalkylene moiety. In some other certain embodiments, L" comprises an alkylene oxide, phosphodiester moiety, sulfhydryl, disulfide or maleimide moiety or combinations thereof.

In certain of the foregoing embodiments, the targeting moiety is an antibody or cell surface receptor antagonist.

In other more specific embodiments of any of the foregoing compounds of structure (IV), $R^2$ or $R^3$ has one of the following structures:

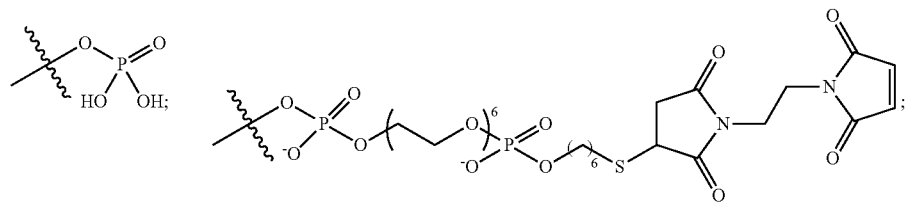
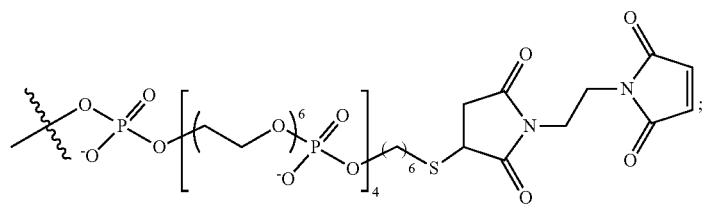
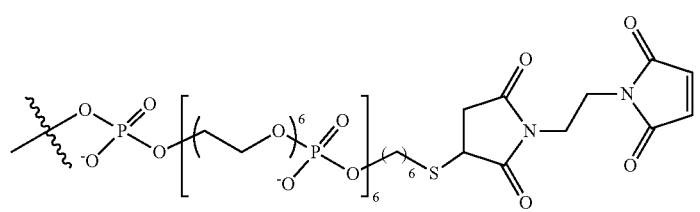
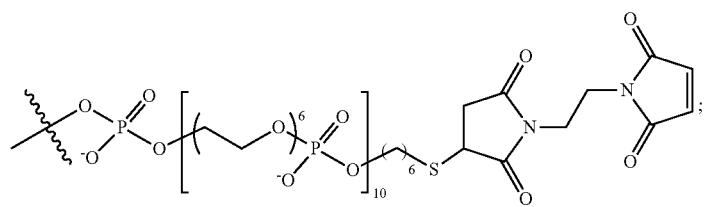
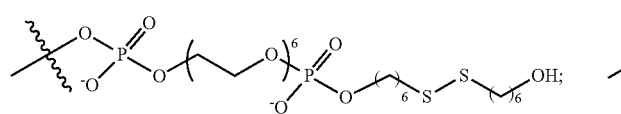
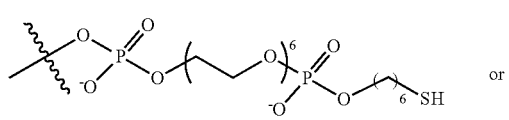
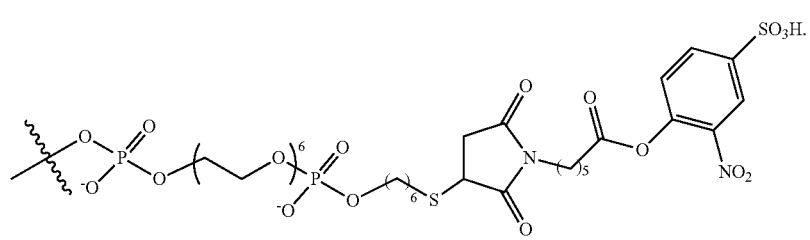

Certain embodiments of compounds of structure (IV) can be prepared according to solid-phase synthetic methods analogous to those known in the art for preparation of oligonucleotides. Accordingly, in some embodiments, L' is a linkage to a solid support, a solid support residue or a nucleoside. Solid supports comprising an activated deoxythymidine (dT) group are readily available, and in some embodiments can be employed as starting material for preparation of compounds of structure (IV). Accordingly, in some embodiments $R^2$ or $R^3$ has the following structure:

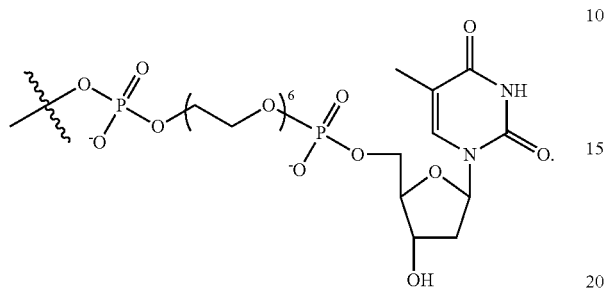

One of skill in the art will understand that the dT group depicted above is included for ease of synthesis and economic efficiencies only, and is not required. Other solid supports can be used and would result in a different nucleoside or solid support residue being present on L', or the nucleoside or solid support residue can be removed or modified post synthesis.

In some specific embodiments, the compound of structure (IV) is a compound selected from Table 5:

TABLE 5

Exemplary Compounds of Structure IV

| No. | Structure |
|---|---|
| IV-1 | 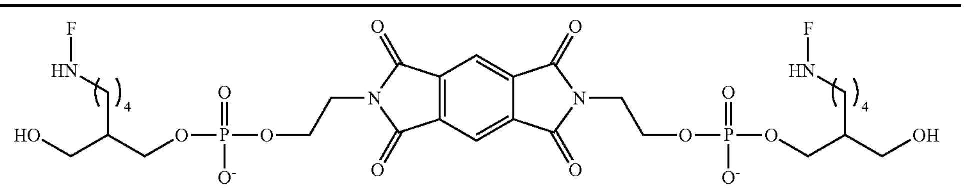 |
| IV-2 | 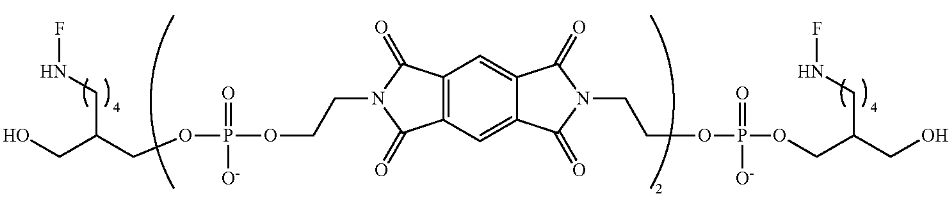 |
| IV-3 | 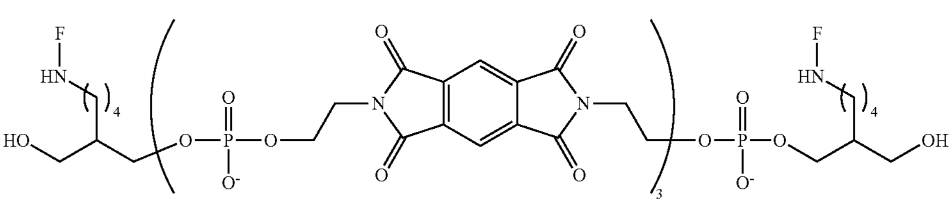 |
| IV-4 | 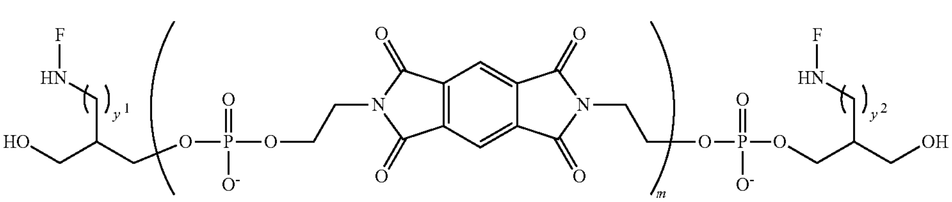 |

$m$ = 1-10; $y^1$ and $y^2$ are each independently 1 = 6

TABLE 5-continued

Exemplary Compounds of Structure IV

| No. | Structure |
| --- | --- |
| IV-5 | 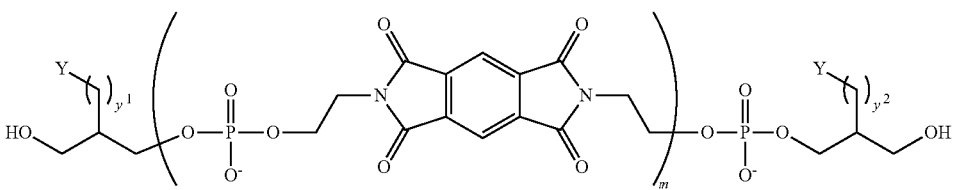<br>$m = 1\text{-}10$; $y^1$ and $y^2$ are each independently $1 = 6$ |
| IV-6 | 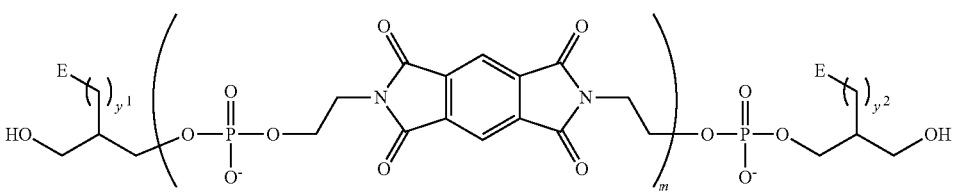<br>$m = 1\text{-}10$; $y^1$ and $y^2$ are each independently $1 = 6$ |
| IV-7 | 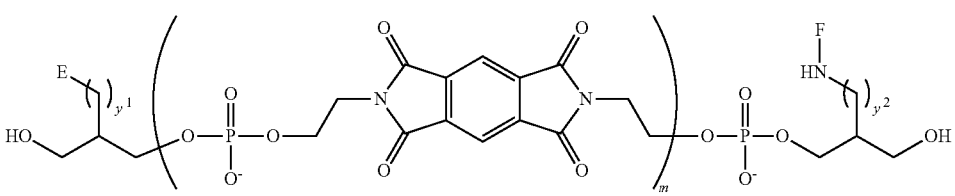<br>$m = 1\text{-}10$; $y^1$ and $y^2$ are each independently $1 = 6$ |

Molar fluorescence in certain embodiments can be expressed in terms of the fold increase or decrease relative to the fluorescence emission of the parent fluorophore (e.g., monomer). In some embodiments the molar fluorescence of the present compounds is 1.1×, 1.5×, 2×, 3×, 4×, 5×, 6×, 7×, 8×, 9×10× or even higher relative to the parent fluorophore. Various embodiments include preparing compounds having the desired fold increase in fluorescence relative to the parent fluorophore by proper selection of m and n.

For ease of illustration, various compounds comprising phosphorous moieties (e.g., phosphate and the like) are depicted in the anionic state (e.g., —OPO(OH)O$^-$, —OPO$_3^{2-}$). One of skill in the art will readily understand that the charge is dependent on pH and the uncharged (e.g., protonated or salt, such as sodium or other cation) forms are also included in the scope of embodiments of the invention.

Compositions comprising any of the foregoing compositions and one or more analyte molecules (e.g., biomolecules) are provided in various other embodiments. In some embodiments, use of such compositions in analytical methods for detection of the one or more analyte molecules are also provided.

In still other embodiments, the compositions are useful in various analytical methods. For example, in certain embodiments the disclosure provides a method of staining a sample, the method comprising adding to said sample any of the foregoing compositions, for example wherein the polymeric dye compound is a compound of structure (I), (II), (III) or (IV), for example wherein one of R$^2$ or R$^3$ is a linker comprising a covalent bond to an analyte molecule (e.g., biomolecule) or microparticle, and the other of R$^2$ or R$^3$ is H, OH, alkyl, alkoxy, alkylether or —OP(═R$_a$)(R$_b$)R$_c$, in an amount sufficient to produce an optical response when said sample is illuminated at an appropriate wavelength.

In some embodiments of the foregoing methods, R$^2$ is a linker comprising a covalent linkage to an analyte molecule, such as a biomolecule. For example, a nucleic acid, amino acid or a polymer thereof (e.g., polynucleotide or polypeptide). In still more embodiments, the biomolecule is an enzyme, receptor, receptor ligand, antibody, glycoprotein, aptamer or prion.

In yet other embodiments of the foregoing method, R$^2$ is a linker comprising a covalent linkage to a solid support such as a microparticle. For example, in some embodiments the microparticle is a polymeric bead or nonpolymeric bead.

In even more embodiments, said optical response is a fluorescent response.

In other embodiments, said sample comprises cells, and some embodiments further comprise observing said cells by flow cytometry.

In still more embodiments, the method further comprises distinguishing the fluorescence response from that of a second fluorophore having detectably different optical properties.

In other embodiments, the disclosure provides a method for visually detecting an analyte molecule, such as a biomolecule, comprising:

(a) providing any of the foregoing compositions, for example wherein the polymeric dye compound is a compound of structure (I), (II), (III) or (IV), wherein one of R$^2$ or R$^3$ is a linker comprising a covalent bond to the analyte molecule, and the other of R$^2$ or R$^3$ is H, OH, alkyl, alkoxy, alkylether or —OP(═R$_a$)(R$_b$)R$_c$; and (b) detecting the compound by its visible properties.

In some embodiments the analyte molecule is a nucleic acid, amino acid or a polymer thereof (e.g., polynucleotide or polypeptide). In still more embodiments, the analyte molecule is an enzyme, receptor, receptor ligand, antibody, glycoprotein, aptamer or prion.

In other embodiments, a method for visually detecting an analyte molecule, such as a biomolecule is provided, the method comprising:
  (a) admixing any of the foregoing compositions with one or more analyte molecules; and
  (b) detecting the compound by its visible properties.

In other embodiments is provided a method for visually detecting an analyte molecule, the method comprising:
  (a) admixing any of the foregoing compositions, for example wherein the polymeric dye compound is a compound of structure (I), (II), (III) or (IV), wherein $R^2$ or $R^3$ is Q or a linker comprising a covalent bond to Q, with the analyte molecule;
  (b) forming a conjugate of the compound and the analyte molecule; and
  (c) detecting the conjugate by its visible properties.

Other exemplary methods include a method for detecting an analyte, the method comprising:
  (a) providing a composition or polymeric dye according to any of the foregoing embodiments, wherein wherein the polymeric dye comprises a linker comprising a covalent bond to a targeting moiety having specificity for the analyte;
  (b) admixing the composition or polymeric dye and the analyte, thereby associating the targeting moiety and the analyte; and
  (c) detecting the polymeric dye, for example by its visible or fluorescent properties.

In certain embodiments of the foregoing method, the analyte is a particle, such as a cell, and the method includes use of flow cytometry. For example, the compound (i.e., polymeric dye) may be provided with a targeting moiety, such as an antibody, for selectively associating with the desired cell, thus rendering the cell detectable by any number of techniques, such as visible or fluorescence detection. Appropriate antibodies can be selected by one of ordinary skill in the art depending on the desired end use. Exemplary antibodies for use in certain embodiments include UCHT1 and MOPC-21.

Embodiments of the present compositions and polymeric dyes thus find utility in any number of methods, including, but not limited: cell counting; cell sorting; biomarker detection; quantifying apoptosis; determining cell viability; identifying cell surface antigens; determining total DNA and/or RNA content; identifying specific nucleic acid sequences (e.g., as a nucleic acid probe); and diagnosing diseases, such as blood cancers.

In some other different embodiments, the compositions can be used in various for analysis of cells. For example, by use of flow cytometry, the compounds can be used to discriminate between live and dead cells, evaluate the health of cells (e.g., necrosis vs. early apoptitic vs. late apoptitic vs. live cell), tracking ploidy and mitosis during the cell cycle and determining various states of cell proliferation. While not wishing to be bound by theory, it is believed that embodiments of certain polymeric dye compounds preferentially bind to positively charged moieties. Accordingly, in some embodiments the compositions may be used in methods for determining the presence of non-intact cells, for example necrotic cells. For example, the presence of necrotic cells can be determined by admixing a sample containing cells with a composition disclosed herein and analyzing the mixture by flow cytometry. Certain polymeric dyes disclosed herein bind to necrotic cells, and thus their presence is detectable under flow cytometry conditions. In contrast to other staining reagents which require an amine reactive group to bind to necrotic cells, embodiments of the staining methods of employing certain of the disclosed compositions do not require a protein-free incubation buffer, and thus the methods are more efficient to perform than related known methods.

For example, in one embodiment is provide a method for determining the presence of dead cells in a sample, the method comprising contacting the sample with the disclosed composition, thereby binding or associating the polymeric dye with the dead cells, and observing a fluorescent signal from the polymeric dye bound or associated with the dead cells. In some embodiments, the method further comprises use of flow cytometry to observe the polymeric dye bound or associated with the dead cells.

In various other embodiments, the compositions can be used in related methods for determining the presence of positively charged moieties in intact or non-intact cells, apoptitic bodies, depolarized membranes and/or permealized membranes.

In addition to the above methods, embodiments of the compositions find utility in various disciplines and methods, including but not limited to: imaging in endoscopy procedures for identification of cancerous and other tissues; identification of necrotic tissue by preferential binding of the compounds to dead cells; single-cell and/or single molecule analytical methods, for example detection of polynucleotides with little or no amplification; cancer imaging, for example by use of a compositions comprising a polymeric dye capable of conjugating to an antibody or sugar or other moiety that preferentially binds cancer cells; imaging in surgical procedures; binding of histones for identification of various diseases; drug delivery, for example by replacing the M moiety with an active drug moiety; and/or contrast agents in dental work and other procedures, for example by preferential binding of the polymeric dye compound to various flora and/or organisms.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diaryalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Furthermore, all compounds described herein which exist in free base or acid form can be converted to their salts by treatment with the appropriate inorganic or organic base or acid by methods known to one skilled in the art. Salts of the compounds of the invention can be converted to their free base or acid form by standard techniques.

The following Reaction Schemes illustrate exemplary methods of making polymeric dye compounds. Other methods for preparation of polymeric dye compounds are provided in PCT Pub. Nos. WO 2015/027176, WO/2016/138461 and WO/2016/183185, the full disclosure of which is hereby incorporated by reference in its entirety. It is understood that one skilled in the art may be able to make these compounds by similar methods or by combining other methods known to one skilled in the art. It is also understood that one skilled in the art would be able to make, in a similar manner as described below, other polymeric dye compounds not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

Reaction Scheme I

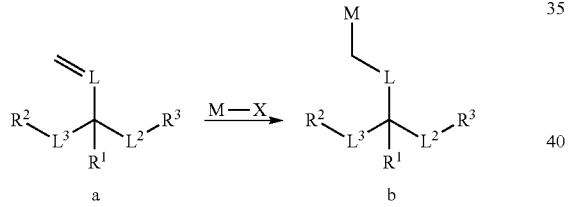

Reaction Scheme I illustrates an exemplary method for preparing an intermediate useful for preparation of compounds of structure (I), where $R^1$, $L^2$, $L^3$ and M are as defined above, $R^2$ and $R^3$ are as defined above or are protected variants thereof and L is an optional linker. Referring to Reaction Scheme 1, compounds of structure a can be purchased or prepared by methods well-known to those of ordinary skill in the art. Reaction of a with M-X, where x is a halogen such as bromo, under Suzuki coupling conditions known in the art results in compounds of structure b. Compounds of structure b can be used for preparation of compounds of structure (I) as described below.

Reaction Scheme II

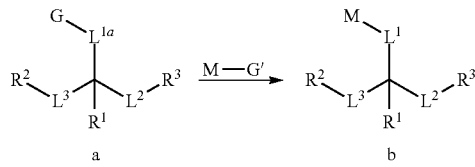

Reaction Scheme II illustrates an exemplary method for preparation of intermediates useful for preparation of polymeric dye compounds. Referring to Reaction Scheme II, where $R^1$, $L^1$, $L^2$, $L^3$, G and M are as defined above, and $R^2$ and $R^3$ are as defined above or are protected variants thereof, a compound of structure a, which can be purchased or prepared by well-known techniques, is reacted with M-G' to yield compounds of structure b. Here, G and G' represent functional groups having complementary reactivity (i.e., functional groups which react to form a covalent bond). G' may be pendant to M or a part of the structural backbone of M. G and G' may be any number of functional groups described herein, such as alkyne and azide, respectively, amine and activated ester, respectively or amine and isothiocyanate, respectively, and the like.

The polymeric dye compounds may be prepared from structure b by reaction under well-known automated DNA synthesis conditions with a phosphoramidite compound having the following structure (c):

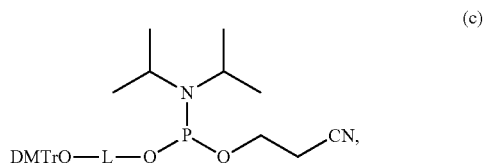

wherein L is independently an optional linker, followed by reaction with another compound of structure b. Polymeric dyes are prepared by reacting the desired number of compounds of structure b sequentially with the appropriate phosphoramidite reagent under DNA synthesis conditions.

Alternatively, the polymeric dyes are prepared by first synthesizing an dimeric or oligomeric compound having the following structure d under typical DNA synthesis conditions:

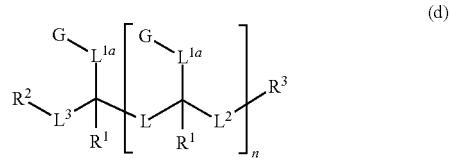

wherein G is, at each occurrence, independently a moiety comprising a reactive group capable of forming a covalent bond with a complementary reactive group G', and $L^{1a}$, $L^2$, $L^3$, $R^1$, $R^2$, $R^3$ and n are, at each occurrence, independently as defined herein for compounds of structure (I), (II), (III) or (IV), and then reacting the compound of structure d with M-$L^{1b}$-G', wherein M, $L^{1b}$ and G' are as defined herein.

DNA synthesis methods are well-known in the art. Briefly, two alcohol groups, for example $R^2$ and $R^3$ in intermediates b or d above, are functionalized with a dimethoxytrityl (DMT) group and a 2-cyanoethyl-N,N-diisopropylamino phosphoramidite group, respectively. The phosphoramidite group is coupled to an alcohol group, typically in the presence of an activator such as tetrazole, followed by oxidation of the phosphorous atom with iodine. The dimethoxytrityl group can be removed with acid (e.g., chloroacetic acid) to expose the free alcohol, which can be reacted with a phosphoramidite group. The 2-cyanoethyl group can be removed after oligomerization by treatment with aqueous ammonia.

Preparation of the phosphoramidites used in the oligomerization methods is also well-known in the art. For example, a primary alcohol (e.g., $R^3$) can be protected as a DMT group by reaction with DMT-Cl. A secondary alcohol (e.g., $R^2$) is then functionalized as a phosphoramidite by reaction with an appropriate reagent such as 2-cyanoethyl N,N-dissopropylchlorophosphoramidite. Methods for preparation of phosphoramidites and their oligomerization are well-known in the art and described in more detail in the examples.

Polymeric dyes are prepared by oligomerization of intermediate b according to the well-known phophoramidite chemistry described above. The desired number of m and n repeating units is incorporated into the molecule by repeating the phosphoramidite coupling the desired number of times. It will be appreciated that other compounds can be prepared by analogous methods.

The following examples are provided for purposes of illustration, not limitation.

EXAMPLES

General Methods $^1$H NMR spectra were obtained on a JEOL 400 MHz spectrometer. $^1$H spectra were referenced against TMS. Reverse phase HPLC analysis was performed using a Waters Acquity UHPLC system with a 2.1 mm×50 mm Acquity BEH-C18 column held at 45° C. Mass spectral analysis was performed on a Waters/Micromass Quattro micro MS/MS system (in MS only mode) using MassLynx 4.1 acquisition software. Mobile phase used for LC/MS was 100 mM 1,1,1,3,3,3-hexafluoro-2-propanol (HFIP), 8.6 mM triethylamine (TEA), pH 8. Phosphoramidites and precursor molecules were also analyzed using a Waters Acquity UHPLC system with a 2.1 mm×50 mm Acquity BEH-C18 column held at 45° C., employing an acetonitrile/water mobile phase gradient. Molecular weights for monomer intermediates were obtained using tropylium cation infusion enhanced ionization on a Waters/Micromass Quattro micro MS/MS system (in MS only mode). Size Exclusion chromatography (SEC) was accomplished with a Superdex 200 increase 5/150 GL analytical column. Isocratic elution with PBS buffer and a flow rate of 0.25 mL/min with a total run time of 17.5 min. Detection at 494, 405, 280 and 260 nm. Fractions of products were collected manually, pooled over successive runs. Lyophilized and reconstituted in 100 μL of water. Absorbance measurements were conducted on a Thermo Scientific Nanodrop 2000 spectrophotometer. Fluorescence measurements were conducted on a Thermo Scientific Nanodrop 3300 Fluorospectrometer.

All reactions were carried out in oven dried glassware under a nitrogen atmosphere unless otherwise stated. Commercially available DNA synthesis reagents were purchased from Glen Research (Sterling, Va.). Anhydrous pyridine, toluene, dichloromethane, diisopropylethyl amine, triethylamine, acetic acid, pyridine, and THF were purchased from Aldrich. All other chemicals were purchase from Aldrich or TCI and were used as is with no additional purification.

Solid-Phase Synthesis

All polymeric dye compounds were synthesized on an ABI 394 DNA synthesizer using standard protocols for the phosphoramidite based coupling approach. The chain assembly cycle for the synthesis of oligonucleotide phosphoramidates was the following: (i) detritylation, 3% trichloroacetic acid in dichloromethane, 1 min; (ii) coupling, 0.1 M phosphoramidite and 0.45 M tetrazole in acetonitrile, 10 min; (iii) capping, 0.5 M acetic anhydride in THF/lutidine, 1/1, v/v 15 s; (iv) oxidation, 0.1 M iodine in THF/pyridine/water, 10/10/1, v/v/v, 30 s.

Chemical steps within the cycle were followed by acetonitrile washing and flushing with dry argon for 0.2-0.4 min. Cleavage from the support and removal of base and phosphoramidate protecting groups was achieved by treatment with ammonia for 1 hour at room temperature. Compounds were then analyzed by reverse phase HPLC as described above.

Compounds were synthesized on an Applied Biosystems 394 DNA/RNA synthesizer or on GE AKTÄ 10 OligoPilot on either 1 μmol or 10 μmol scales and possessed a 3'-phosphate group. Compounds were synthesized directly on CPG beads or on polystyrene solid support. The compounds were synthesized in the 3' to 5' direction by standard solid phase DNA methods. Coupling methods employed standard β-cyanoethyl phosphoramidite chemistry conditions. All phosphoramidite monomers were dissolved in acetonitrile/dichloromethane (0.1 M solutions), and were added in successive order using the following synthesis cycles: 1) removal of the 5'-dimethoxytrityl protecting group with dichloroacetic acid in toluene, 2) coupling of the next phosphoramidite with activator reagent in acetonitrile, 3) oxidation with iodine/pyridine/water, and 4) capping with acetic anhydride/1-methylimidizole/acetonitrile. Extendable alkyne (compound 9 or Glen Research 10-1992) phosphoramidite (100 mg) was dissolved in dry acetonitrile (700 uL) and dichloromethane (300 uL). A few sieves were added to the flask and it was blanketed with argon. The sequencer was utilized as described above. The synthesis cycle was repeated until the 5' Oligofloroside was assembled. At the end of the chain assembly, the monomethoxytrityl (MMT) group or dimthoxytrityl (DMT) group was removed with dichloroacetic acid in dichloromethane or dichloroacetic acid in toluene. The compounds were cleaved from the solid support using concentrated aqueous ammonium hydroxide at room temperature for 2-4 hours. The product was concentrated in vacuo and Sephadex G-25 columns were used to isolate the main product. Analysis was done with a RP-HPLC method couple to a mass spectrometer for molecular weight determination.

Example 1

Synthesis of Exemplary Compounds of Structure (I)

Compounds with ethylene oxide linkers were prepared as followed:

The oligofluoroside constructs (i.e., compounds of structure (I)) were synthesized on an Applied Biosystems 394 DNA/RNA synthesizer on 1 μmol scale and possessed a 3'-phosphate group or 3'-$S_2$—$(CH_2)_6$—OH group or any of the other groups described herein. Synthesis was performed directly on CPG beads or on Polystyrene solid support using standard phopshoporamadite chemistry. The oligofluorosides were synthesized in the 3' to 5' direction using standard solid phase DNA methods, and coupling employed standard O-cyanoethyl phosphoramidite chemistry. Fluoroside phosphoramidite and spacers (e.g., hexaethyloxy-glycol phosphoramidite, triethyloxy-glycol phosphoramidite, polyethylene glycol phosphoramidite) and linker (e.g., 5'-amino-Modifier Phosphoramidite and thiol-Modifiers S2 Phosphoramidite) were dissolved in acetonitrile to make 0.1 M solutions, and were added in successive order using the following synthesis cycle: 1) removal of the 5'-dimethoxytrityl protecting group with dichloroacetic acid in dichloromethane, 2) coupling of the next phosphoramidite with activator reagent in acetonitrile, 3) oxidation of P(III) to form stable P(v) with iodine/pyridine/water, and 4) capping of any unreacted 5'-hydroxyl groups with acetic anhydride/1-methylimidizole/acetonitrile. The synthesis cycle was repeated until the full length oligofluoroside construct was assembled. At the end of the chain assembly, the monomethoxytrityl (MMT) group or dimethoxytrityl (DMT) group was removed with dichloroacetic acid in dichloromethane.

The compounds were provided on controlled-pore glass (CPG) support at 0.2 umol scale in a labeled Eppendorf tube. 400 μL of 20-30% $NH_4OH$ was added and mixed gently. Open tubes were placed at 55° C. for ~5 minutes or until excess gases had been liberated, and then were closed tightly and incubated for 2 hrs (+/−15 min.). Tubes were removed from the heat block and allowed to reach room temperature, followed by centrifugation at 13,400 RPM for 30 seconds to consolidate the supernatant and solids. Supernatant was carefully removed and placed into a labeled tube, and then 150 μL acetonitrile was added to wash the support. After the wash was added to the tubes they were placed into a CentriVap apparatus at 40° C. until dried.

The products were characterized by ESI-MS (see Table 2), UV-absorbance, and fluorescence spectroscopy.

Example 2

Preparation and Testing of Compositions Comprising a Polymeric Dye Compound and a Cyclodextrin Compounds I-12, I-13, I-14 and I-15 were prepared according to Example 1 and compositions were prepared and analyzed as follows.

Dry oligos were re-constituted in 0.1M $Na_2CO_3$ and final stock concentrations were measured by NanoDrop spectrometer. 2 μM solutions of each sequence were made from these stocks by diluting in 0.1M $Na_2CO_3$. Spectral analyses were performed in a 1 cm×1 cm quartz cuvette on a Cary UV spectrometer to show absorbance response relative to the group. Each of the 2 μM stocks were diluted by 200-fold in 0.1M $Na_2CO_3$ buffer down to 10 nM for the untreated controls. A 20 mM stock of HPbCD (hydroxypropyl-β-cyclodextrin) was made by dissolving 1116.8 mg in 40 mL of 0.1M $Na_2CO_3$ buffer, pH9. Each of the 2 μM stocks were diluted by 200-fold in this buffer down to 10 nM. The treated and untreated 10 nM stocks were analyzed in a 1 cm×1 cm quartz cuvette on a Cary/Agilent Eclipse Fluorimeter, using an excitation of 494 nm and emission scans from 499-700 nm. The instrument was zeroed between readings using the relevant buffer.

Figure 2:
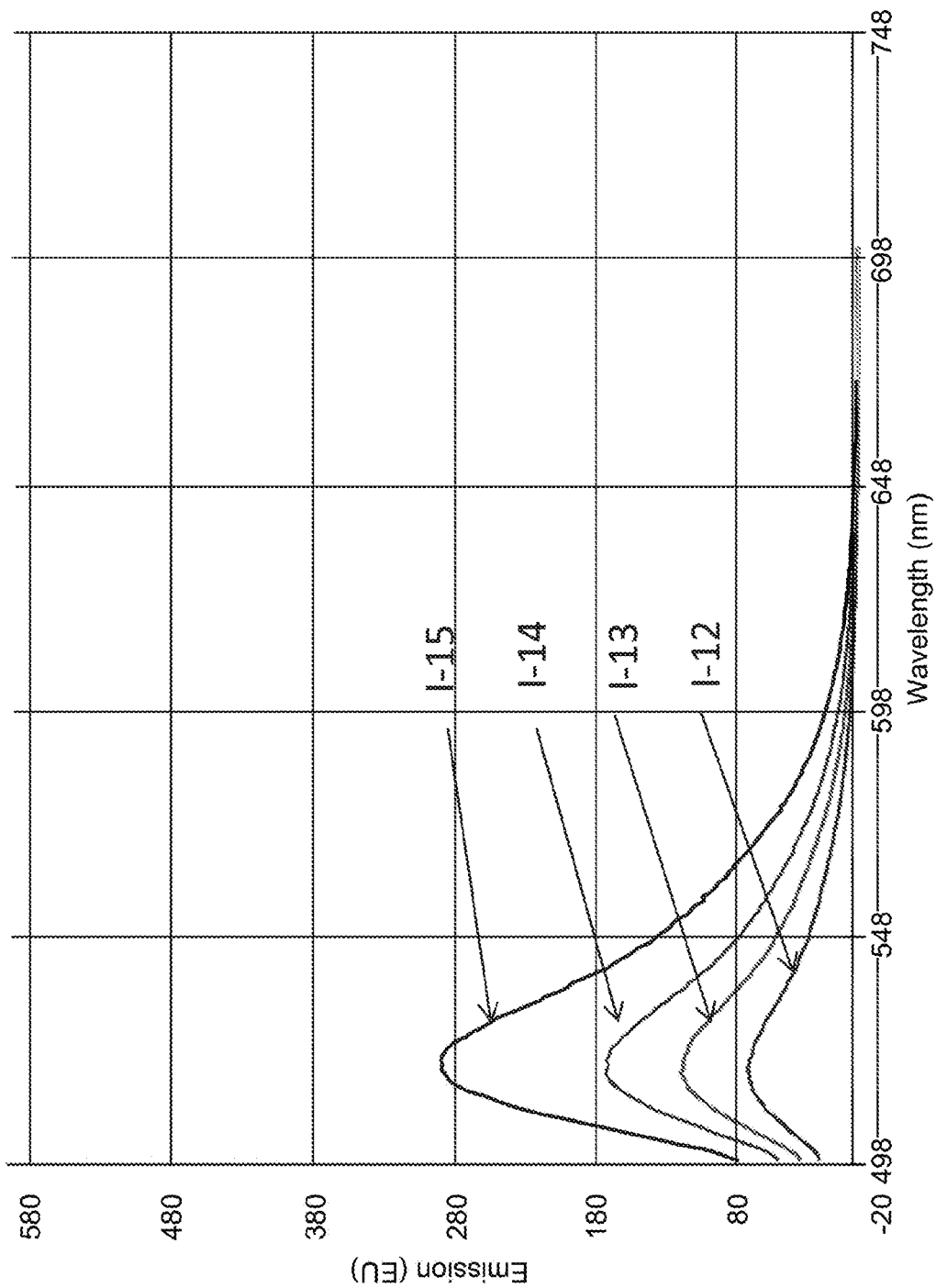
FIG. 2 provides fluorescence emission spectra for polymeric dyes in the absence of a cyclodextrin.
Figure 3:
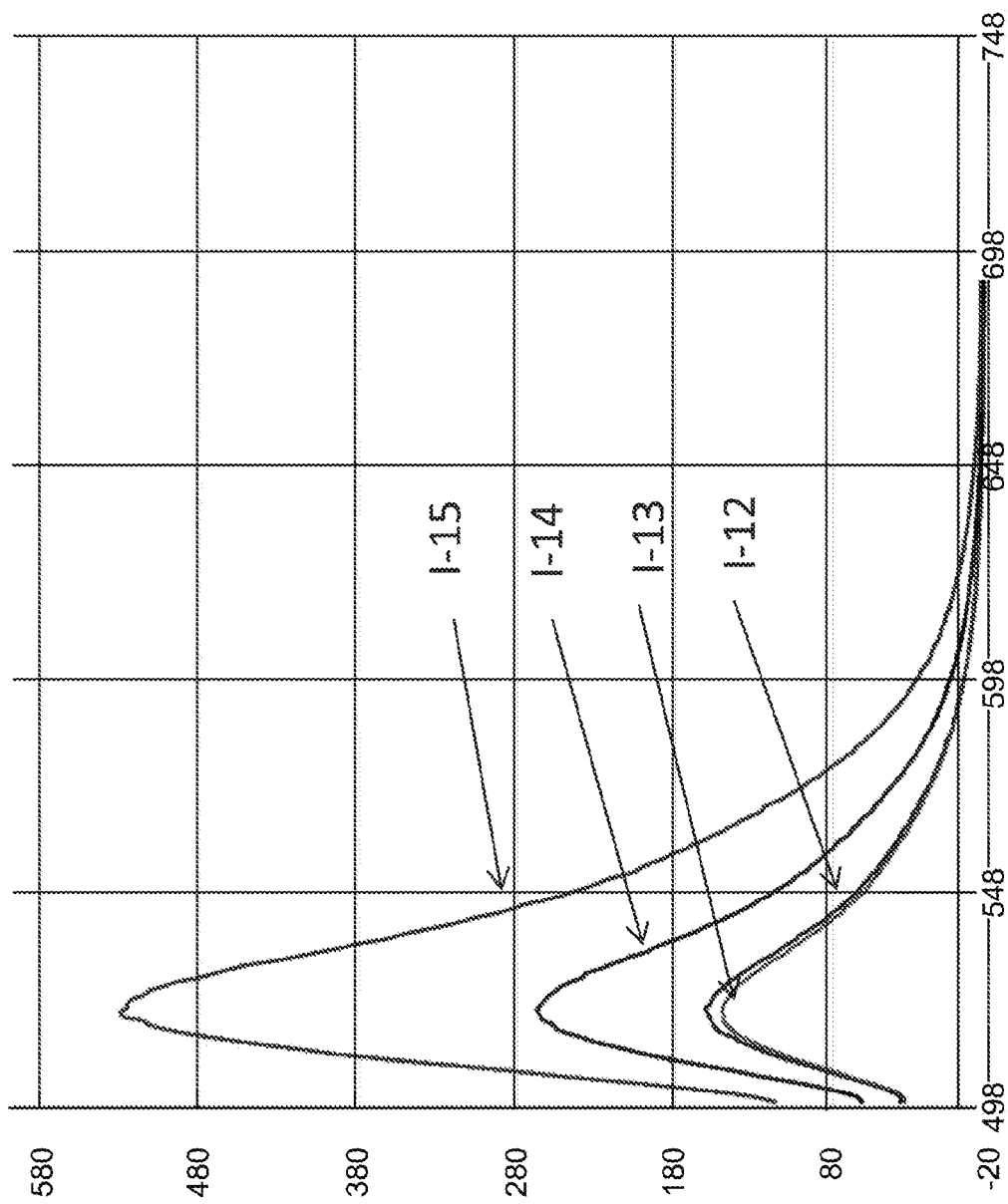
FIG. 3 is fluorescence emission data for polymeric dyes in the presence of a cyclodextrin.

FIG. 1 shows that the UV absorbance of the tested dyes increases with the increasing number of dye moieties. FIG. 2 shoes an increase of fluorescence with an increasing number of fluorescein moieties, but not to the extent of the increase in absorbance. This is believed to be related to intramolecular quenching of the fluorescent moieties. In contrast, the when the same dyes are tested in a solution comprising 20 mM HPbCD, emission intensities for all sequences were increased, and the increase was substantially correlated with the number of fluorescent moieties. While not wishing to be bound by theory, the HPbCD thus appears to be reducing or preventing intramolecular quenching.

Figure 4:
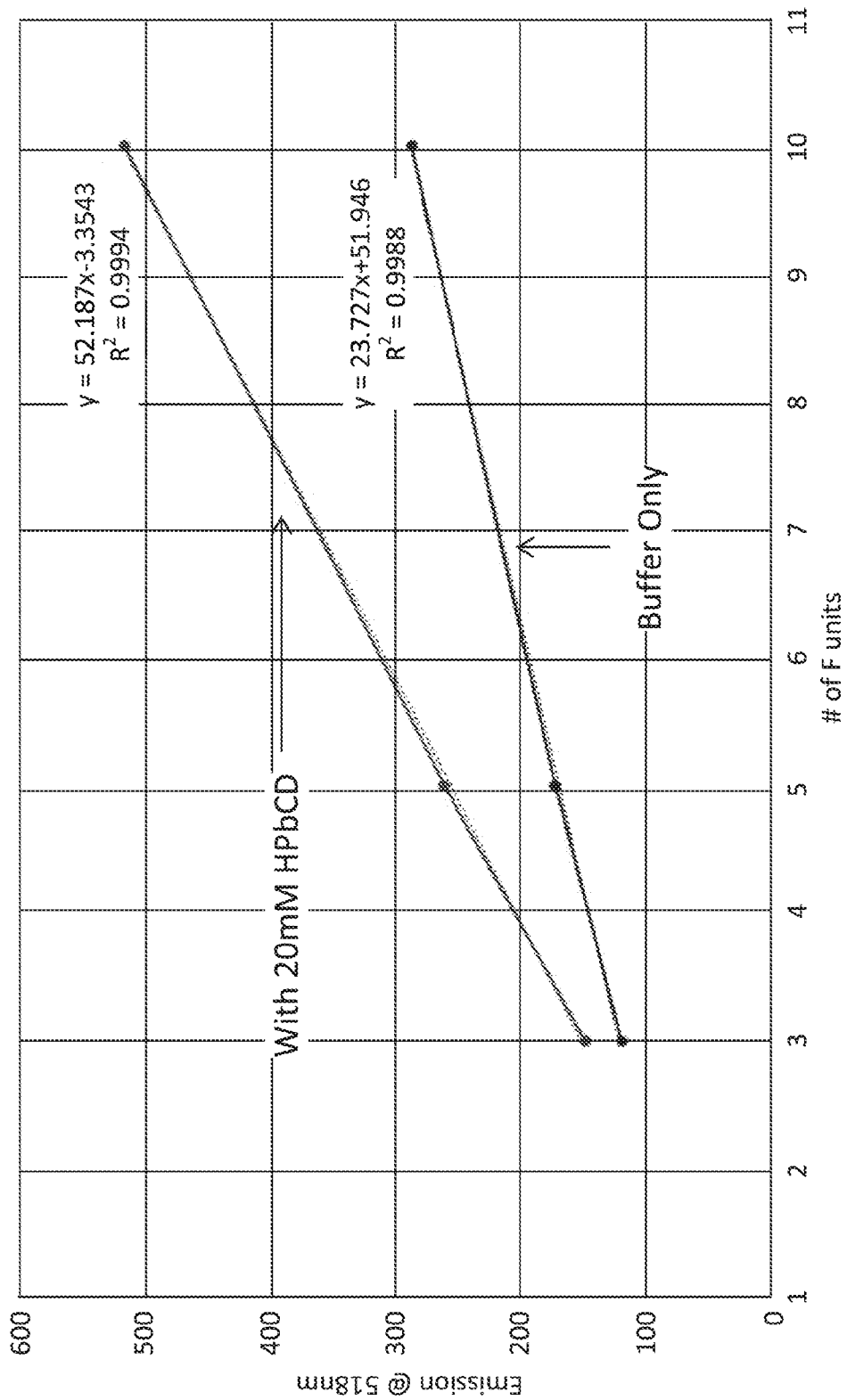
FIG. 4 shows the relationship between fluorescent emission and the number of fluorescent moieties in the presence and absence of a cyclodextrin.

FIG. 4 provides data showing that fluorescent emission is substantially linear with respect to the number of fluorescent moieties when HPbCD is present in the composition; however, in the absence of HPbCD, emission does not correlate linearly with the number of fluorescent moieties, presumably due to intramolecular quenching.

Example 3

Preparation of a Fluorescein (FAM) Azide Compound

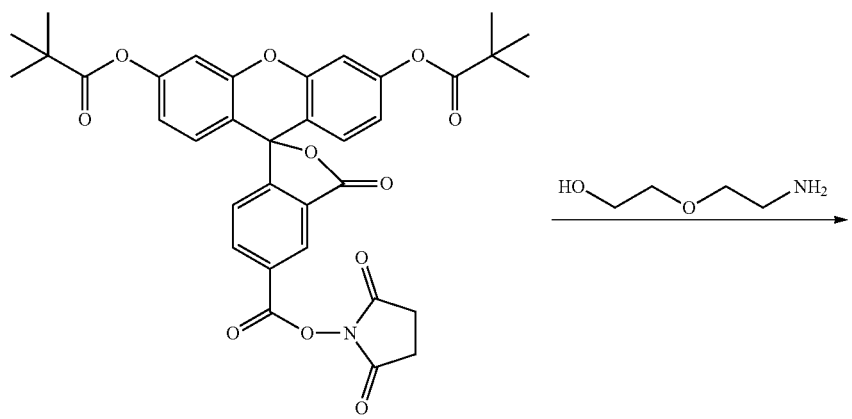

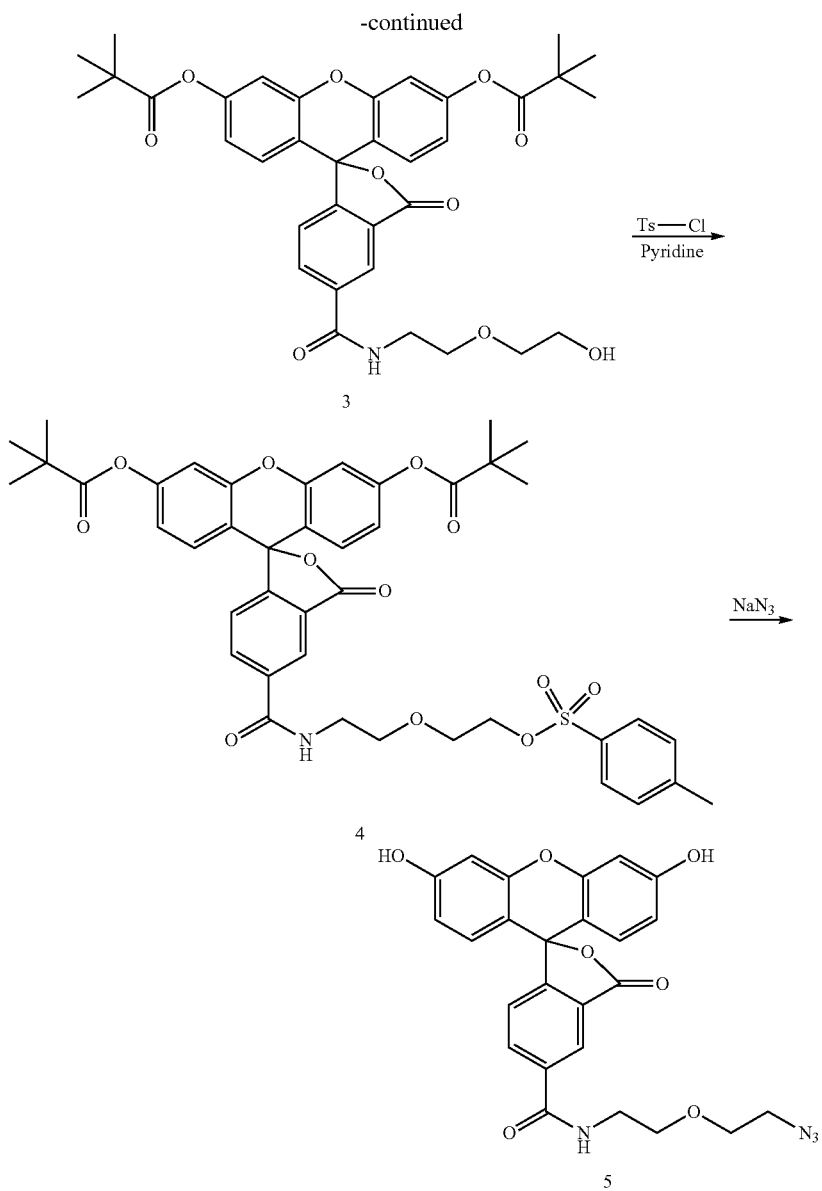

In a 250 ml round bottomed flask with magnetic stir bar and addition funnel was placed FAM-NHS ester 2 (2.24 g). Dichloromethane (35 mL) was added to the flask, stirring was initiated, flask placed under nitrogen and cooled on ice. In a separate beaker, 2-(2-aminoethoxy)ethanol (420 μL) was dissolved in dichloromethane (35 mL), methanol (7 mL) and triethylamine (1.5 mL) and the resulting solution was charged to the addition funnel. The amine solution was added dropwise to the NHS ester over 30 minutes. The final solution was stirred for 1 h at 0 C, the flask was removed from the ice bath and stirred at room temperature for 2 h. The reaction mixture was concentrated and the crude product was purified by silica gel chromatography. Product fractions were examined by TLC and LC/MS and pooled to afford 1.6 g (72%).

In a 250 mL round bottomed flask with magnetic stir bar was placed the FAM alcohol 3 (1.5 g) and chloroform (25 mL). To this solution was added pyridine (470 μL) and p-toluenesulfonyl chloride (691 mg). The mixture was stirred for 24 h at which point TLC indicated the reaction was incomplete, additional p-toluenesulfonyl chloride (1.4 g) and pyridine (1.5 mL) was added and the mixture stirred for an additional 24 h. TLC of the reaction after 48 h indicated the reaction was complete. The mixture was poured onto saturated sodium bicarbonate (200 mL) and dichloromethane (100 mL) in an extraction funnel and partitioned. The organic layer was retained and aqueous layer was extracted with dichloromethane (100 mL) two additional times. The organic layers were pooled and dried with sodium sulfate, filtered and concentrated. The crude product was purified by silica gel chromatography. Product fractions were identified by TLC and pooled to afford the desired tosylate 4 (1.8 g).

In a 200 mL round bottomed flask with magnetic stirrer was placed FAM-tosylate 4 (1.8 g) and DMF (15 mL) was added and the mixture was stirred to effect dissolution. To this was added sodium azide (830 mg) and the mixture heated to 50 C and stirred overnight. The mixture was poured onto 100 mM citric acid (150 mL) and ethyl acetate (150 mL) in an extraction funnel. The layers were partitioned and the organic layer retained. The aqueous layer was extracted with ethyl acetate two additional times. The organic layers were combined and dried over sodium sulfate. The solution was filtered and concentrated by rotary evaporation. The crude oil was purified by silica gel chromatography, product fractions were identified by TLC and pooled. The product was concentrated under vacuum to afford the desired FAM-aizde 5 as an orange solid (0.82 g). LCMS was consistent with the desired product.

Example 4

Synthesis of Alkyne Phosphoramidite

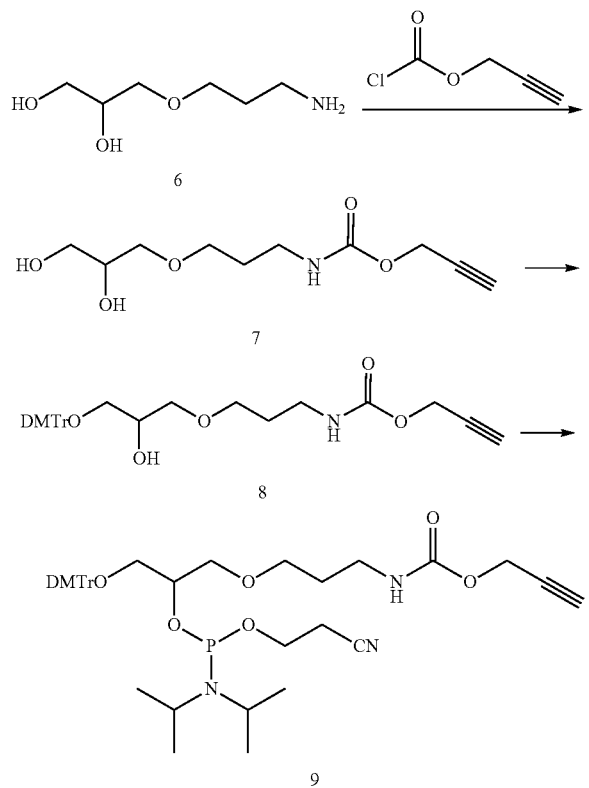

In a 500 mL round bottomed flask equipped with an addition funnel and magnetic stirrer was placed propargyl chloroformate (1.3 mL) in dichloromethane (75 mL). The flask was purged with nitrogen. In a separate beaker was placed aminoalcohol 6 (2.0 g) in dichloromethane (60 mL), methanol (10 mL) and triethylamine (1.4 mL). The addition funnel was charged with the aminoalcohol solution and was added dropwise over 30 minutes. The flask was stirred for 2 h at which point TLC indicated the reaction was complete. The reaction was concentrated on the rotary evaporator and further dried under high vacuum and used directly in the next step.

In a 500 mL round bottomed flask with magnetic stirrer was placed carbamate 7 (~3. g). Pyridine was added to the flask (270 mL) and stirring was initiated. Once the carbamate had been dissolved, the solution was placed on ice and stirred for 15 min under nitrogen. Dimethoxytrityl chloride (5.9 g) was added to the flask by powder funnel in a single portion. The flask was repurged with nitrogen and stirred at 0 C for 1 h. The flask was removed from ice and stirred at room temperature overnight. Methanol was added (10 mL) and the mixture stirred for 10 min. The mixture was concentrated on the rotovap and purified by silica gel chromatography. Product fraction were determined by TLC, pooled and concentrated to a final oil to afford mono-protected diol 8 (3.3 g).

In a 100 mL round bottomed flask with magnetic stir bar was placed monoprotected diol 8 (500 mg) and dichloromethane (5 mL). The mixture was stirred to the starting material was dissolved. Diisopropylethylamine (600 mg) and 2-cyanoethyl-N,N-diisopropylchlorophosphoramidite (440 mg) were added dropwise, simultaneously in separate syringes. The mixture was stirred for 1 h at which point TLC indicated the reaction was complete. The material was poured onto sodium bicarbonate solution, extracted with dichloromethane. The organic layer was dried with sodium sulfate, filtered and concentrated to an oil Additional purification was accomplished by silica gel chromatography, Dichloromethane with 5% triethylamine. Product fractions were identified by TLC, pooled and concentrated. The final product was isolated as a clear oil (670 mg).

Example 5

Synthesis of Exemplary Compounds of Structure (II)

3-, 5- and 10-mer polyalkyne oligomers were prepared from the phosphoramidite of Example 4 and using the general procedures described in Example 1, wherein a two carbon spacer phosphoramidite is used in place of the glycol spacer of Example 1. A representative 3-mer dye was prepared as follows:

In a 500 uL microcentrifuge tube was placed a solution of phosphate buffer (31.5 µL, 150 mM, pH=7.4). To this was added a solution of coumarin azide (22.5 µL, 10 mM in DMSO) and a solution of the polyalkyne (7.5 µL, 1 mM in water). In a separate 200 uL microcentrifuge tube was placed a solution of copper sulfate (3.0 µL, 50 mM), a solution of tris(3-hydroxypropyltriazolylmethyl)amine (THPTA, 3.0 µL, 100 mM) and a solution of sodium ascorbate (7.5 µL, 100 mM). The copper solution was mixed and the entire contents added to the coumarin azide/polyalkyne tube. The reaction was mixed and allowed to incubate overnight at room temperature. The mixture was diluted with water (75 µL) and purified by size exclusion chromatography (Superdex 200 increase 5/150 GL, isocratic elution with PBS, 0.25 mL/min, detection at 405 nM and 260 nM).

Compositions of compounds of structure (II) and a cyclodextrin are prepared and tested as described in Example 2.

Example 6

Synthesis of Exemplary Compounds of Structure (III)

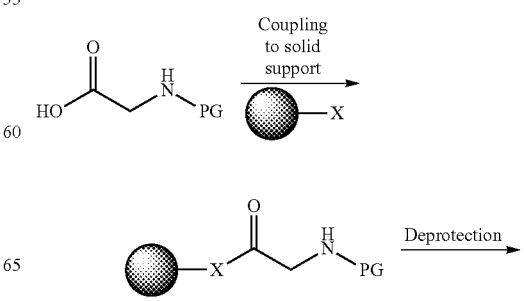

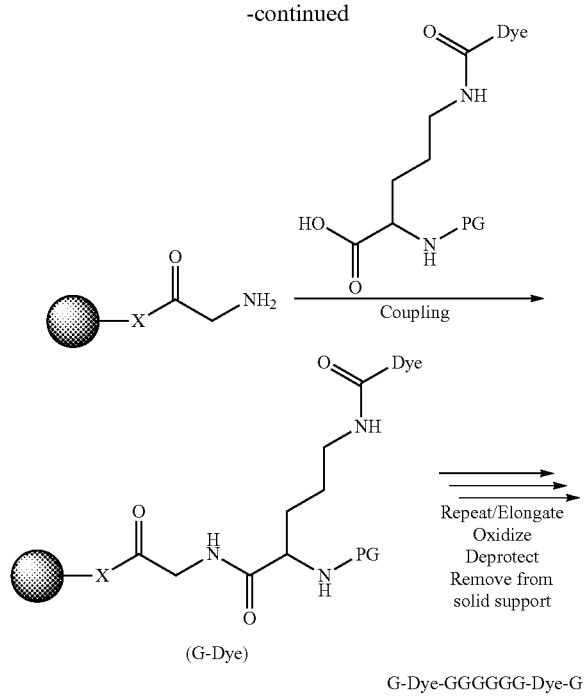

G-Dye-GGGGGG-Dye-G

The reaction scheme above illustrates an exemplary method for preparing an intermediate useful for preparation of compounds of structure (III), where PG is a suitable protecting group, X is a functional unit that a peptide chain can be built on, the shaded circle is a suitable solid support, and Dye is F', E', or Y'.

Small porous beads are initially treated with functional units, which bind to the surface of the porous beads. Peptide chains are built upon the functional units sites and remain covalently bonded to the bead until they are cleaved. When attached, a peptide chain is immobilized on the solid phase and retained during a filtration process, wherein liquid reagents and by-products of the synthesis are washed away.

The general cycle of solid phase synthesis is one of repeated cycles of deprotection-wash-coupling-wash. A free N-terminal amine of a peptide, attached to a solid support, is coupled to an N-protected amino acid group (e.g., with Fmoc or Boc). The newly introduced amino acid unit is deprotected to reveal a new N-terminal amine, which is further reacted with additional amino acids. The process is repeated and the peptide chain is elongated.

When the peptide chain has incorporated all desired amino acid and monomer units, it is cleaved from the bead. Cleaving reagents such as anhydrous hydrogen fluoride or trifluoroacetic acid can be used to cleave peptide chains from beads. The peptide chain is then collected, purified and characterized.

Compositions of compounds of structure (II) and a cyclodextrin are prepared and tested as described in Example 2.

Example 7

Synthesis of Phosphoramidite Dye Monomers

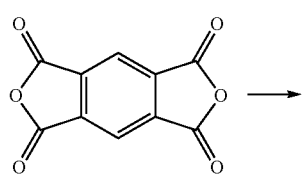

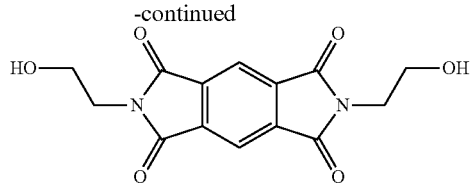

In a 250 mL round bottomed flask with stirring bar was placed pyromellitic anhydride (1.0 g, 4.59 mmol) and dioxane (50 mL). To this was added ethanolamine (622 µL, 11.5 mmol) and diisopropylethylamine (4.0 mL, 23 mmol). The flask was equipped with a reflux condenser, placed in an oil bath and heated to reflux overnight. The mixture was allowed to cool. The solids were filtered and retained for later. The filtrate was condensed and partitioned between ethyl acetate and water. The ethyl acetate layer was retained and the aqueous layer was extracted two additional times with ethyl acetate. The organic layers were combined, dried over sodium sulfate, filtered and concentrated to a solid. The solids from extraction and the earlier filtration were found to be identical by TLC and combined to afford the final material. (870 mg)

LC/MS of product showed m/z 305 associated with the largest peak. Overall purity was ~79%.

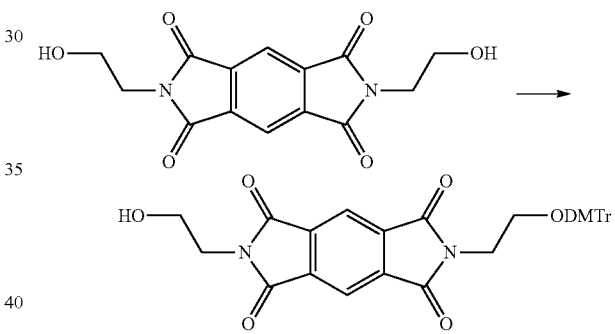

In a 100 mL round bottomed flask with stirring bar was placed the diol (850 mg, 2.8 mmol) in pyridine (15 mL). The mixture was cooled on ice under a stream of nitrogen. To this was added 4,4 dimethoxytrityl chloride (237 mg, 0.7 mmol). The mixture was stirred at 4° C. overnight. Methanol (2 mL) was added, and the mixture stirred for 15 min before concentrating to a paste on the rotovap. The residue was partitioned between a saturated solution of sodium bicarbonate and toluene. Retained toluene layer and extracted aqueous layer two additional times with dichloromethane. The organic layers were combined, dried with sodium sulfate and concentrated. Final purification was accomplished with silica gel chromatography (dichloromethane/methanol gradient) to afford the final product as a solid (372 mg).

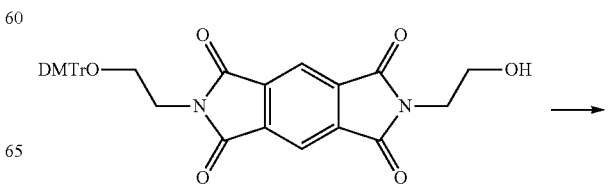

115

-continued

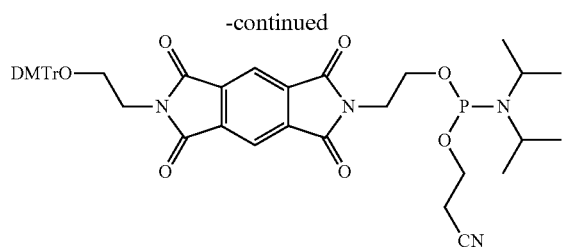

In a 100 mL round bottomed flask with stirring bar was placed the monoprotected DMTr alcohol (150 mg, 0.24 mmol) in dry dichloromethane (25 mL) with diisopropylethylamine (215 µL, 1.23 mmol). 2-cyanoethyl-N,N-diisopropylchlorophosphoramidite (110 µL, 0.49 mmol) was added and the mixture stirred for 30 min at which point TLC indicated the reaction was complete. The mixture was partitioned between dichloromethane and saturated sodium bicarbonate. The organic layer was retained, dried over sodium sulfate and concentrated to a yellow oil which was used directly on the DNA synthesizer.

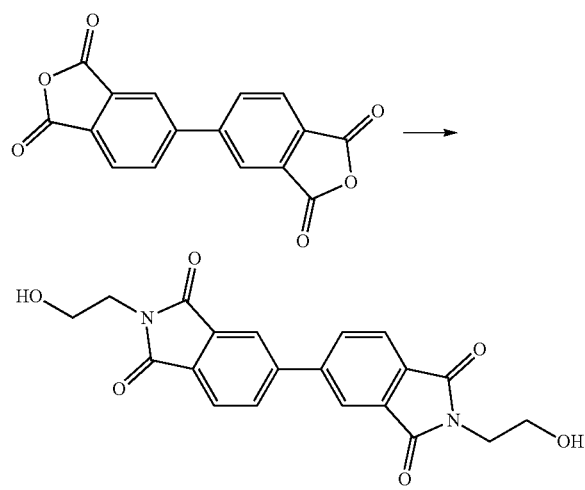

116

In a 250 mL round bottomed flask with stirring bar was placed 3,3',4,4'-biphenyltetracarboxylic dianhydride (1.2 g, 4. mmol) and dioxane (80 mL). Ethanolamine (616 µL, 10.2 mmol) and diisopropylethylamine (3.5 mL) were added, the flask was equipped with a reflux condenser and the mixture heated to reflux overnight. The reaction was cooled and added to a stirring beaker of water (1500 mL) to effect precipitation. The solids were collected by filtration and dried under vacuum (0.74 g)

Purity was >95%. Predicted MW is 380.4. MW found was 380.2.

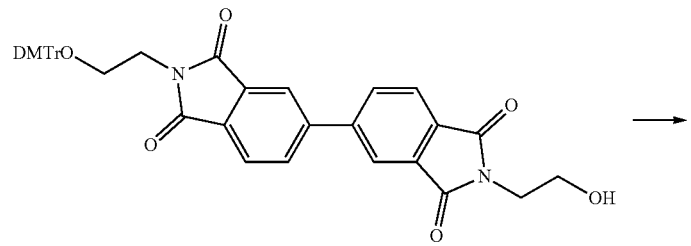

In a 50 mL round bottomed flask with stir bar was placed the diol (700 mg, 1.8 mmol) in pyridine (9 mL). The mixture was cooled on ice under nitrogen. To this was added 4,4 dimethoxytrityl chloride (468 mg, 1.4 mmol). The mixture was stirred at 4° C. overnight. Methanol (2 mL) was added, and the mixture stirred for 10 min before concentrating to a paste on the rotovap. Final purification was accomplished with silica gel chromatography (dichloromethane/methanol gradient) to afford the final product as a solid (151 mg).

Overall purity is ~89%. M/Z 773.8 is consistent with product+tropylium.

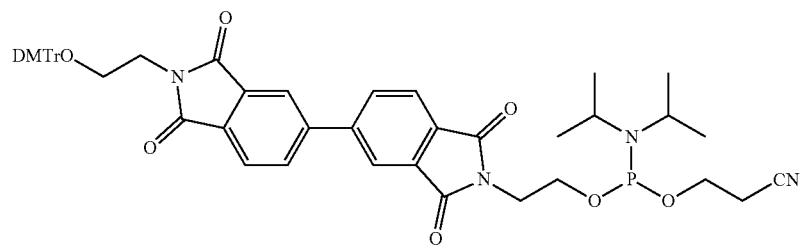

In a 100 mL round bottomed flask with stirring bar was placed the monoprotected DMTr alcohol (132 mg, 0.19 mmol) in dry dichloromethane (25 mL) with diisopropylethylamine (168 µL, 0.74 mmol). 2-cyanoethyl-N,N-diisopropylchlorophosphoramidite (86 µL, 0.38 mmol) was added and the mixture stirred for 30 min at which point TLC indicated the reaction was complete. The mixture was partitioned between dichloromethane and saturated sodium bicarbonate. The organic layer was retained, dried over sodium sulfate and concentrated to an oil which was used directly on the DNA synthesizer.

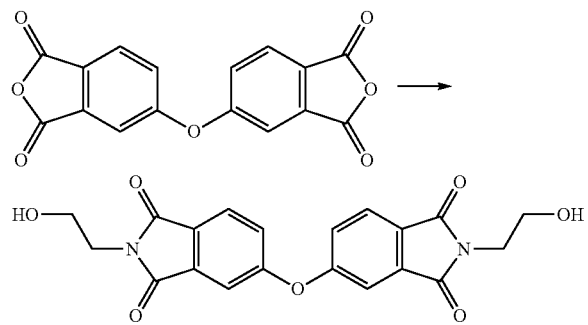

In a 250 mL round bottomed flask with stirring bar was placed 4,4'-Oxydiphthalic anhydride (1.2 g, 3.9 mmol) and dioxane (90 mL). Ethanolamine (584 µL, 9.7 mmol) and diisopropylethylamine (3.4 mL) were added, the flask was equipped with a reflux condenser and the mixture heated to reflux overnight. The reaction was cooled and concentrated on a rotovap to a paste which was partitioned between ethyl acetate and water. The organic layer was retained and the aqueous layer was extracted and additional time with ethyl acetate. The organic layers were combined, dried over sodium sulfate and concentrated to the final solid product (1.33 g)

Overall purity is ~83%. Main peak at 1.16 min. Calculated MW is 396.4. MW found is 396.2.

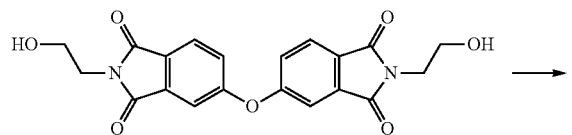

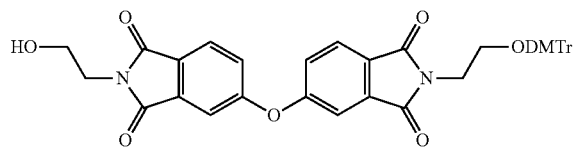

In a 20 mL round bottomed flask with stir bar was placed the diol (700 mg, 1.8 mmol) in pyridine (9 mL). The mixture was cooled on ice under nitrogen. To this was added 4,4 dimethoxytrityl chloride (449 mg, 1.3 mmol). The mixture was stirred at 4° C. overnight. Methanol (2 mL) was added, and the mixture stirred for 15 min before concentrating to a paste on the rotovap. Final purification was accomplished with silica gel chromatography (dichloromethane/methanol gradient) to afford the final product as a solid (600 mg).

Overall purity is ~82%. Predicted MW is 698.7. MW found is 788.5, which is consistent with product+tropylium.

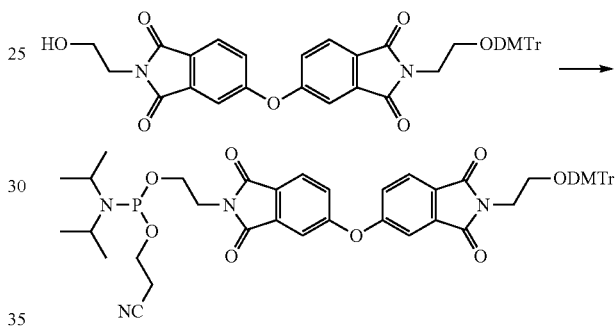

In a 100 mL round bottomed flask with stirring bar was placed the monoprotected DMTr alcohol (100 mg, 0.14 mmol) in dry dichloromethane (25 mL) with diisopropylethylamine (125 µL, 0.71 mmol). 2-cyanoethyl-N,N-diisopropylchlorophosphoramidite (64 µL, 0.28 mmol) was added and the mixture stirred for 30 min at which point TLC indicated the reaction was complete. The mixture was partitioned between dichloromethane and saturated sodium bicarbonate. The organic layer was retained, dried over sodium sulfate and concentrated to a yellow oil which was used directly in solid phase oligonucleotide synthesis.

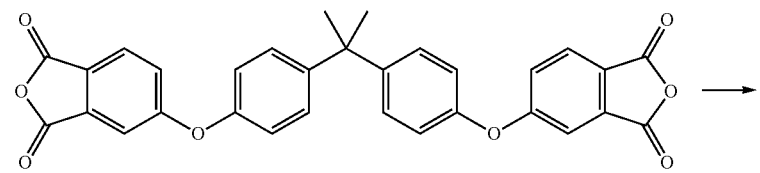

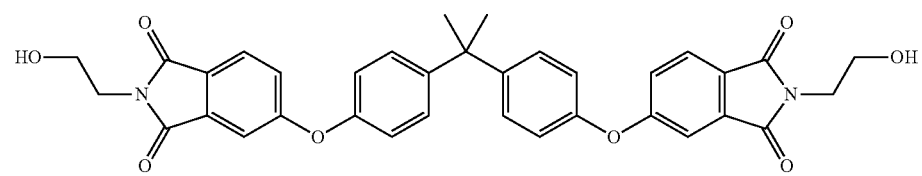

In a 250 mL round bottomed flask with stirring bar was placed 4,4'-(4,4'-Isopropylidinediphenoxy)bis(phthalic anhydride) (1.5 g, 2.9 mmol) and dioxane (50 mL). Ethanolamine (435 µL, 7.2 mmol) and diisopropylethylamine (2.5 mL) were added, the flask was equipped with a reflux condenser and the mixture heated to reflux overnight. The reaction was cooled and concentrated on a rotovap to a paste which was partitioned between dichloromethane and water. The organic layer was retained and the aqueous layer was extracted two additional times with dichloromethane. The organic layers were combined, dried over sodium sulfate and concentrated to the final solid product (400 mg).

Overall purity is ~89%. Predicted MW is 606.6. MW found is 606.4.

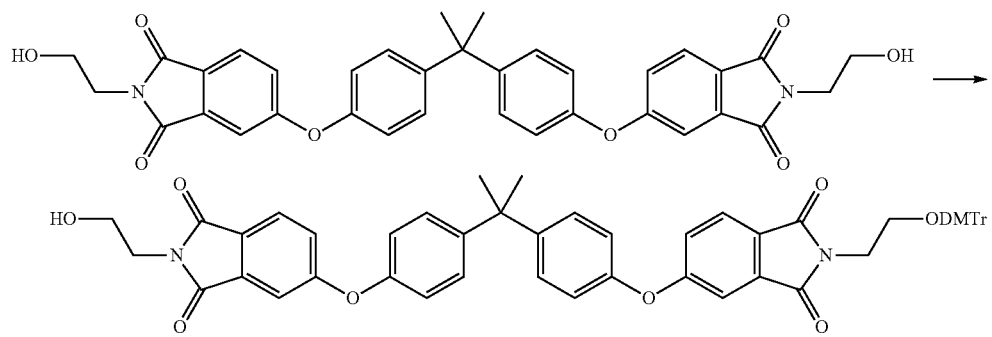

In a 20 mL round bottomed flask with stir bar was placed the diol (400 mg, 0.7 mmol) in pyridine (3 mL). The mixture was cooled on ice under nitrogen. To this was added 4,4 dimethoxytrityl chloride (168 mg, 0.5 mmol). The mixture was stirred at 4° C. overnight. Methanol (1 mL) was added, and the mixture stirred for 10 min before concentrating to a paste on the rotovap. Final purification was accomplished with silica gel chromatography (dichloromethane/methanol gradient) to afford the final product as a solid. Overall purity is ~36%. M/Z at 1000 is consistent with mass+tropylium)

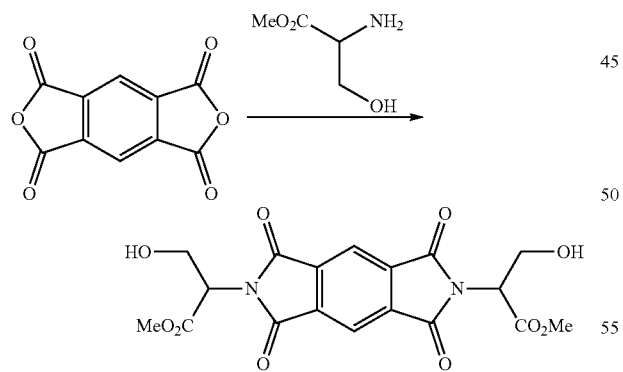

In a 250 mL round bottomed flask with stirring bar was placed pyromellitic dianhydride (0.75 g, 3.4 mmol) and dioxane (80 mL). Serine Methyl ester (1.2 g, 7.6 mmol) and diisopropylethylamine (4.8 mL) were added, the flask was equipped with a reflux condenser and the mixture heated to reflux overnight. The reaction was cooled and concentrated on a rotovap to a paste which was partitioned between ethyl acetate and citric acid (500 mM). The organic layer was retained and the aqueous layer was extracted and two additional times with ethyl acetate. The organic layers were combined, dried over sodium sulfate and concentrated to the final oil (1.4 g).

Calculated MW is 420.33. MW found is 420.1.

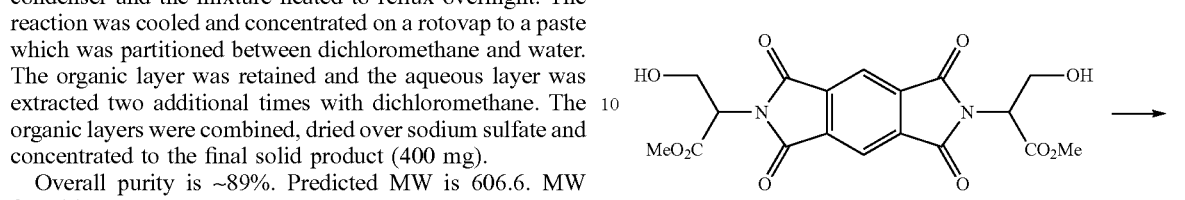

-continued

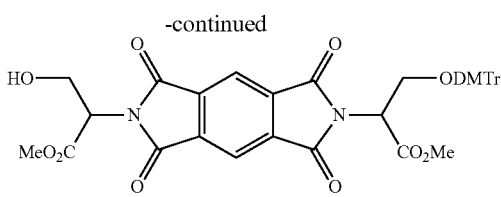

In a 100 mL round bottomed flask with stir bar was placed the diol (1.4 g, 3.5 mmol) in pyridine (17 mL). The mixture was cooled on ice under nitrogen. To this was added 4,4 dimethoxytrityl chloride (883 mg, 2.6 mmol). The mixture was stirred at 4° C. overnight. Methanol (5 mL) was added, and the mixture stirred for 10 min before concentrating to a paste on the rotovap. The residue was partitioned between a saturated solution of sodium bicarbonate and ethyl acetate. Retained organic layer and extracted aqueous layer two additional times with ethyl acetate. The organic layers were combined, dried with sodium sulfate and concentrated. Final purification was accomplished with silica gel chromatography (dichloromethane/ethyl acetate gradient) to afford the final product as an oil (1.7 g). MW at 812 consistent with mass plus tropyllium.

Example 8

Synthesis of Exemplary Compounds of Structure (IV)

Polymeric dyes of structure (IV) are prepared were prepared using the phosphoramidites of Example 7 and the procedures analogous to those described above. Exemplary compounds and their analytic characterization are provided in Table 5.

Compositions of compounds of structure (IV) and a cyclodextrin are prepared and tested as described in Example 2.

Example 9

General Flow Cytometry Method and Applications

The general flow cytometry workflow includes the following steps:
1. Culture and visually observe cells for signs of metabolic stress and/or use fresh, induced, or simulated cells.
2. Dilute dye compounds to working volumes.
3. Harvest and prepare cells without killing or inducing apoptosis.
4. Centrifuge and wash cells with appropriate buffer.
5. Perform cell counts using hemocytometer and trypan blue exclusion.
6. Centrifuge and wash cells
7. Adjust cell density to test size
8. Apply dye (pre-dilution) or other co-stains of interest.
9. Incubate the cell/stain/dye mixture.
10. Centrifuge and wash cells with appropriate buffer.
11. Re-suspend cells in acquisition buffer.
12. Acquire cell data by flow cytometry.

The general workflow described above can be modified accord to specific applications. Some modifications for specific applications are described below.

Live/Dead Discrimination

Cells are tested for viability by positively staining necrotic cells to compare damaged cells to intact cells. Assays are used to target non-intact (fixed and non-fixed) cells with positively charged moieties, cell debris, apoptotic bodies, depolarized cell membrane, and permeabilized membranes. Cells are then stained with dye using routine cell preparations (fresh or fixed) and analyzed using flow cytometry.

Cell Health

A comparison is made between dead cells (i.e., necrotic cells), early apoptotic, late apoptotic, and live cells. Dead cells are positively stained, Apoptotic bodies are intermediately stained, and live cells are left negative. This strategy results in very bright necrotic cells and works also to assess cell permeability. Assays are used to target non-intact (fixed and non-fixed) cells with positively charged moieties, cell debris, apoptotic bodies, depolarized cell membrane, and permeabilized membranes. Dye staining is performed on in vitro cultures, primary cells, and samples treated with xenobiotics and analyzed using flow cytometry.

Cell Cycle

Cell ploidy and mitosis is the cell cycle is tracked by staining correlated to positively staining DNA intercalators in all cells and cellular bodies containing nucleic acid and cell cycle associated proteins. Assays are used to target non-intact (non-fixed only) cells with positively charged moieties, cell debris, apoptotic bodies, depolarized cell membrane, and permeabilized membranes. Assays are used to target intact (fixed and permeabilized) cells by staining positively charged moieties after preservation of cells are fixed and permeabilized for intracellular staining. Dye staining (in combination with other dyes) is performed on in vitro cultures, primary cells, and samples treated with xenobiotics and analyzed using flow cytometry.

Proliferation

Cell proliferation is monitored by staining correlated to positively staining DNA intercalators in all cells and cellular bodies containing nucleic acid and cell cycle associated proteins. Assays are used to target non-intact (non-fixed only) cells with positively charged moieties, cell debris, apoptotic bodies, depolarized cell membrane, and permeabilized membranes. Assays are used to target intact (fixed and permeabilized) cells by staining positively charged moieties after preservation of cells are fixed and permeabilized for intracellular staining. Dye staining (in combination with monitoring markers for cell proliferation, e.g. Ki67, BRDU) is performed on in vitro cultures, primary cells, and samples treated with xenobiotics and analyzed using flow cytometry.

Example 10

Preparation of 99-Mer Dye

Compound I-42, having 33 fluorescein moieties was prepared using standard solid-phase oligonucleotide techniques as described herein. I-42 (represented by "A" in the below scheme) was trimerized as illustrated and described below to form a 99-mer dye.

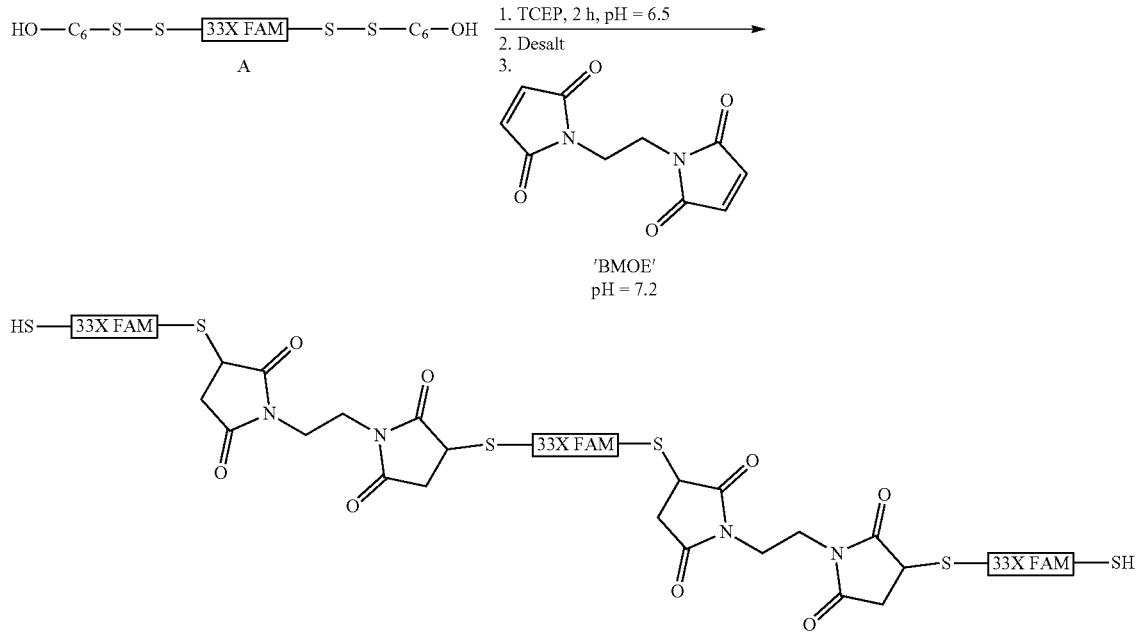

In a 200 μL polypropylene tube was placed sodium phosphate buffer (3.5 μL, 100 mM, pH=6.5) and a solution of 1-42 bis-disulfide (5.5 μL, 0.18 mM in water). To this was added a solution tris(2-carboxyethyl)phosphine (TCEP, 1.0 μL, 10 mM in water). The tube was capped, vortexed and allowed to incubate at room temperature for 2 h. The mixture was desalted through micro Zeba Spin desalting columns (Pierce, Cat #89877). The desalted solution was treated with sodium phosphate buffer (2.0 μL, 500 mM, pH=7.2) and a DMSO solution of bismaleimidoethane (BMOE, 1.0 μL, 0.25 mM) and incubated overnight at room temperature. The reaction mixture was diluted with water (100 μL) and analyzed by PAGE (FIG. 10, Invitrogen EC6875, 10% TBE-Urea gel, 180V constant, electrophoresis halted with resolution of highest MW species completed, visualized by UV illumination (365 nm)).

Other oligomer dyes having any desired number of dye moieties are prepared in an analogous manner.

Example 11

Preparation of Phosphoramidites and Compounds

Exemplary compounds were prepared using standard solid-phase oligonucleotide synthesis protocols and a fluorescein-containing phosphoramidite having the following structure:

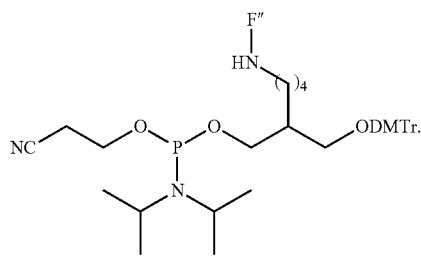

which was purchased from ChemGenes (Cat.#CLP-9780).

Exemplary linkers ($L^4$) were included in the compounds by coupling with a phosphoramidite having the following structure:

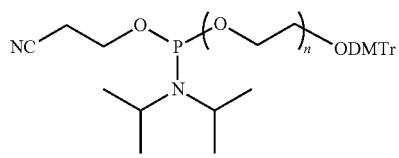

which is also commercially available.

Other exemplary compounds were prepared using a phosphoramidite prepared according to the following scheme:

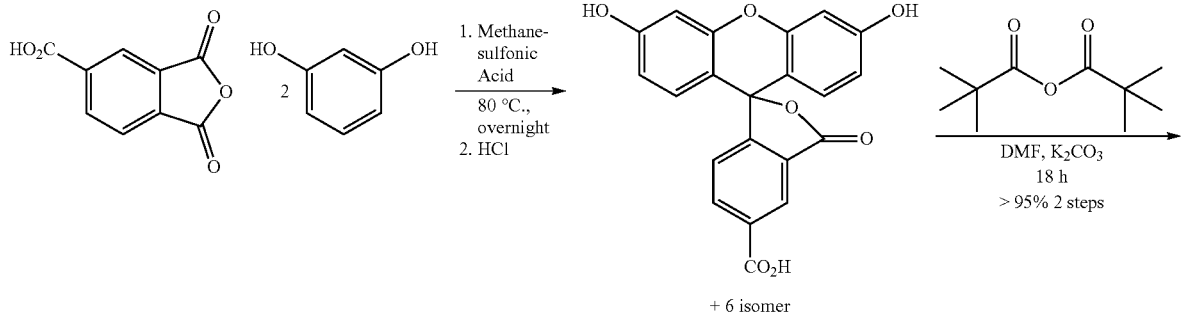

+ 6 isomer

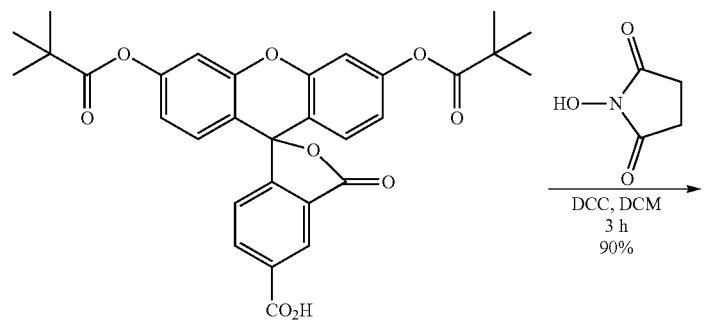

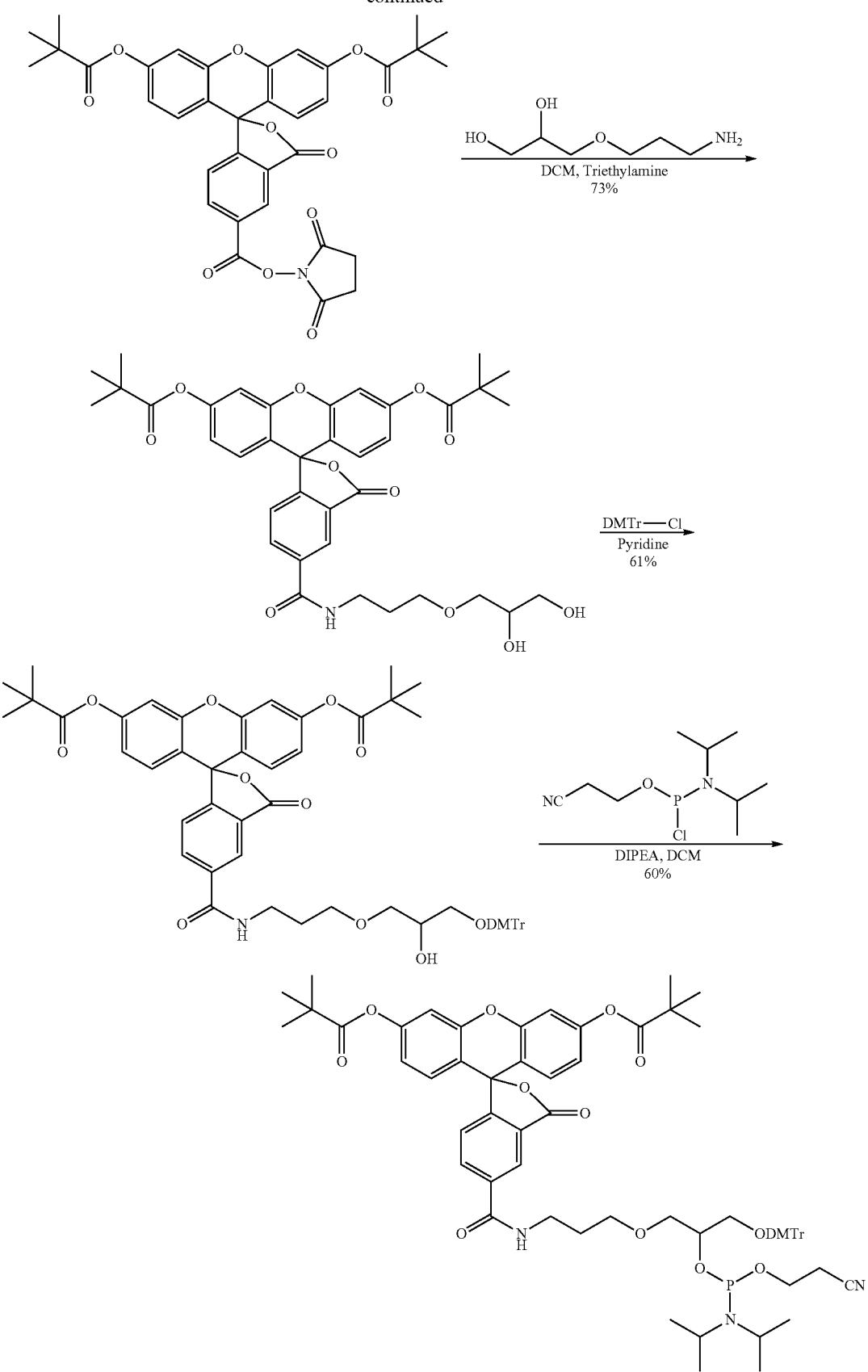
-continued

Final Deprotection produces the desired F''' moiety. Other commercially available phosphoramidite reagents were employed as appropriate to install the various portions of the compounds. Q moieties having the following structure:

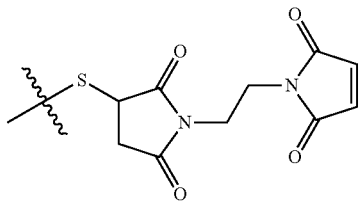 [SMILES: *SC1CC(=O)N(CCN2C(=O)C=CC2=O)C1=O]

were installed by reaction of:

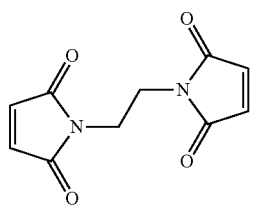 [SMILES: O=C1C=CC(=O)N1CCN1C(=O)C=CC1=O]

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

Should read:
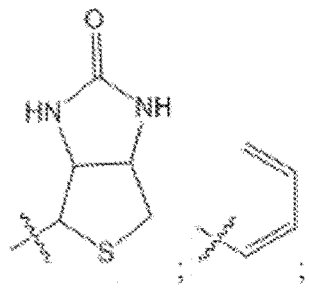

What is claimed is:

1. A composition comprising a polymeric dye and a cyclodextrin, wherein the polymeric dye is a compound having the following structure (I):

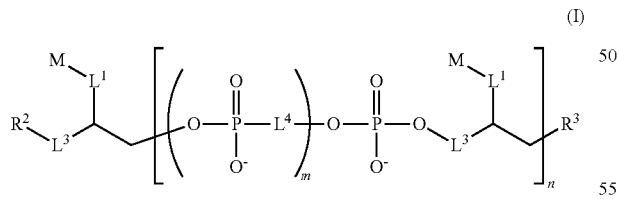

or a stereoisomer, salt or tautomer thereof, wherein:

M is, at each occurrence, independently a bivalent pyrene, 6-FAM, dimethylaminostilbene, quinacridone, fluorophenyl-dimethyl-BODIPY, bis-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9,10-ethynylanthracene, ter-naphthyl moiety, p-terphenyl, perylene, azobenzene, phenazine, phenanthroline, acridine, thioxanthrene, chrysene, rubrene, coronene, cyanine, perylene imide, perylene monoimide, perylene amide, coumarin dye, resorufin dye, dipyrrometheneboron difluoride dye, ruthenium bipyridyl dye, energy transfer dye, thiazole orange dye, polymethine, or N-aryl-1,8-naphthalimide dye;

$L^1$ is at each occurrence, independently an optional alkylene or heteroalkylene linker;

$L^3$ is, at each occurrence, independently an optional alkylene linker;

$L^4$ is, at each occurrence, independently an alkylene oxide linker of greater than three atoms in length;

$R^2$ and $R^3$ are each independently H, OH, SH, alkyl, alkoxy, alkylether, heteroalkyl, $-OP(=R_a)(R_b)R_c$, Q, or a protected form thereof, or L';

$R_a$ is O or S;

$R_b$ is OH, SH, O$^-$, S$^-$, OR$_d$ or SR$_d$;

$R_c$ is OH, SH, O$^-$, S$^-$, OR$_d$, OL', SR$_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising sulfhydryl, disulfide, N-succinimide ester, imidoester, polyfluorophenyl ester, isothiocyanate, azide, alkyne, alkene, diene, dienophile, acid halide, sulfonyl halide, phosphine, α-haloamide, biotin, amino or maleimide functional group;

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

m is, at each occurrence, independently an integer of zero or greater, provided that at least one occurrence of m is an integer of one or greater; and n is an integer of one or greater.

2. The composition of claim 1, wherein the cyclodextrin is α-cyclodextrin, β-cyclodextrin or γ-cyclodextrin.

3. The composition of claim 1, wherein the cyclodextrin is β-cyclodextrin.

4. The composition of claim 1, wherein each M is independently a fluorescent moiety.

5. The composition of claim 1, wherein the polymeric dye comprises from 2 to 10 M moieties.

6. The compound of claim 1, wherein M, at each occurrence, independently has one of the following structures:
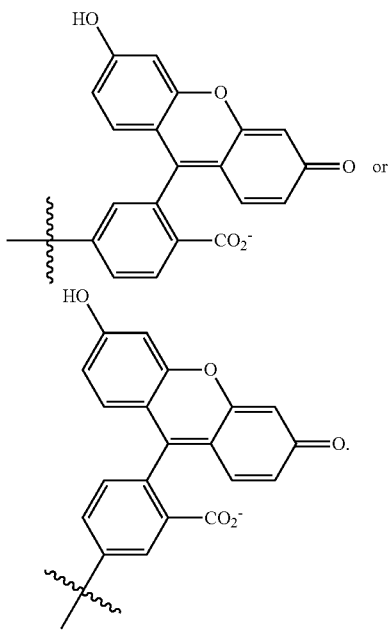
or
7. The composition of claim 1, wherein the polymeric dye compound has the following structure (IA):
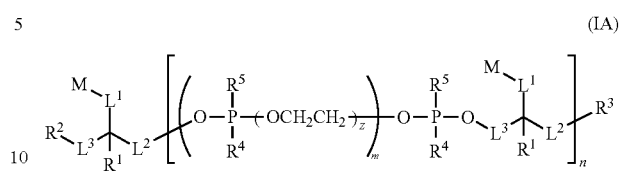
(IA)
wherein z is an integer from 2 to 100.
8. The composition of claim 7, wherein:
L¹ comprises one of the following structures:
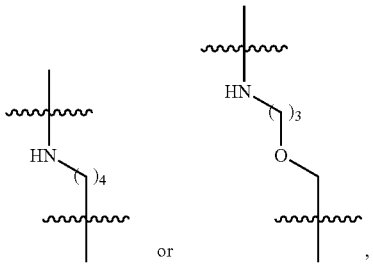
or ,
R² comprises one of the following structures:
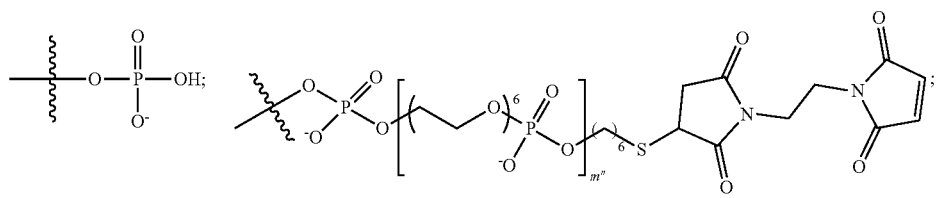
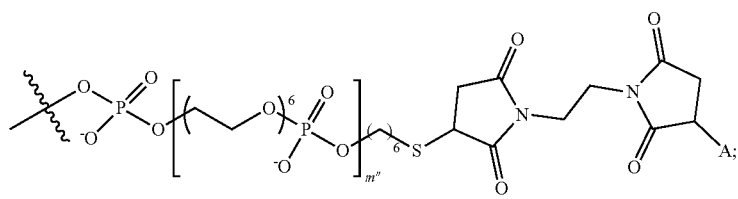
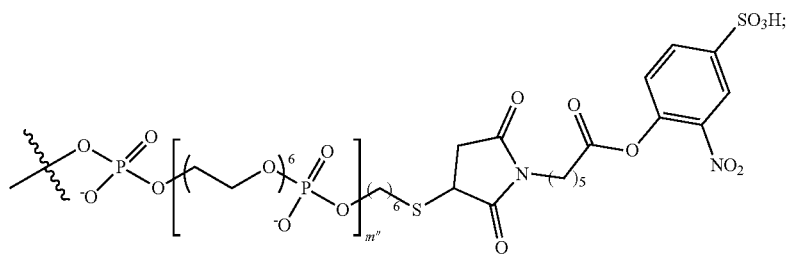
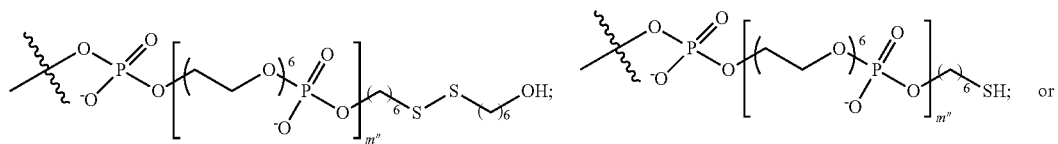

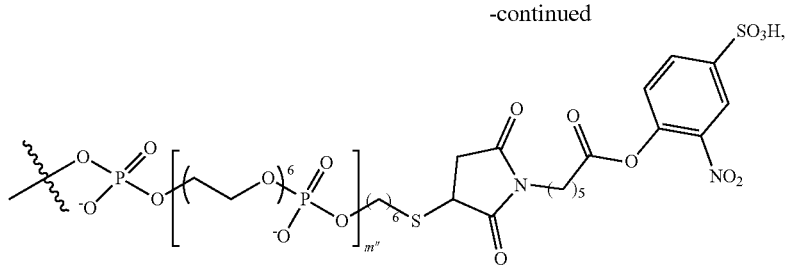

wherein:
A is an antibody; and
m" is 1, 4, or 10,
R³ comprises one of the following structures:

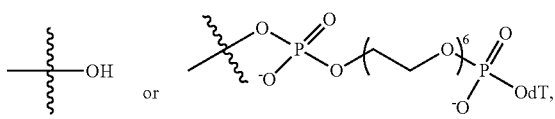

wherein dT has the following structure:

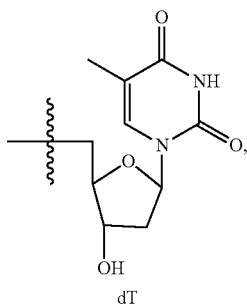 [SMILES: *CC1OC(n2cc(C)c(=O)[nH]c2=O)CC1O]

M comprises one of the following structures:

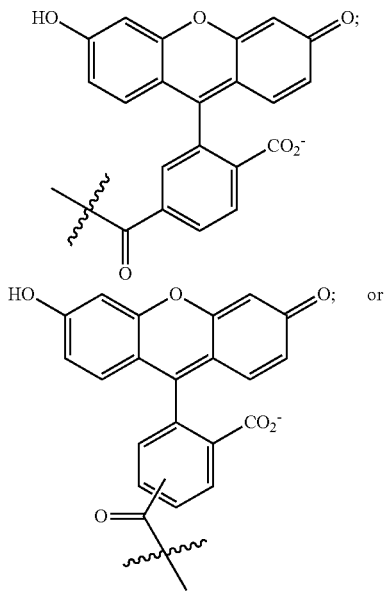

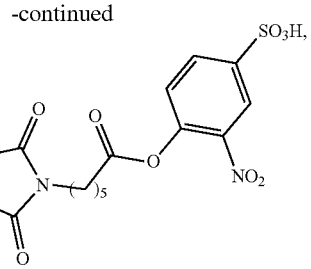

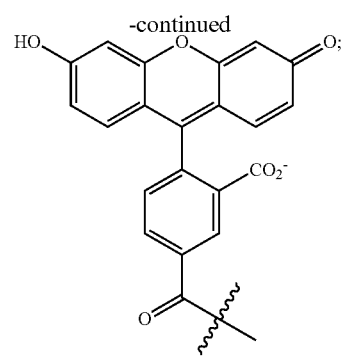

m is 2, 3, 4, or 5; and
n is 1-10.

9. A method of staining a sample, comprising adding to said sample the composition of claim 1 in an amount sufficient to produce an optical response when said sample is illuminated at an appropriate wavelength.

10. A method for visually detecting an analyte molecule, the method comprising:
(a) providing the composition of claim 1, wherein the polymeric dye comprises a covalent bond to the analyte molecule; and
(b) detecting the compound by its visible properties.

11. A method for visually detecting an analyte molecule, the method comprising:
(a) admixing the composition of claim 1, wherein the polymeric dye comprises a covalent bond to a moiety Q comprising a reactive group capable of forming a covalent bond with the analyte molecule, with the analyte molecule;
(b) forming a conjugate of the compound and the analyte molecule; and
(c) detecting the conjugate by its visible properties.

12. A method for determining the presence of dead cells in a sample, the method comprising contacting the sample with the composition of claim 1, thereby binding or associating the polymeric dye with the dead cells, and observing a fluorescent signal from the polymeric dye bound or associated with the dead cells.

13. The composition of claim 1, wherein $R^2$ and $R^3$ are each independently OH or —OP(=$R_a$)($R_b$)$R_c$.

14. The composition of claim 1, wherein one of $R^2$ or $R^3$ is OH or —OP(=$R_a$)($R_b$)$R_c$, and the other of $R^2$ or $R^3$ is Q or a linker comprising a covalent bond to Q.

15. The composition of claim 1, wherein one of $R^2$ or $R^3$ is OH or —OP(=$R_a$)($R_b$)$R_c$, and the other of $R^2$ or $R^3$ is a linker comprising a covalent bond to an analyte molecule, targeting moiety or a linker comprising a covalent bond to a solid support.

16. The composition of claim 1, wherein M is, at each occurrence, independently a moiety comprising four or more aryl or heteroaryl rings, or combinations thereof.
17. The composition of claim 1, wherein Q comprises one of the following structures:
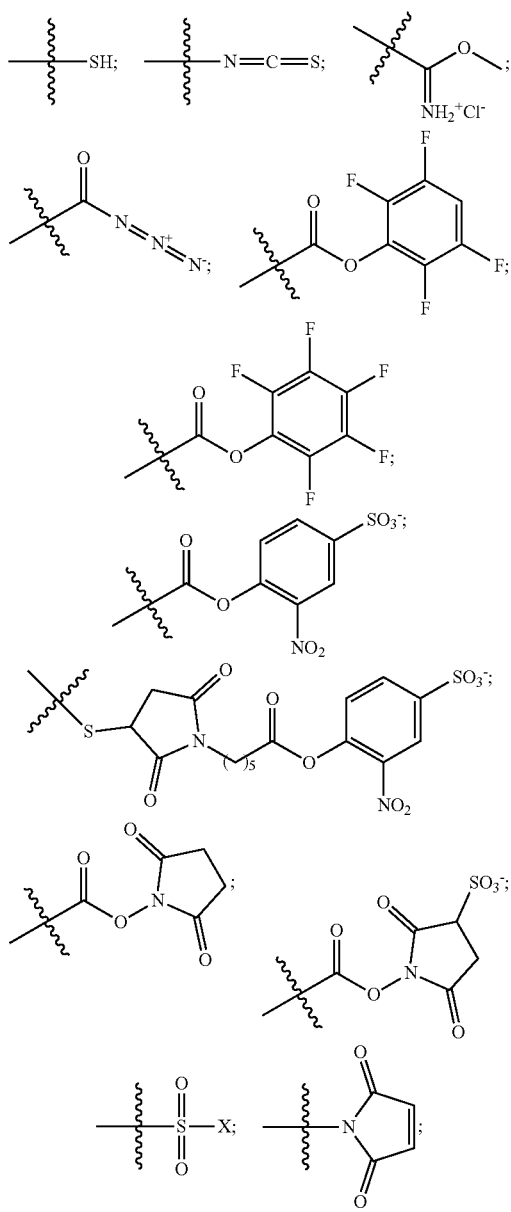
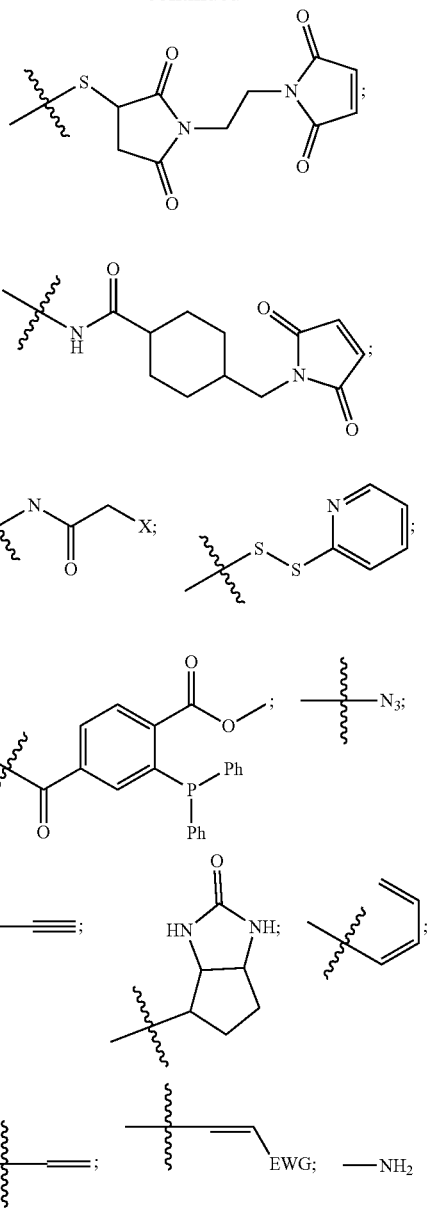
wherein:
X is halo; and
EWG is an electron withdrawing group.
* * * * *

UNITED STATES PATENT AND TRADEMARK OFFICE
CERTIFICATE OF CORRECTION

PATENT NO. : 11,390,754 B2
APPLICATION NO. : 16/099988
DATED : July 19, 2022
INVENTOR(S) : Sharat Singh et al.

Page 1 of 2

It is certified that error appears in the above-identified patent and that said Letters Patent is hereby corrected as shown below:

In the Claims

Column 130, Claim 7, Lines 5-12:

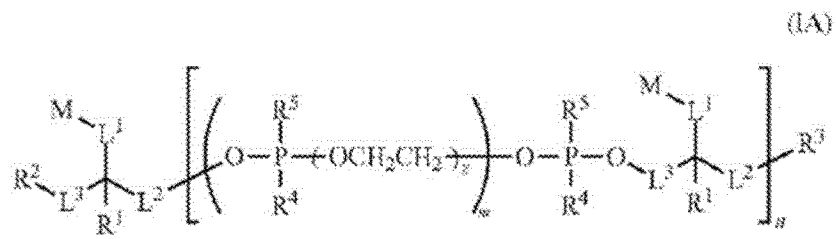

Should read:

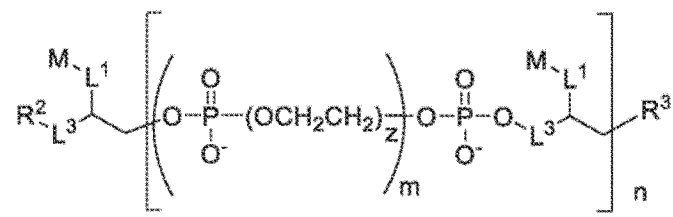

(IA)

Column 134, Claim 17, Lines 34-42:

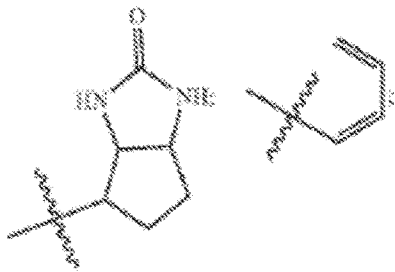

Signed and Sealed this
Eighteenth Day of June, 2024

Katherine Kelly Vidal
Director of the United States Patent and Trademark Office